(12) United States Patent
Hansen et al.

(10) Patent No.: US 9,139,657 B2
(45) Date of Patent: *Sep. 22, 2015

(54) CLASS I ANTI-CEA ANTIBODIES AND USES THEREOF

(71) Applicant: Immunomedics, Inc., Morris Plains, NJ (US)

(72) Inventors: Hans J. Hansen, Picayune, MS (US); Chien-Hsing Chang, Downingtown, PA (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/576,656

(22) Filed: Dec. 19, 2014

(65) Prior Publication Data

US 2015/0111279 A1  Apr. 23, 2015

Related U.S. Application Data

(62) Division of application No. 14/289,066, filed on May 28, 2014, now Pat. No. 8,945,554, which is a division of application No. 14/066,097, filed on Oct. 29, 2013, now Pat. No. 8,771,690, which is a division of application No. 13/898,992, filed on May 21, 2013, now Pat. No. 8,603,479, which is a division of application No. 13/606,899, filed on Sep. 7, 2012, now Pat. No. 8,470,994, which is a division of application No. 12/846,062, filed on Jul. 29, 2010, now Pat. No. 8,287,865.

(60) Provisional application No. 61/242,872, filed on Sep. 16, 2009.

(51) Int. Cl.
```
A61K 39/395    (2006.01)
C07K 16/30     (2006.01)
A61K 47/48     (2006.01)
A61K 51/08     (2006.01)
C07K 16/28     (2006.01)
A61K 51/10     (2006.01)
A61K 49/00     (2006.01)
A61K 49/22     (2006.01)
C07K 14/54     (2006.01)
A61K 39/00     (2006.01)
```

(52) U.S. Cl.
CPC ....... *C07K 16/3007* (2013.01); *A61K 39/39558* (2013.01); *A61K 47/481* (2013.01); *A61K 47/484* (2013.01); *A61K 47/4843* (2013.01); *A61K 47/48215* (2013.01); *A61K 47/48376* (2013.01); *A61K 47/48423* (2013.01); *A61K 47/48438* (2013.01); *A61K 47/48446* (2013.01); *A61K 47/48484* (2013.01); *A61K 47/48561* (2013.01); *A61K 47/48576* (2013.01); *A61K 49/0058* (2013.01); *A61K 49/221* (2013.01); *A61K 51/088* (2013.01); *A61K 51/1027* (2013.01); *A61K 51/1093* (2013.01); *A61K 51/1096* (2013.01); *C07K 14/54* (2013.01); *C07K 16/2803* (2013.01); *C07K 16/3076* (2013.01); *A61K 2039/505* (2013.01); *A61K 2039/545* (2013.01); *C07K 2317/24* (2013.01); *C07K 2317/31* (2013.01); *C07K 2317/33* (2013.01); *C07K 2317/515* (2013.01); *C07K 2317/55* (2013.01); *C07K 2317/565* (2013.01); *C07K 2317/76* (2013.01); *C07K 2317/92* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,818,709 A | 4/1989 | Primus et al. |
| 6,676,924 B2 | 1/2004 | Hansen et al. |
| 6,759,045 B2 | 7/2004 | Goldenberg et al. |

(Continued)

FOREIGN PATENT DOCUMENTS

| | | |
|---|---|---|
| EP | 0388914 | 7/1996 |
| EP | 0727435 | 6/1998 |

(Continued)

OTHER PUBLICATIONS

Audette et al., "Monoclonal antibody against carcinoembryonic antigen (CEA) identifies two new forms of crossreacting antigens of molecular weight 90,000 and 160,000 in normal granulocytes", Mol. Immunol. 24.(11):1177-86 (1987).

(Continued)

*Primary Examiner* — Sheela J Huff
(74) *Attorney, Agent, or Firm* — Richard A. Nakashima

(57) ABSTRACT

The present invention provides compositions and methods of use of humanized, chimeric or human Class I anti-CEA antibodies or fragments thereof, preferably comprising the light chain variable region CDR sequences SASSRVSYIH (SEQ ID NO:1); GTSTLAS (SEQ ID NO:2); and QQWSYNPPT (SEQ ID NO:3); and the heavy chain variable region CDR sequences DYYMS (SEQ ID NO:4); FIANKANGHTTDYSPSVKG (SEQ ID NO:5); and DMGIRWNFDV (SEQ ID NO:6). The Class I anti-CEA antibodies or fragments are useful for treating diseases, such as cancer, wherein the diseased cells express CEACAM5 and/or CEACAM6 antigens. The Class I anti-CEA antibodies or fragments are also of use for interfering with specific processes, such as metastasis, invasiveness and/or adhesion of cancer cells, or for enhancing sensitivity of cancer cells to cytotoxic agents and have favorable effects on the survival of subjects with cancer.

36 Claims, 7 Drawing Sheets

(56) References Cited

U.S. PATENT DOCUMENTS

| | | | |
|---|---|---|---|
| 7,323,168 | B2 | 1/2008 | Goldenberg et al. |
| 7,521,056 | B2 | 4/2009 | Chang et al. |
| 7,527,787 | B2 | 5/2009 | Chang et al. |
| 7,534,866 | B2 | 5/2009 | Chang et al. |
| 7,541,440 | B2 | 6/2009 | Goldenberg et al. |
| 7,550,143 | B2 | 6/2009 | Chang et al. |
| 7,662,378 | B2 | 2/2010 | Goldenberg et al. |
| 7,666,400 | B2 | 2/2010 | Chang et al. |
| 7,803,372 | B2 | 9/2010 | Goldenberg et al. |
| 8,287,865 | B2 | 10/2012 | Hansen et al. |
| 8,603,479 | B1 | 12/2013 | Hansen et al. |
| 8,771,690 | B2 | 7/2014 | Hansen et al. |
| 2009/0028851 | A1 | 1/2009 | Stuhmer et al. |
| 2009/0185974 | A1 | 7/2009 | Goldenberg et al. |
| 2010/0034738 | A1 | 2/2010 | Goldenberg et al. |

FOREIGN PATENT DOCUMENTS

| | | |
|---|---|---|
| WO | 9201047 | 1/1992 |
| WO | 9910494 | 3/1999 |
| WO | 2002044217 | 6/2002 |
| WO | 2004035537 | 4/2004 |
| WO | 2004056312 | 7/2004 |
| WO | 2007071426 | 6/2007 |
| WO | 2007098283 | 8/2007 |

OTHER PUBLICATIONS

Beauchemin et al., "Redefined nomenclature for members of the carcinoembryonic antigen family", Exp. Cell Res. 252(2):243-9 (1999).
Bjerner et al., "Protein epitopes in carcinoembryonic antigen. Report of the ISOBM TD8 workshop", Tumour Biol. 23 (4):249-62 (2002).
Blumenthal et al., "Inhibition of adhesion, invasion, and metastasis by antibodies targeting CEACAM6 (NCA-90) and CEACAM5 (Carcinoembryonic Antigen)", Cancer Res. 65(19):8809-17 (2005).
Blumenthal et al., "Expression patterns of CEACAM5 and CEACAM6 in primary and metastatic cancers", BMC Cancer 7:2 (2007).
Blumenthal et al., "Carcinoembryonic antigen antibody inhibits lung metastasis and augments chemotherapy in a human colonic carcinoma xenograft", Cancer Immunol. Immunother. 54(4):315-27 (2005).
Blumenthal et al., "Targeted therapy of athymic mice bearing GW-39 human colonic cancer micrometastases with 131I-labeled monoclonal antibodies", Cancer Res. 52(21):6036-44 (1992).
Chen et al., "CGM1a antigen of neutrophils, a receptor of gonococcal opacity proteins", Proc. Natl. Acad. Sci. USA 93.(25):14851-6 (1996).
Duxbury et al., "CEACAM6 cross-linking induces caveolin-1-dependent, Src-mediated focal adhesion kinase phosphorylation in BxPC3 pancreatic adenocarcinoma cells", J. Biol. Chem. 279(22):23176-82 (2004).
Duxbury et al., "CEACAM6 as a novel target for indirect type 1 immunotoxin-based therapy in pancreatic adenocarcinoma", Biochem. Biophys. Res. Commun. 317(3):837-43 (2004).
Duxbury et al., "CEACAM6 is a novel biomarker in pancreatic adenocarcinoma and PanIN lesions", Ann. Surg. 241 (3):491-6 (2005).
Duxbury et al., "c-Src-dependent cross-talk between CEACAM6 and alphavbeta3 integrin enhances pancreatic adenocarcinoma cell adhesion to extracellular matrix components", Biochem. Biophys. Res. Commun. 317(1):133-41 (2004).
Duxbury et al., "CEACAM6 is a determinant of pancreatic adenocarcinoma cellular invasiveness", Br. J. Cancer. 91 (7):1384-90 (2004).
Duxbury et al., "A novel role for carcinoembryonic antigen-related cell adhesion molecule 6 as a determinant of gemcitabine chemoresistance in pancreatic adenocarcinoma cells", Cancer Res. 64(11):3987-93 (2004).
Duxbury et al., "CEACAM6 gene silencing impairs anoikis resistance and in vivo metastatic ability of pancreatic adenocarcinoma cells", Oncogene 23(2):465-73 (2004).
Gangopadhyay et al., "Adhesion of colorectal carcinoma cells to the endothelium is mediated by cytokines from CEA stimulated Kupffer cells", Clin. Exp. Metastasis 16(8):703-12 (1998).
Glinsky et al., "Anti-adhesion cancer therapy", Cancer Metastasis Rev. 17(2):177-85 (1998).
Gold et al., "The carcinoembryonic antigen (CEA): past present, and future", McGill J. Med. 3:46-66 (1997).
Gold et al., "Specific carcinoembryonic antigens of the human digestive system", J. Exp. Med. 122(3):467-81 (1965).
Goldenberg et al., "Carcinoembryonic antigen in histopathology: immunoperoxidase staining of conventional tissue sections", J. Natl. Cancer Inst. 57(1):11-22 (1976).
Grunert et al., "CD66b, CD66c and carcinoembryonic antigen (CEA) are independently regulated markers in sera of tumor patients", Int. J. Cancer 63(3):349-55 (1995).
Hammarstrom et al., "Antigenic sites in carcinoembryonic antigen", Cancer Res. 49(17):4852-8 (1989).
Hammarstrom et al., "The carcinoembryonic antigen (Cea) family: structures, suggested functions and expression in normal and malignant tissues", Semin. Cancer Biol. 9(2):67-81 (1999).
Hansen et al., "Characterization of second-generation monoclonal antibodies against carcinoembryonic antigen", Cancer 71(11):3478-85 (1993).
Hashino et al., "Metastatic potential of human colorectal carcinoma SW1222 cells transfected with cDNA encoding carcinoembryonic antigen", Clin. Exp. Metastasis 12(4):324-8 (1994).
Hinoda et al., "Induction of nonspecific cross-reacting antigen mRNA by interferon-gamma and anti-fibronectin receptor antibody in colon cancer cells", J. Gastroenterol. 32(2):200-5 (1997).
Ilantzis et al., "Deregulated expression of the human tumor marker CEA and CEA family member CEACAM6 disrupts tissue architecture and blocks colonocyte differentiation", Neoplasia 4(2):151-63 (2002).
Jantscheff et al., "Expression of CEACAM6 in resectable colorectal cancer: a factor of independent prognostic significance", J. Clin. Oncol. (19):3638-46 (2003).
Jantscheff et al., "Expression of CEACAM6 in colorectal cancer: Significant association with overall and disease-free survival", Eur. J. Cancer 37:S290 (2001).
Kerbel et al., "Is there a role for 'anti-adhesives' as chemosensitizers in the treatment of solid tumors by chemotherapy?", Bulletin de l'institut Pasteur 92:248-256 (1995).
Kim et al., "Carcino-embryonic antigen may function as a chemoattractant in colorectal-carcinoma cell lines", Int. J. Cancer 82(6):880-5 (1999).
Kodera et al., "Expression of carcinoembryonic antigen (Cea) and nonspecific crossreacting antigen (Nca) in gastrointestinal cancer; the correlation with degree of differentiation", Br J. Cancer 68(1):130-6 (1993).
Kraus et al., "In vitro chemo- and radio-resistance in small cell lung cancer correlates with cell adhesion and constitutive activation of AKT and MAP kinase pathways", Oncogene 21(57):8683-95 (2002).
Kuijpers et al., "CD66 nonspecific cross-reacting antigens are involved in neutrophil adherence to cytokine-activated endothelial cells", J. Cell Biol. 118(2):457-66 (1992).
Kuroki et al., "Nonspecific cross-reacting antigen-50/90 (Nca-50190) as a new tumor marker", Anticancer Res. 19 (6C):5599-606 (1999).
Kuroki et al., Three different NCA species, CGM6/CD67, NCA-95, and NCA-90, are comprised in the major 90 to 100-kDa band of granulocyte Nca detectable upon SDs-polyacrylamide gel electrophoresis, Biochem. Biophys. Res. Commun. 182(2):501-6 (1992).
Kuroki et al., "Molecular cloning of nonspecific cross-reacting antigens in human granulocytes", J. Biol. Chem. 266 (18):11810-7 (1991).
Leung et al., "Chimerization of LL2, a rapidly internalizing antibody specific for B cell lymphoma", Hybridoma 13 (6):469-76 (1994).
Minami et al., "Role of carcinoembryonic antigen in the progression of colon cancer cells that express carbohydrate antigen", Cancer Res. 61(6):2732-5 (2001).

(56) References Cited

OTHER PUBLICATIONS

Nagel et al., "Genomic organization, splice variants and expression of CGM1, a CD66-related member of the carcinoembryonic antigen gene family", Eur. J. Biochem. 214(1):27-35 (1993).

Neumaier et al., "Monoclonal antibodies for carcinoembryonic antigen (CEA) as a model system: identification of two novel CEA-related antigens in meconium and colorectal carcinoma tissue by Western blots and differential immunoaffinity chromatography", J. Immunol. 135(5):3604-9 (1985).

Oikawa et al., "Cell adhesion activity of non-specific cross-reacting antigen (NCA) and carcinoembryonic antigen (CEA) expressed on CHO cell surface: homophilic and heterophilic adhesion", Biochem. Biophys. Res. Commun. 164 (1):39-45 (1989).

Ordonez et al., "Human carcinoembryonic antigen functions as a general inhibitor of anoikis", Cancer Res. 60 (13):3419-24 (2000).

Rossi et al., "Nonfamilial medullary thyroid carcinoma", Am. J. Surg. 139(4):554-60 (1980).

Samaan et al., "Medullary thyroid carcinoma: prognosis of familial versus sporadic disease and the role of radiotherapy", J. Clin. Endocrinol. Metab. 67(4):801-5 (1988).

Scholzel et al., "Carcinoembryonic antigen family members CEACAM6 and CEACAM7 are differentially expressed in normal tissues and oppositely deregulated in hyperplastic colorectal polyps and early adenomas", Am. J. Pathol 156:595-605 (2000).

Schroder et al., "Prognostic factors in medullary thyroid carcinomas. Survival in relation to age, sex, stage, histology, immunocytochemistry, and DNA content", Cancer 61(4):806-16 (1988).

Sharkey et al., "Clinical evaluation of tumor targeting with a high-affinity, anticarcinoembryonic-antigen-specific, murine monoclonal antibody, MN-14", Cancer 71(6):2082-96 (1993).

Sharkey et al., "Evaluation of a complementarity-determining region-grafted (humanized) anti-carcinoembryonic antigen monoclonal antibody in preclinical and clinical studies", Cancer Res. 55(23 Suppl):5935s-5945s (1995).

Sharkey et al., "Successful radioimmunotherapy for lung metastasis of human colonic cancer in nude mice", J. Natl. Cancer Inst. 83(9):627-32 (1991).

Blumenthal et al., "Inhibition of adhesion, invasion, and metastasis by antibodies targeting CEACAM6 (NCA-90) and CEACAM5 (Carcinoembryonic Antigen)", Cancer Res. 2005 Oct 1;65(19):8809-17.

Buras et al., "Animal models of sepsis: setting the stage", Nat Rev Drug Discov. Oct. 2005;4(10):854-65.

Goldenberg et al., "Multifunctional antibodies by the Dock-and-Lock method for improved cancer imaging and therapy by pretargeting", J Nucl Med. Jan. 2008;49(1):158-63.

Qu et al., "Development of humanized antibodies as cancer therapeutics", Methods. May 2005;36(1):84-95.

Rittirsch et al., "The disconnect between animal models of sepsis and human sepsis", J Leukoc Biol. Jan. 2007:81 (1):137-43.

Shively et al., "CEA-related antigens: molecular biology and clinical significance", Crit. Rev. Oncol. Hematol. 2 (4):355-99 (1985).

Skubitz et al., "CD66 family members are associated with tyrosine kinase activity in human neutrophils", J. Immunol. 155(11):5382-90 (1995).

Skubitz et al., "CD66a, CD66b, CD66c, and CD66d each independently stimulate neutrophils", J. Leukoc. Biol. 60 (1):106-17 (1996).

Soeth et al., "Controlled ribozyme targeting demonstrates an antiapoptotic effect of carcinoembryonic antigen in HT29 colon cancer cells", Clin. Cancer Res. 7(7):2022-30 (2001).

Stein et al., "A humanized monoclonal antibody to carcinoembryonic antigen, labetuzumab, inhibits tumor growth and sensitizes human medullary thyroid cancer xenografts to dacarbazine chemotherapy", Mol. Cancer Ther. 3 (12):1559-64 (2004).

Taheri et al., "The adhesion and differentiation-inhibitory activities of the immunoglobulin superfamily member, carcinoembryonic antigen, can be independently blocked", J Biol Chem. 2003 Apr 25;278(17):14632-9.

Thomas et al., "The effect of transfection of the CEA gene on the metastatic behavior of the human colorectal cancer cell line MIP-101", Cancer Lett. 92(1):59-66 (1995).

Thompson et al., "Carcinoembryonic antigen gene family: molecular biology and clinical perspectives", J. Clin. Lab. Anal. 5(5):344-66 (1991).

Wirth et al., "Inhibition of endogenous carcinoembryonic antigen (CEA) increases the apoptotic rate of colon cancer cells and inhibits metastatic tumor growth", Clin. Exp. Metastasis 19(2):155-60 (2002).

Yamanaka et al., "Analysis of heterophilic cell adhesion mediated by CD66b and CD66c using their soluble recombinant proteins", Biochem. Biophys. Res. Commun. 219(3):842-7 (1996).

Yoshioka et al., "Homotypic adhesion through carcinoembryonic antigen plays a role in hepatic metastasis development", Jpn. J. Cancer Res. 89(2):177-85 (1998).

Zhou et al., "Specificity of anti-carcinoembryonic antigen monoclonal antibodies and their effects on Cea-mediated adhesion", Cancer Res. 53(16):3817-22 (1993).

```
                  1                        10                  20                        30                     40
KOL  V_H          EVQLVESGGGVVQPGRSLRLSCSSSGFIFSSSYAMYWVRQA
MN15 V_H          EVRLVESGGGLVQGPGSLRLSCAASGFALTDYMSWVRQS
hMN15 V_H         QVQLVESGGGVVQPGRSLRLSCSSSGFALTDYMSWVRQA 50  52 A B C                       60                         70
KOL  V_H          PGKGLEWVAIIWD--DGSDQHYADSVKGRFTISRDNSKNT
MN15 V_H          PGKTLEWLGFIANKANGHTTDYSPSVKGRFTISRDNSQTI
hMN15 V_H         PGKGLEWLGFIANKANGHTTDYSPSVKGRFTISRDNSKNT 80 82 A B C                    90              100 A B C D E F G H I
KOL  V_H          LFLQMDSLRPEDTGVYFCARDGGHGFCSSASCFGPDY
MN15 V_H          LYLQMNTLRTEDSATYYCARDMGIRWNF------DV
hMN15 V_H         LFLQMDSLRPEDTGVYFCARDMGIRWNF------DV 103           110  113
KOL  V_H          WGQGTPVTVSS
MN15 V_H          WGQGTTVTVSS
hMN15 V_H         WGQGTPVTVSS
```

FIG. 2

```
              1                    10                  20                  30          40
REI   V_K     DIQLTQSPSSLSASVGDRVTITC QASQDIIKYLN WYQQKP
MN15  V_K     DIQLTQSPAIMSASPGEKVTMTC SASS-RVSYIH WYQQKS
hMN15 V_K     DIQLTQSPSSLSASVGDRVTMTC SASS-RVSYIH WYQQKP 50                  60                  70          80
REI   V_K     GKAPKLLIY EASNLQA GVPSRFSGSGSGTDFTFTISSLQP
MN15  V_K     GTSPKRWIY GTSTLAS GVPARFSGSGSGTSYSLTISSMEA
hMN15 V_K     GKAPKRWIY GTSTLAS GVPARFSGSGSGTDFTFTISSLQP 90                 100       107
REI   V_K     EDIATYYC QQYQSLPYT FGQGTKVEIK
MN15  V_K     EDAATYYC QQWSYNPPT FGAGTKLELKR
hMN15 V_K     EDIATYYC QQWSYNPPT FGQGTKVEIKR
```

FIG. 3

CLASS I ANTI-CEA ANTIBODIES AND USES THEREOF

RELATED APPLICATIONS

This application is a divisional of U.S. patent application Ser. No. 14/289,06, filed May 28, 2014, which was a divisional of U.S. patent application Ser. No. 14/066,097 (now U.S. Pat. No. 8,771,690), filed Oct. 29, 2013, which was a divisional of U.S. patent application Ser. No. 13/898,992 (now U.S. Pat. No. 8,603,479), filed May 21, 2013, which was a divisional of U.S. patent application Ser. No. 13/606,899 (now U.S. Pat. No. 8,470,994), filed Sep. 7, 2012, which was a divisional of U.S. patent application Ser. No. 12/846,062 (now U.S. Pat. No. 8,287,865), filed Jul. 29, 2010. The present application claims the benefit under 35 U.S.C. 119(e) of Provisional U.S. Patent Application Ser. No. 61/242,872, filed Sep. 16, 2009, the entire text of which is incorporated herein by reference.

SEQUENCE LISTING

The instant application contains a Sequence Listing which has been submitted via EFS-Web and is hereby incorporated by reference in its entirety. Said ASCII copy, created on Jul. 9, 2010, is named IMM322US.txt, and is 17,798 bytes in size.

BACKGROUND OF THE INVENTION

1. Field of the Invention

The invention relates to compositions for and methods of treating cancers that express CEACAM 5 (carcinoembryonic antigen, "CEA") and/or CEACAM6 (NCA-90), such as medullary thyroid cancer (MTC), colorectal cancers, hepatocellular carcinoma, gastric cancer, lung cancer, head-and-neck cancers, bladder cancer, prostate cancer, breast cancer, pancreatic cancer, uterine cancer, ovarian cancer, hematopoietic cancers, leukemia and other cancers in which CEACAM5 and/or CEACAM6 are expressed. The methods comprise administering a Class I anti-CEA antibody or fragment that targets both CEACAM5 and CEACAM6, preferably in combination with at least one other therapeutic agent, such as another antibody, a chemotherapeutic agent, a radioactive agent, an antisense oligonucleotide, an immunomodulator, an immunoconjugate or a combination thereof. The Class I anti-CEA MAb may be administered prior to, with or after administering the therapeutic agent. In preferred embodiments the Class I anti-CEA antibody is a chimeric, humanized or human monoclonal antibody (MAb) comprising the light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6). More preferably, the chimeric, humanized or human Class I anti-CEA MAb retains the binding affinity characteristics and specificities of a parental murine Class I anti-CEA MAb, but possesses more of the antigenic and effector properties of a human antibody.

2. Related Art

CEA (CEACAM5) is an oncofetal antigen commonly expressed in a number of epithelial cancers, most commonly those arising in the colon but also in the breast, lung, pancreas, thyroid (medullary type) and ovary (Goldenberg et al., J. Natl. Cancer Inst. 57: 11-22, 1976; Shively, et al., Crit. Rev. Oncol. Hematol. 2:355-399, 1985). The human CEA gene family is composed of 7 known genes belonging to the CEACAM subgroup. These subgroup members are mainly associated with the cell membrane and show a complex expression pattern in normal and cancerous tissues. The CEACAM5 gene, also known as CD66e, codes for the CEA protein (Beauchemin et al., Exp Cell Res 252:243, 1999). CEACAM5 was first described in 1965 as a gastrointestinal oncofetal antigen (Gold et al., J Exp Med 122:467-481, 1965), but is now known to be overexpressed in a majority of carcinomas, including those of the gastrointestinal tract, the respiratory and genitourinary systems, and breast cancer (Goldenberg et al., J Natl Cancer Inst. 57:11-22, 1976; Shively and Beatty, Crit Rev Oncol Hematol 2:355-99, 1985).

CEACAM6 (also called CD66c or NCA-90) is a nonspecific cross-reacting glycoprotein antigen that shares some, but not all, antigenic determinants with CEACAM5 (Kuroki et al., Biochem Biophys Res Comm 182:501-06, 1992). CEACAM6 is expressed on granulocytes and epithelia from various organs, and has a broader expression zone in proliferating cells of hyperplastic colonic polyps and adenomas, compared with normal mucosa, as well as by many human cancers (Scholzel et al., Am J Pathol 157:1051-52, 2000; Kuroki et al., Anticancer Res 19:5599-5606, 1999). Relatively high serum levels of CEACAM6 are found in patients with lung, pancreatic, breast, colorectal, and hepatocellular carcinomas. The amount of CEACAM6 does not correlate with the amount of CEACAM5 expressed (Kuroki et al., Anticancer Res 19:5599-5606, 1999).

Expression of CEACAM6 in colorectal cancer correlates inversely with cellular differentiation (Ilantzis et al., Neoplasia 4:151-63, 2002) and is an independent prognostic factor associated with a higher risk of relapse (Jantscheff et al., J Clin Oncol 21:3638-46, 2003). Both CEACAM5 and CEACAM6 have a role in cell adhesion, invasion and metastasis. CEACAM5 has been shown to be involved in both homophilic (CEA to CEA) and heterophilic (CEA binding to non-CEA molecules) interactions (Bechimol et al., Cell 57:327-34, 1989; Oikawa et al., Biochem Biophys Res Comm 164:39-45, 1989), suggesting to some that it is an intercellular adhesion molecule involved in cancer invasion and metastasis (Thomas et al., Cancer Lett 92:59-66, 1995). These reactions were completely inhibited by the Fab' fragment of an anti-CEACAM5 antibody (Oikawa et al., Biochem Biophys Res Comm 164:39-45, 1989). CEACAM6 also exhibits homotypic binding with other members of the CEA family and heterotypic interactions with integrin receptors (Stanners and Fuks, In: *Cell Adhesion and Communication by the CEA Family*, (Stanners ed.) Vol. 5, pp. 57-72, Harwood Academic Publ., Amsterdam, 1998). Antibodies that target the N-domain of CEACAM6 interfere with cell-cell interactions (Yamanka et al. Biochem Biophys Res Comm 219:842-47, 1996). Many breast, pancreatic, colonic and non-small-cell lung cancer (NSCLC) cell lines express CEACAM6 and anti-CEACAM6 antibody inhibits in vitro migration, invasion, and adhesion of antigen-positive cells (Blumenthal et al, Cancer Res 65:8809-17, 2005).

Anti-CEA antibodies are classified into different categories, depending on their cross-reactivity with antigens other than CEA. Anti-CEA antibody classification was described by Primus and Goldenberg, U.S. Pat. No. 4,818,709 (incorporated herein by reference from Col. 3, line 5 through Col. 26, line 49 of U.S. Pat. No. 4,818,709). The classification of anti-CEA antibodies is determined by their binding to CEA, meconium antigen (MA) and nonspecific cross-reacting antigen (NCA). Class I anti-CEA antibodies bind to all three antigens. Class II antibodies bind to MA and CEA, but not to NCA. Class III antibodies bind only to CEA (U.S. Pat. No. 4,818,709). Examples of each class of anti-CEA antibody are known, such as MN-3, MN-15 and NP-1 (Class I); MN-2, NP-2 and NP-3 (Class II); and MN-14 and NP-4 (Class III) (U.S. Pat. No. 4,818,709; Blumenthal et al. BMC Cancer 7:2 (2007)).

The epitopic binding sites of various anti-CEA antibodies have also been identified. The MN-15 antibody binds to the A1B1 domain of CEA, the MN-3 antibody binds to the N-terminal domain of CEA and the MN-14 antibody binds to the A3B3 (CD66e) domain of CEA (Blumenthal et al. BMC Cancer 7:2 (2007)). There is no direct correlation between epitopic binding site and class of anti-CEA antibody. For example, MN-3 and MN-15 are both Class I anti-CEA antibodies, reactive with NCA, MA and CEA, but bind respectively to the N-terminal and A1B1 domains of CEA. Primus and Goldenberg (U.S. Pat. No. 4,818,709) reported a complicated pattern of cross-blocking activity between the different anti-CEA antibodies, with NP-1 (Class I) and NP-2 (Class II) cross-blocking binding to CEA of each other, but neither blocking binding of NP-3 (Class II). However, by definition Class I anti-CEA antibodies bind to both CEACAM5 and CEACAM6, while Class III anti-CEA antibodies bind only to CEACAM5.

Anti-CEA antibodies have been suggested for therapeutic treatment of a variety of cancers. For example, medullary thyroid cancer (MTC) confined to the thyroid gland is generally treated by total thyroidectomy and central lymph node dissection. However, disease recurs in approximately 50% of these patients. In addition, the prognosis of patients with unresectable disease or distant metastases is poor, less than 30% survive 10 years (Rossi et al., Amer. J. Surgery, 139:554 (1980); Samaan et al., J. Clin. Endocrinol. Metab., 67:801 (1988); Schroder et al., Cancer, 61:806 (1988)). These patients are left with few therapeutic choices (Principles and Practice of Oncology, DeVita, Hellman and Rosenberg (eds.), New York: JB Lippincott Co., pp. 1333-1435 (1989); Cancer et al., Current Problems Surgery, 22: 1 (1985)). The Class III anti-CEA antibody MN-14 has been reported to be effective for therapy of human medullary thyroid carcinoma in an animal xenograft model system, when used in conjunction with pro-apoptotic agents such as DTIC, CPT-11 and 5-fluorouracil (U.S. patent application Ser. No. 10/680,734, the Examples section of which is incorporated herein by reference). The Class III anti-CEA antibody reportedly sensitized cancer cells to therapy with chemotherapeutic agents and the combination of antibody and chemotherapeutic agent was reported to have synergistic effects on tumors compared with either antibody or chemotherapeutic agent alone (U.S. Ser. No. 10/680,734). Anti-CEA antibodies of different classes (such as MN-3, MN-14 and MN-15) have been proposed for use in treating a variety of tumors.

There still exists a need to provide more effective methods of treating CEA-expressing cancers. The present invention provides compositions and methods for effective anti-cancer therapy utilizing Class I anti-CEA MAbs, such as chimeric, humanized or human antibodies comprising the light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYS-PSVKG (SEQ ID NO:5); and DMGIRWNFDV (SEQ ID NO:6), which are capable of binding to both CEACAM5 and CEACAM6. Preferably, the Class I anti-CEA MAb is humanized, and used in combination with a therapeutic agent, particularly a chemotherapeutic agent, to yield an effective therapeutic treatment for CEACAM5- or CEACAM6-expressing cancers with minimal toxicity. The separate administration of Class I antibody and therapeutic agent provides enhanced results and the versatility and the flexibility to tailor individual treatment methods.

SUMMARY OF THE INVENTION

In certain embodiments, the present invention concerns a composition comprising at least one chimeric, humanized or human Class I anti-CEA MAb or antigen-binding fragment thereof. Where antibody fragments of a Class I anti-CEA antibody are utilized, the fragment may be selected from the group consisting of F(ab)$_2$, Fab', Fab, Fv, scFv fragments and single domain antibodies (VHH). Preferably, the Class I anti-CEA MAb is a chimeric, humanized or human monoclonal antibody or fragment thereof that comprises the light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYS-PSVKG (SEQ ID NO:5); and DMGIRWNFDV (SEQ ID NO:6). More preferably, the variable region sequences of the chimeric, humanized or human Class I anti-CEA antibody are attached to human IgG1 or IgG4 constant region sequences.

In alternative embodiments, the chimeric, humanized or human Class I anti-CEA MAb or antigen-binding fragment thereof may be one that blocks or competes for binding to CEACAM5 and/or CEACAM6 with a monoclonal antibody having light chain CDRs comprising CDR1 having an amino acid sequence SASSRVSYIH (SEQ ID NO:1); CDR2 having an amino acid sequence GTSTLAS (SEQ ID NO:2); and CDR3 having an amino acid sequence QQWSYNPPT (SEQ ID NO:3); and heavy chain CDRs comprising CDR1 having an amino acid sequence DYYMS (SEQ ID NO:4); CDR2 having an amino acid sequence FIANKANGHTTDYSPS-VKG (SEQ ID NO:5); and CDR3 having an amino acid sequence DMGIRWNFDV (SEQ ID NO:6). Such competitive binding or blocking studies may be performed by any of a wide variety of known binding assays, as exemplified in FIG. 1 and FIG. 4 and their corresponding Examples.

The skilled artisan will be aware, as discussed in more detail below, that chimeric antibodies retain the framework region (FR) sequences of a parent murine antibody, while humanized and human antibodies will generally have human antibody FR sequences. Preferably, the humanized Class I anti-CEA MAb comprises the heavy chain FR sequences of the human KOL antibody and the light chain FR sequences of the human REI antibody. However, where appropriate, certain murine FR amino acid residues may be substituted for corresponding human FR amino acid residues. In preferred embodiments, the substituted murine FR residues may include one or more amino acid residues selected from heavy chain amino acid residues 28, 29, 30, 48 and 49 of SEQ ID NO:10 and light chain amino acid residues 21, 47 and 60 of SEQ ID NO:9. In more preferred embodiments, the humanized Class I anti-CEA MAb comprises the variable region sequences of SEQ ID NO:7 and SEQ ID NO:8, while the chimeric Class I anti-CEA MAb comprises the variable region sequences of SEQ ID NO:9 and SEQ ID NO:10.

In various embodiments, the Class I anti-CEA antibody will bind to CEA, MA and NCA and will also bind to human granulocytes. The Class I anti-CEA MAb binds to both CEACAM5 and CEACAM6. Where the Class I anti-CEA MAb or fragment thereof is chimeric, humanized, or human, the antibody will preferably retain the binding specificity of a parental murine Class I anti-CEA MAb.

In certain embodiments the Class I anti-CEA MAb may be conjugated to at least one therapeutic agent and/or diagnostic agent to form an immunoconjugate. Such immunoconjugates are of use for delivering therapeutic and/or diagnostic agents to a CEACAM5- or CEACAM6-expressing cancer cell and/or for therapy or diagnosis of cancer. In alternative embodiments, the Class I anti-CEA MAb may be administered as a "naked" (unconjugated) antibody. Either naked antibodies or immunoconjugates may be administered before, simultaneously with or after another therapeutic anti-cancer agent.

Other embodiments concern methods of diagnosing or treating cancer, comprising administering a Class I anti-CEA antibody or fragment thereof to a subject. For diagnostic purposes, the antibody may be conjugated to at least one diagnostic agent. After allowing the labeled antibody to bind to CEA-expressing cells, the distribution of bound antibody may be imaged or otherwise determined. For treatment of CEA-expressing tumors, the Class I anti-CEA antibody may be conjugated to at least one therapeutic agent and the immunoconjugate administered to a patient.

In alternative embodiments, the Class I anti-CEA antibody may be part of a bispecific or multispecific antibody. Such antibodies may contain at least one binding site for a tumor-associated antigen, such as CEA, and at least one other binding site for a hapten attached to a targetable construct. Such bispecific or multispecific antibodies may be used in pretargeting methods for diagnosis or treatment of cancer, as discussed in more detail below. Where pretargeting is used, the bispecific or multispecific antibody may be administered to a subject and allowed to localize to a CEACAM5- or CEACAM6-expressing tumor. A clearing agent may optionally be added to enhance clearance of unbound antibody from the circulation. After allowing a sufficient time for unbound antibody to clear from the circulation, a targetable construct conjugated to a therapeutic and/or diagnostic agent may be administered to the subject to bind to the antibody localized at the tumor site. Delivery of diagnostic agents using a Class I anti-CEA antibody may be performed as part of an endoscopic, intravascular or intraoperative procedure.

In various embodiments, the therapeutic agent is selected from the group consisting of a naked antibody, a cytotoxic agent, a drug, a radionuclide, boron atoms, an immunomodulator, a photoactive therapeutic agent, an immunoconjugate, a hormone, an enzyme, an antisense oligonucleotide or a combination thereof, optionally formulated in a pharmaceutically acceptable vehicle. Preferably, the therapeutic agent is a cytotoxic agent selected from a drug or a toxin. It is contemplated that the drug may possess a pharmaceutical property selected from the group consisting of antimitotic, alkylating, antimetabolite, antiangiogenic, apoptotic, alkaloid, COX-2, and antibiotic agents and combinations thereof. Preferably, the drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs. Exemplary oligonucleotides may include siRNA or RNAi molecules. Many examples of therapeutic oligonucleotides are known in the art and any such known example may be attached to a subject Class I anti-CEA antibody or fragment thereof.

When the therapeutic agent is a microbial, plant or animal toxin, the toxin can be selected from the group consisting of ricin, abrin, alpha toxin, saporin, ribonuclease (RNase), DNase I, Staphylococcal enterotoxin-A, pokeweed antiviral protein, gelonin, diphtheria toxin, Pseudomonas exotoxin and Pseudomonas endotoxin.

In another embodiment, an immunomodulator is administered prior to the administration of a therapeutically effective amount of a Class I anti-CEA monoclonal antibody or fragment thereof alone or a Class I anti-CEA monoclonal antibody and at least one therapeutic agent. Immunomodulators may be selected from the group consisting of a cytokine, a stem cell growth factor, a lymphotoxin, an hematopoietic factor, a colony stimulating factor (CSF), an interferon (IFN), a stem cell growth factor, erythropoietin, thrombopoietin and a combination thereof. Preferably, the lymphotoxin is tumor necrosis factor (TNF), the hematopoietic factor is an interleukin (IL), the colony stimulating factor is granulocyte-colony stimulating factor (G-CSF) or granulocyte macrophage-colony stimulating factor (GM-CSF)), the interferon is interferon-α, -β or -γ, and the stem cell growth factor is designated "S1 factor."

Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines Administration of a cytokine prior to, simultaneous with, or subsequent to exposure to a cytotoxic agent that results in myeloid or hematopoietic toxicity is described in U.S. Pat. No. 5,120,525, the Examples section of which is incorporated herein by reference.

In certain preferred embodiments, the therapeutic agent is a radionuclide that has an energy between 20 and 10,000 keV. Preferably, the radionuclide is selected from the group consisting of $^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb.

The methods of the instant invention may further comprise administering to a subject, either concurrently or sequentially, a therapeutically effective amount of a second humanized, chimeric, human or murine monoclonal antibody or fragment thereof. The second MAb may bind to a tumor-associated antigen (TAA) selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-βR, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PIGF, complement factors C3, C3a, C3b, C5a, C5 and an oncogene product. Similarly, the methods may comprise administering to a subject, either concurrently or sequentially, a therapeutically effective amount of a second humanized, chimeric or human monoclonal antibody or fragment thereof selected from the group consisting of a Class I or Class II or Class III anti-CEA monoclonal antibody or fragment thereof. Where a second antibody or fragment is administered concurrently with the Class I anti-CEA antibody, it may be administered as a separate molecule or alternatively as part of a bispecific or multispecific antibody construct with the Class I anti-CEA antibody.

The second MAb may be selected from any of a wide variety of anti-cancer antibodies known in the art, including but not limited to hPAM4 (U.S. Pat. No. 7,282,567), hA20 (U.S. Pat. No. 7,151,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387,772), hL243 (U.S. Pat. No. 7,612,180), hMN-14 (U.S. Pat. No. 6,676,924), hRS7 (U.S. Pat. No. 7,238,785), hMN-3 (U.S. Pat. No. 7,541,440) and hR1 (U.S. patent application Ser. No. 12/722,645, filed Mar. 12, 2010) the Examples section of each cited patent or application incorporated herein by reference. The second MAb may also be selected from any anti-hapten antibody known in the art, including but not limited to h679 (U.S. Pat. No. 7,429,381) and 734 (U.S. Pat. No. 7,405,320) or h734 (U.S. Pat. No. 7,405,320), the Examples section of each of which is incorporated herein by reference.

In various embodiments, the bispecific or multispecific antibodies or other antibody constructs may be produced as fusion proteins or by use of the Dock-and-Lock (DNL) technology, as described in more detail below. Compositions and methods for production and use of DNL constructs have been reported (see, e.g., U.S. Pat. Nos. 7,521,056; 7,527,787; 7,534,866; 7,550,143 and 7,666,400 and U.S. patent application Ser. Nos. 12/418,877; 12/544,476; 12/731,781; 12/752,649; and 12/754,740, the Examples section of each of which is incorporated herein by reference). DNL complexes are formed by attachment of a selected effector to an anchoring domain (AD) or dimerization and docking domain (DDD) peptide sequence. The DNL complex forms when the DDD sequence spontaneously dimerizes and binds to the AD sequence. Virtually any effector moiety may be attached to a DDD or AD sequence, including antibodies or antibody fragments, peptides, proteins, enzymes, toxins, therapeutic agents, diagnostic agents, immunomodulators, polymers such as polyethylene glycol (PEG), cytokines, chemokines, growth factors, hormones and any other type of molecule or complex. In preferred embodiments, the DNL complex may comprise an antibody or fragment thereof comprising light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYS-PSVKG (SEQ ID NO:5); and DMGIRWNFDV (SEQ ID NO:6). In other preferred embodiments, the DNL complex may further comprise a cytokine or a polyethylene glycol moiety. These embodiments are not limiting and the skilled artisan will realize that the claimed DNL complexes may comprise a Class I anti-CEA antibody moiety attached to virtually any other effector moiety.

BRIEF DESCRIPTION OF THE DRAWINGS

FIG. 2 shows a comparison of the heavy chain variable region sequences of the human KOL antibody (SEQ ID NO:38), the murine MN-15 antibody (SEQ ID NO:10), and the humanized MN-15 antibody (hMN-15) (SEQ ID NO:8). CDR sequences are boxed and differences between the human KOL and murine MN-15 FR sequences are indicated by underlining in the murine MN-15 sequence. Murine FR amino acids that are retained in the hMN-15 sequence are indicated by underlining in the hMN-15 sequence.

FIG. 3 shows a comparison of the light chain variable region sequences of the human REI antibody (SEQ ID NO:39), the murine MN-15 antibody (SEQ ID NO:9), and the humanized MN-15 antibody (hMN-15) (SEQ ID NO:7). CDR sequences are boxed and differences between the human REI and murine MN-15 FR sequences are indicated by underlining in the murine MN-15 sequence. Murine FR amino acids that are retained in the hMN-15 sequence are indicated by underlining in the hMN-15 sequence.

Figure 1:
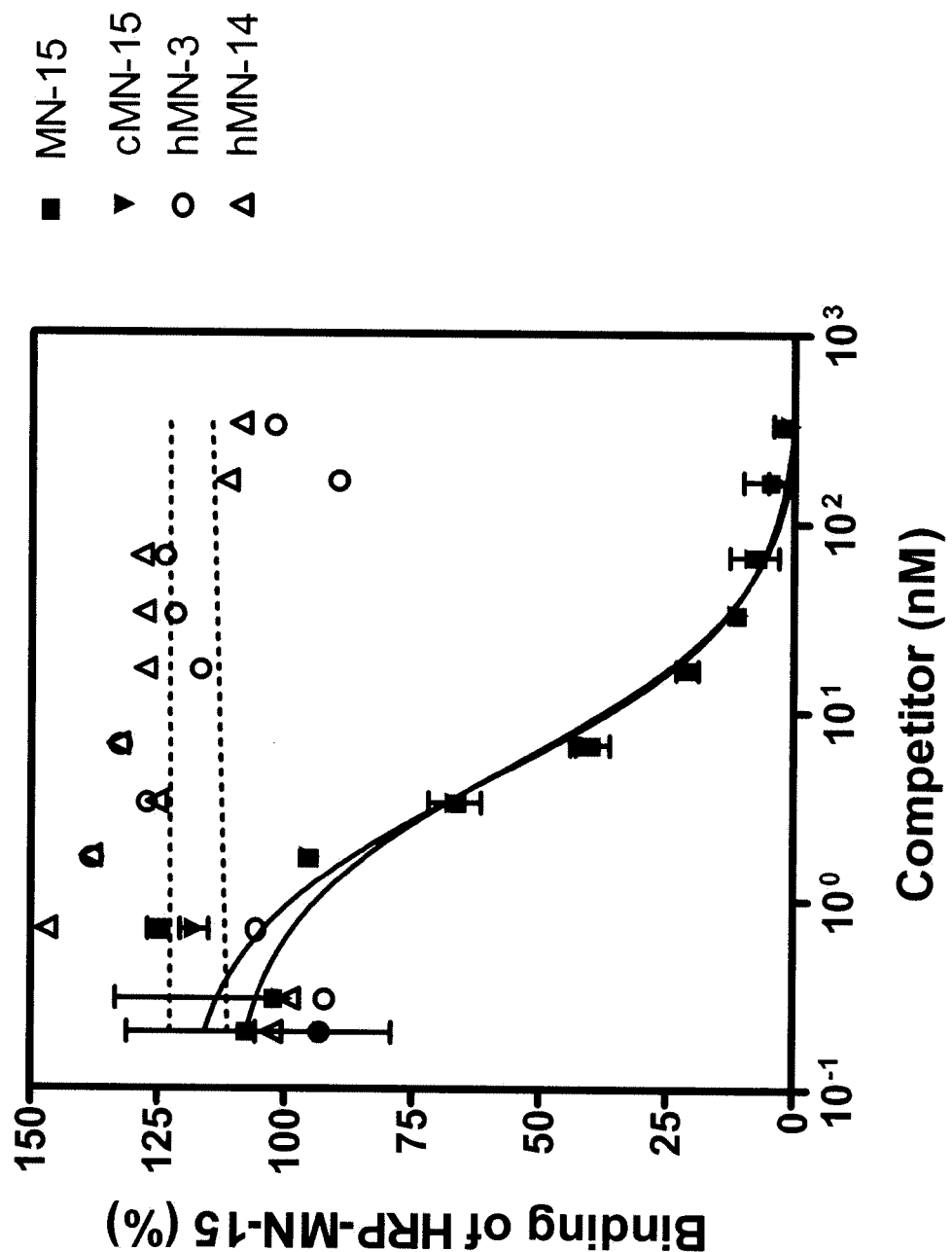
FIG. 1 illustrates an exemplary comparative CEA binding curve for chimeric MN-15 (cMN-15) vs. the parental murine MN-15 antibody.

Fab' (10 µg/mL). Mice also received a single 100 µg dose of the same Fab' 1 day after cell implantation.

DETAILED DESCRIPTION OF THE PREFERRED EMBODIMENTS

The present invention provides methods of treatment in which a chimeric, humanized or human Class I anti-CEA antibody or fragment thereof is administered to a subject with cancer. The methods are of use to treat cancers that express CEACAM5 (CEA) and/or CEACAM6, since Class I anti-CEA antibodies bind to both antigens. The antibodies may be administered as naked (unconjugated) antibodies or as immunoconjugates attached to one or more therapeutic agents. The naked antibodies may be administered prior to, simultaneously with or after one or more other therapeutic anti-cancer agents.

The method is useful for treating a wide variety of cancers, including but not limited to medullary thyroid carcinoma, colorectal cancers, hepatocellular carcinoma, pancreatic, breast, lung, head-and-neck, bladder, uterine and ovarian cancers, and even cancers that do not express CEACAM5 or CEACAM6 at very high levels. For example, treatment is contemplated in cancers that express CEA at levels of at least 100 ng/g of tissue.

As used herein, the phrase "Class I anti-CEA" antibody or antibody fragment means an antibody or fragment that binds the CEA antigen (or CD66e) and also with normal cross-reactive antigen (NCA), meconium antigen (MA), granulocytes and CD66a-d (see, Primus et al., U.S. Pat. No. 4,818, 709, incorporated herein by reference). In a preferred embodiment, the Class I anti-CEA antibody is a humanized, chimeric or human antibody having light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6).

The mechanism of tumor cell killing by the naked Class I anti-CEA antibody is not known with certainty and likely involves several mechanisms. It is hypothesized that the naked antibody alone or in combination with a therapeutic agent may affect tumor growth by blocking biological activities of their respective antigen or by stimulating natural immunological functions, such as antibody-dependent cell-mediated cytotoxicity (ADCC) or complement-mediated lysis. Additionally, the naked antibody alone or in combination with the therapeutic agent may treat and control the cancer by inhibiting cell growth and cell cycle progression, inducing apoptosis, inhibiting angiogenesis, inhibiting metastatic activity, and/or affecting tumor cell adhesion. In fact, the anti-CEA antibody or fragment thereof may be more effective in treating metastases than primary cancers, since the metastases may be more susceptible to antagonists of tumor cell adhesion. The present treatment method provides a treatment plan that may be optimized to provide the maximum anti-tumor activity for individual patients by allowing the titration of the antibody and one or more different therapeutic agents to provide an effective treatment regimen.

In certain alternative embodiments, a preferred naked murine, chimeric, humanized or human Class I anti-CEA antibody may be a monovalent construct, comprising only one binding site for CEACAM5 or CEACAM6. For example, a Fab, Fab' or scFv antibody fragment comprising light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6) may be utilized. Such monovalent constructs may be conjugated to a polymer, such as PEG, to extend its serum half-life, using techniques described in detail below. Another alternative monovalent antibody fragment may contain a human IgG4 constant region and hinge. In certain embodiments, the native IgG4 sequence may be modified by replacing cysteine residues with serine residues, as discussed in McDonagh et al., (2006, Protein Eng Des Sel 19:299-307). In still other alternative embodiments, a monovalent antibody fragment may be constructed by the DNL technique, also described in detail below.

Definitions

As used herein, the terms "a", "an" and "the" may refer to either the singular or plural, unless the context otherwise makes clear that only the singular is meant.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, Fab', Fab, Fv, scFv (single chain Fv) and the like. Regardless of structure, an antibody fragment binds with the same antigen that is recognized by the intact antibody. The term "antibody fragment" includes isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region. The Fv fragments may be constructed in different ways as to yield multivalent and/or multispecific binding forms. In the former case of multivalent, they react with more than one binding site against the CEA epitope, whereas with multispecific forms, more than one epitope (either of CEA or even against CEA and a different antigen) is bound.

A naked antibody is generally an entire antibody which is not conjugated to a therapeutic agent. This is so because the Fc portion of the antibody molecule provides effector or immunological functions, such as complement fixation and ADCC (antibody dependent cell cytotoxicity). However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with the disease progression. Naked antibodies include both polyclonal and monoclonal antibodies, and fragments thereof, that include murine antibodies, as well as certain recombinant antibodies, such as chimeric, humanized or human antibodies and fragments thereof. As defined herein, "naked" is synonymous with "unconjugated," and means not linked or conjugated to any therapeutic agent.

A chimeric antibody is a recombinant protein that contains the variable domains of the heavy and light antibody chains, including the complementarity determining regions (CDRs) of an antibody derived from one species, preferably a rodent antibody, while the constant domains of the antibody molecule are derived from those of a human antibody.

A humanized antibody is a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody or antibody fragment, and is useful in the treatment of a disease. Examples of therapeutic agents include antibodies, antibody fragments, immunoconjugates, drugs, enzymes, cytotoxic agents, toxins, nucleases, hormones, immunomodulators, chelators, boron compounds, photoactive agents or dyes, radioisotopes or radionuclides, antisense oligonucleotides or combinations thereof.

As used herein, the term antibody fusion protein is a recombinantly produced antigen-binding molecule in which one or more of the same or different natural antibody, single-chain antibody or antibody fragment segments with the same or different specificities are linked. A Class I anti-CEA fusion protein comprises at least one CEA binding site. Preferably, the Class I anti-CEA fusion protein comprises the light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYS-PSVKG (SEQ ID NO:5); and DMGIRWNFDV (SEQ ID NO:6). Valency of the fusion protein indicates the total number of binding arms or sites the fusion protein has to antigen(s) or epitope(s); i.e., monovalent, bivalent, trivalent or mutlivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. In certain embodiments, a fusion protein may comprise one or more antibodies or fragments thereof linked to a different effector protein or peptide, such as a cytokine, hormone, growth factor, binding protein, binding peptide or other effector. An exemplary fusion protein may comprise an antibody or fragment thereof attached to an AD or DDD peptide, as discussed in detail below.

An immunomodulator is a therapeutic agent that when present, alters, suppresses or stimulates the body's immune system. Typically, an immunomodulator of use acts to stimulate immune cells to proliferate or become activated in an immune response cascade, such as macrophages, B-cells, and/or T-cells. An example of an immunomodulator as described herein is a cytokine, which is a soluble small protein of approximately 5-20 kDa that is released by one cell population (e.g., primed T-Iymphocytes) on contact with specific antigens, and which acts as an intercellular mediator between cells. As the skilled artisan will understand, examples of cytokines include lymphokines, monokines, interleukins, and several related signalling molecules, such as tumor necrosis factor (TNF) and interferons. Chemokines are a subset of cytokines Certain interleukins and interferons are examples of cytokines that stimulate T cell or other immune cell proliferation.

Preparation of Monoclonal Antibodies. Including Chimeric, Humanized and Human Antibodies Monoclonal antibodies (MAbs) to specific antigens may be obtained by methods known to those skilled in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

MAbs to peptide backbones are generated by well-known methods for Ab production. For example, injection of an immunogen, such as (peptide)$_N$-KLH, wherein KLH is keyhole limpet hemocyanin, and N=1-30, in complete Freund's adjuvant, followed by two subsequent injections of the same immunogen suspended in incomplete Freund's adjuvant into immunocompetent animals. The animals are given a final i.v. boost of antigen, followed by spleen cell harvesting three days later. Harvested spleen cells are then fused with Sp2/0-Ag14 myeloma cells and culture supernatants of the resulting clones analyzed for anti-peptide reactivity using a direct binding ELISA. Fine specificity of generated MAbs can be analyzed for by using peptide fragments of the original immunogen. These fragments can be prepared readily using an automated peptide synthesizer. For MAb production, enzyme-deficient hybridomas are isolated to enable selection of fused cell lines. This technique also can be used to raise antibodies to one or more chelating or other hapten moieties, such as In(III)-DTPA chelates. Monoclonal mouse antibodies to an In(III)-di-DTPA are known (U.S. Pat. No. 5,256,395 to Barbet).

Another method for producing antibodies is by production in the milk of transgenic livestock. See, e.g., Colman, A., Biochem. Soc. Symp., 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors that contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

After the initial raising of antibodies to the immunogen, the variable genes of the monoclonal antibodies can be cloned from the hybridoma cells, sequenced and subsequently prepared by recombinant techniques. General techniques for cloning murine immunoglobulin variable domains are described, for example, by the publication of Orlandi et al., Proc. Nat'l Acad. Sci. USA 86: 3833 (1989). Humanization and chimerization of murine antibodies and antibody fragments are well known to those skilled in the art. A chimeric antibody is a recombinant protein that contains the variable domains including the CDRs derived from one species of animal, such as a rodent antibody, while the remainder of the antibody molecule; i.e., the constant domains, is derived from a human antibody. The use of antibody components derived from humanized and chimeric monoclonal antibodies alleviates potential problems associated with the immunogenicity of murine constant regions. Techniques for constructing chimeric antibodies are well known to those of skill in the art. As an example, Leung et al., Hybridoma 13:469 (1994), describe how they produced an LL2 chimera by combining DNA sequences encoding the $V_K$ and $V_H$ domains of the murine LL2 monoclonal antibody, an anti-CD22 antibody, with respective human K and $IgG_1$ constant region domains.

A chimeric monoclonal antibody (MAb) can be humanized by replacing the sequences of the murine FR in the variable domains of the chimeric MAb with one or more different human FR. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988).

Additionally, knowing that chimeric anti-CEA exhibits a binding affinity comparable to that of its murine counterpart, defective designs, if any, in the original version of the humanized anti-CEA MAb can be identified by mixing and matching the light and heavy chains of the chimeric anti-CEA to those of the humanized version. Preferably, the humanized anti-CEA antibody comprises the light chain variable region CDR sequences CDR1 having an amino acid sequence SASSRVSYIH (SEQ ID NO:1); CDR2 having an amino acid sequence GTSTLAS (SEQ ID NO:2); and CDR3 having an amino acid sequence QQWSYNPPT (SEQ ID NO:3); and the heavy chain variable region CDR sequences CDR1 having an amino acid sequence DYYMS (SEQ ID NO:4); CDR2 having an amino acid sequence FIANKANGHTTDYSPSVKG (SEQ ID NO:5); and CDR3 having an amino acid sequence DMGIRWNFDV (SEQ ID NO:6). More preferably, the humanized anti-CEA antibody comprises the light chain FR sequences of the human REI antibody and the heavy chain FR sequences of the human KOL antibody. Most preferably, the humanized anti-CEA antibody comprises one or more murine FR amino acid residues selected from the heavy chain amino acid residues 28, 29, 30, 48 and 49 of SEQ ID NO:10 and light chain amino acid residues 21, 47 and 60 of SEQ ID NO:9.

Alternatively, a combination of framework sequences from 2 or more different human antibodies can be used for $V_H$ and $V_K$ FR sequences. The production of humanized MAbs is described, for example, by Jones et al., Nature 321:522 (1986), Riechmann et al., Nature 332:323 (1988), Verhoeyen et al., Science 239:1534 (1988), Carter et al., Proc. Nat'l Acad Sci. USA 89:4285 (1992), Sandhu, Crit. Rev. Biotech. 12:437 (1992), and Singer et al., J. Immun. 150:2844 (1993). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, W00029584A1.

In another embodiment, a Class I anti-CEA monoclonal antibody is a human antibody. The human anti-CEA MAb, or another human antibody, can be obtained from a transgenic non-human animal. See, e.g., Mendez et al., Nature Genetics, 15: 146-156 (1997) and U.S. Pat. No. 5,633,425. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., Nature Genetics, 16: 133 (1997). In this methodology microcells containing human chromosomes are fused with mouse embryonic stem cells. Transferred chromosomes are stably retained, and adult chimeras exhibit proper tissue-specific expression.

As an alternative, human antibody fragments may be isolated from a combinatorial immunoglobulin library. See, e.g., Barbas et al., METHODS: A Companion to Methods in Enzymology 2: 119 (1991), and Winter et al., Ann. Rev. Immunol. 12: 433 (1994). Many of the difficulties associated with generating monoclonal antibodies by B-cell immortalization can be overcome by engineering and expressing antibody fragments in E. coli, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of E. coli directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

In one embodiment, the antibodies are produced as described in Hansen et al., Cancer, 71:3478 (1993); Hansen et al., U.S. Pat. No. 5,874,540; Primus et al., U.S. Pat. No. 4,818,709, and Shively et al., U.S. Pat. No. 5,081,235, the examples section of each of which is incorporated herein by reference.

Production of Antibody Fragments

Certain embodiments concern the use of fragments of a Class I anti-CEA antibody, preferably comprising light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYS-PSVKG (SEQ ID NO:5); and DMGIRWNFDV (SEQ ID NO:6). Antibody fragments which recognize the same epitope as a parent antibody can be generated by known techniques. For example, antibody fragments can be prepared by proteolytic hydrolysis of an antibody or by expression in E. coli of the DNA coding for the fragment. The antibody fragments are antigen binding portions of an antibody, such as F(ab')$_2$, Fab', Fab, Fv, scFv and the like, and can be obtained by pepsin or papain digestion of whole antibodies by conventional methods or by genetic engineering techniques.

For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331, 647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. I, page 422 (Academic Press 1967), and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., Proc. Nat'l. Acad. Sci. U.S.A. 69:2659 (1972). Alternatively, the variable chains can be linked by an intermolecular disulfide bond or cross-linked by chemicals such as glutaraldehyde. See, for example, Sandhu, Crit. Rev. Biotech. 12:437 (1992). Preferably, the Fv fragments comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector that is subsequently introduced into a host cell, such as E. coli. The recombinant host cells synthesize a single polypeptide chain with a linker peptide bridging the two V domains. Methods for producing scFvs are described, for example, by Whitlow et al., Methods: A Companion to Methods in Enzymology, 2:97 (1991). Also see Bird et al., Science 242:423 (1988), Ladner et al., U.S. Pat. No. 4,946,778; Pack et al., Bio Technology 11: 1271 (1993) and Sandhu, supra.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody producing cells. See, for example, Larrick et at., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain-only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007).

Humanized, Chimeric and Human Anti-CEA Antibodies for Treatment

Various embodiments concern compositions and methods using murine, chimeric, humanized or human Class I anti-CEA antibodies and fragments thereof for treatment of disease states, such as cancer. Preferably, the Class I anti-CEA antibody or fragment thereof comprises light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6). The antibodies can be used to treat any cancer that expresses CEACAM5 and/or CEACAM6. Exemplary CEACAM5 or CEACAM6 expressing carcinomas include without limitation medullary thyroid cancer, colorectal cancer, pancreatic cancer, hepatocellular carcinoma, gastric cancer, lung cancer, head- and neck cancers, urinary bladder cancer, prostate cancer, uterine cancer, endometrial cancer, breast cancer, hematopoietic cancer, leukemia and ovarian cancer.

Compositions

A composition as claimed herein may comprise at least one Class I anti-CEA monoclonal antibody (MAb) or fragment thereof. In certain embodiments, the composition or method of use may also include at least one therapeutic agent, which may be conjugated to the Class I anti-CEA antibody or not conjugated. In compositions comprising more than one antibody or antibody fragments, such as a second Class I anti-CEA antibody, the second antibody is non-blocking (i.e., does not block binding of the first Class I anti-CEA antibody or antibody fragment to its target antigen).

In one embodiment, the Class I anti-CEA monoclonal antibody or fragment thereof is humanized, human or chimeric, wherein the humanized, human or chimeric MAb retains substantially the Class I anti-CEA binding specificity of a murine Class I anti-CEA MAb. In a preferred embodiment, the Class I anti-CEA monoclonal antibody or fragment thereof comprises the light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6).

In a preferred embodiment, the Class I anti-CEA monoclonal antibody or fragment thereof is a humanized antibody that comprises human antibody FR and constant region sequences, preferably with FR sequences from the human REI and KOL antibodies. The framework regions (FRs) preferably comprise at least one amino acid substituted from the corresponding FRs of a murine monoclonal antibody. Still more preferred, the humanized antibody or fragment thereof comprises at least one amino acid selected from the group consisting of heavy chain amino acid residues 28, 29, 30, 48 and 49 of SEQ ID NO:10 and light chain amino acid residues 21, 47 and 60 of SEQ ID NO:9. The amino acid sequence of a preferred humanized antibody comprises the variable region sequences of SEQ ID NO:7 and SEQ ID NO:8.

Another embodiment is a composition comprising a chimeric Class I anti-CEA monoclonal antibody or fragment thereof, optionally with at least one therapeutic agent, which may be conjugated or unconjugated. Preferably, the chimeric antibody or fragment thereof comprises light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6). More preferably, the chimeric antibody comprises the variable region sequences of SEQ ID NO:9 and SEQ ID NO:10.

Also described herein is a composition comprising a naked murine, humanized, chimeric or human Class I anti-CEA antibody or fragment thereof. The composition may optionally comprise a therapeutic agent, such as a second naked or conjugated anti-CEA antibody or antibody fragment thereof. Where a second anti-CEA antibody is used, it is non-blocking, i.e., does not block binding of the first Class I anti-CEA antibody or fragment thereof. In other words, both anti-CEA antibodies or fragments thereof are non-blocking to each other, allowing both antibodies or fragments thereof to bind to CEA (CD66e).

In still other embodiments, the claimed compositions and methods may comprise an antibody or fragment that binds to the same epitope of CEACAM5 or CEACAM6 as a Class I anti-CEA antibody comprising light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6). Evidence of epitope binding may be determined, for example, by competitive binding assays that are well known in the art. Additionally, other anti-CEA antibodies, such as Class II or Class III anti-CEA antibodies, can be used in combination with the Class I anti-CEA antibody, in either a naked or conjugated form. For example, one or more chimeric or humanized Class II or Class III anti-CEA antibodies or fragments thereof may be combined with a Class I anti-CEA antibody or fragment thereof.

A number of publications disclose MAbs that recognize CEA and different members of the CEA gene family, such as Thompson et al., J. Clin. Lab. Anal. 5:344 (1991); Kuroki et al., J. Biol. Chem. 266:11810 (1991); Nagel et al., Eur. J. Biochem. 214:27 (1993); Skubitz et al., J. Immunol. 155: 5382 (1995); Skubitz et al., J. Leukoc. Biol. 60:106 (1996); and Chen et al., Proc. Natl. Acad Sci. 93: 14851 (1996).

The second antibody or antibody fragment may be either unconjugated (naked) or conjugated to at least one therapeutic agent (immunocougate). Immunoconjugates can be prepared by indirectly conjugating a therapeutic agent to an antibody component. General techniques are described in Shih et al., Int. J. Cancer, 41:832 (1988); Shih et al., Int. J. Cancer, 46:1101 (1990); and Shih et al., U.S. Pat. No. 5,057, 313. The general method involves reacting an antibody component having an oxidized carbohydrate portion with a carrier polymer that has at least one free amine function and that is loaded with a plurality of drug, toxin, chelator, boron addends, or other therapeutic agents. This reaction results in an initial Schiff base (imine) linkage, which can be stabilized by reduction to a secondary amine to form the final conjugate. However, as discussed below many methods of preparing immunoconjugates are known in the art and any such known method may be used.

Also contemplated are compositions and methods of use comprising a humanized, chimeric, murine or human Class I anti-CEA antibody or fragment thereof and a second antibody or fragment that binds to a different tumor-associated antigen (TAA). In one embodiment, the second antibody or fragment thereof binds to a TAA selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5 and an oncogene product.

Methods

Also described herein are methods for treating carcinomas. Exemplary carcinomas include medullary thyroid carcinoma, colorectal cancer, pancreatic cancer, breast cancer, hepatocellular carcinoma, ovarian cancer, gastric cancer, prostate cancer, uterine cancer, hematopoietic cancer, leukemia and various lung, head-and-neck, endometrial, bladder, and liver cancers that express CEACAM5 and/or CEACAM6. The CEA levels in these types of cancers are lower than present in medullary thyroid carcinomas but all that is necessary is that the CEACAM5 and/or CEACAM6 levels be sufficiently high so that the Class I anti-CEA therapy provides an effective treatment. Normal colon mucosa has about 100-500 ng/gram but carcinomas expressing CEA at levels of about 5 mcg/gram of tissue are suitable for treatment with the methods described herein.

For example, contemplated herein is a method for treating cancer comprising administering to a subject, either concurrently or sequentially, a therapeutically effective amount of a Class I anti-CEA monoclonal antibody or fragment thereof and at least one therapeutic agent, optionally formulated in a pharmaceutically acceptable vehicle. Preferably, the Class I anti-CEA monoclonal antibody or fragment thereof is chimeric, murine, humanized or human, wherein the Class I anti-CEA MAb retains substantially the Class I anti-CEA binding specificity of a parental murine MAb. More preferably, the Class I anti-CEA antibody comprises light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6). Preferably the therapeutic agent is a cytotoxic agent, more preferably an alkylating agent, and most preferably, dacarbazine (DTIC). But in another embodiment, the therapeutic agent may not be DTIC. Other classes of anti-cancer cytostatic and cytotoxic agents, such as 5-fluorouracil, CPT-11 and oxaliplatin can also be used in combinations with these antibodies, especially in the therapy of colorectal cancers. In other cancer types, cancer drugs that are known to be effective are also good candidates for combining with the antibody therapies proposed herein.

Also contemplated herein is a method for treating CEACAM5 and/or CEACAM6-expressing cancers comprising administering to a subject, either concurrently or sequentially, a therapeutically effective amount of a first Class I anti-CEA monoclonal antibody or fragment thereof and at least one therapeutic agent, and a naked or conjugated second humanized, chimeric, human or murine monoclonal antibody or fragment thereof, optionally formulated in a pharmaceutically acceptable vehicle. In one embodiment, the second antibody or fragment thereof binds to a tumor-associated antigen selected from the group consisting human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factors, interferon-α, interferon-β, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and LT. In another embodiment, the second antibody or fragment thereof can be a different Class I anti-CEA antibody or fragment thereof that is non-blocking. Alternatively the second antibody or fragment thereof may be a Class II or Class III anti-CEA antibody or fragment. The antibodies and fragments thereof may be administered either concurrently or sequentially with each other or the therapeutic agent.

A naked Class I anti-CEA antibody as described herein can significantly increase the chemosensitivity of cancer cells to one or more therapeutic agents. For example, treatment of colon cancer cells with a naked Class I, anti-CEA antibody comprising light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6), as described herein, either before or concurrently with a therapeutic agent, such as DTIC, CPT-11, 5'-fluorouracil (5-FU) or oxaliplatin, improves a cell's response to a therapeutic agent, such as a cytotoxic drug. Further, these therapeutic methods of treatment with a naked Class I, anti-CEA antibody alone or in combination with a therapeutic agent can be further enhanced by administering an immunomodulator as described herein, prior to the administration of the naked antibody or the administration of the naked antibody and at least one of the therapeutic agents.

Multimodal therapies include immunotherapy with a Class I anti-CEA antibody or fragment thereof, and a therapeutic agent, supplemented with administration of an unconjugated or conjugated antibody, unconjugated or conjugated fusion protein, or fragment thereof. For example, an unconjugated humanized, chimeric, murine or human Class I anti-CEA MAb or fragment thereof comprising light chain variable region CDR sequences SASSRVSYIH (SEQ ID NO:1);

GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6) may be combined with another naked humanized, murine, chimeric or human Class I anti-CEA antibody (such as an antibody against a different epitope on CEA), or a humanized, chimeric, murine or human Class I anti-CEA antibody immunoconjugate conjugated to a radioisotope, chemotherapeutic agent, cytokine, enzyme, enzyme-inhibitor, hormone or hormone antagonist, metal, toxin, antisense oligonucleotide (e.g., anti-bcl-2), or a combination thereof.

Preferably, a therapeutic agent of use is a drug used in standard cancer chemotherapy, such as taxane or platinum drugs in ovarian cancer, fluorouracil, CPT-11, and oxaloplatin drugs in colorectal cancer, gemcitabine in pancreatic and other cancers, or taxane derivatives in breast cancers. COX-2 inhibitors represent still another class of agents that show activity in combination with typical cytotoxic agents in cancer chemotherapy, and can be used in the same way, but combined in addition with anti-CEA antibodies alone or in combination with other anti-TAA antibodies. Optionally, these drugs can be used in combination with radiolabeled antibodies, either anti-CEA antibody conjugates or radioimmunoconjugates with other anti-TAA antibodies.

In a preferred embodiment, a naked Class I anti-CEA antibody or fragment thereof is administered sequentially (either prior to or after) or concurrently with dacarbazine (DTIC), doxorubin, cyclophosphamide or vincristine, or any combination of these. For example, DTIC and cylcophosphamide may be administered sequentially or concurrently with a naked Class I anti-CEA antibody or fragment thereof. Similarly, 5-fluorouracil in combination with folinic acid, alone or in combination with irinotecan (CPT-11) or oxaliplatin, is a regimen used to treat colorectal cancer. Other suitable combination chemotherapeutic regimens are well known, such as with oxaliplatin alone, or in combination with these other drugs, to those of skill in the art. Accordingly, combination therapy with any of these chemotherapeutic agents and a naked Class I anti-CEA antibody or fragment thereof can be used to treat cancer. In medullary thyroid carcinoma, other chemotherapeutic agents may be preferred, such as one of the alkylating agents (e.g., DTIC), as well as gemcitabine and other more recent classes of cytotoxic drugs. The chemotherapeutic drugs and a naked Class I anti-CEA antibody or fragment thereof, can be administered in any order, or together. In a preferred multimodal therapy, both chemotherapeutic drugs and naked Class I anti-CEA antibodies or fragments thereof are administered before, after, or co-administered with a conjugated or unconjugated anti-CEA antibody, fusion protein, or fragment thereof. Preferably, the Class I anti-CEA antibody or fragment thereof is a humanized antibody or fragment thereof.

A preferred treatment schedule of multimodal treatment is administering both hMN-15 and DTIC for 3 days, and administering only hMN-15 on days 7, 14, 21 and then every 21 days for a treatment duration of 12 months. The doses of hMN-15 are 0.5-15 mg/kg body weight per infusion, more preferably 2-8, and still more preferably 3-5 mg/kg per infusion, and the doses of DTIC are as currently applied at the preferred dose clinically, but could also be given at two-thirds or less of the maximum preferred dose in use, thereby decreasing drug-related adverse events. Repeated drug cycles can be given, such as every 1-6 months, with continuation of the naked antibody therapy, or with different schedules of radiolabeled antibody, drug-conjugated antibody, and inclusion of certain cytokines, such as G-CSF and/or GM-CSF, each dose adjusted so that toxicity to the patient is not enhanced by the therapeutic combination. The application of a cytokine growth factor, such as G-CSF, may enable even higher doses of myelosuppressive agents, such as radiolabeled antibody or cytotoxic drugs, to be administered, and these schedules and doses may be adjusted for the patients individually, depending on their disease status and prior therapy, bone marrow status and tolerability to additional cytotoxic therapies. In a preferred embodiment, the Class I anti-CEA antibody or fragment thereof is administered in a dosage of 100-600 milligrams protein per dose per injection. Still more preferred, the Class I anti-CEA antibody or fragment thereof is administered in a dosage of 300-400 milligrams of protein per dose per injection, with repeated doses preferred. The preferred antibody schedule is infusing once weekly or even less frequently, such as once every other week or even every third week, depending on a number of factors, including the extent of the disease and the amount of CEA circulating in the patient's blood.

Bispecific and Multispecific Antibodies

In various embodiments, the Class I anti-CEA antibody comprising light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6) may be incorporated into a bispecific or multispecific antibody. Bispecific antibodies are useful in a number of biomedical applications. For instance, pre-targeting methods with bispecific antibodies comprising at least one binding site for a tumor-associated antigen (TAA), such as CEACAM 5 and/or CEACAM6, as well as at least one binding site for a targetable construct conjugated to therapeutic or diagnostic agents, are also well known in the art (see, e.g., U.S. Pat. Nos. 7,300,644; 7,138,103; 7,074,405; 7,052,872; 6,962,702; 6,458,933, the Examples section of each of which is incorporated herein by reference). In other embodiments, bispecific antibodies comprising binding moieties targeting two different TAAs, or different epitopes of the same TAA, may be of therapeutic use.

Bispecific antibodies comprising the antigen-binding variable region sequences of any known anti-TAA antibody may be utilized, including but not limited to hPAM4 (U.S. Pat. No. 7,282,567), hA20 (U.S. Pat. No. 7,151,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387,772), hL243 (U.S. Pat. No. 7,612,180), hMN-14 (U.S. Pat. No. 6,676,924), hRS7 (U.S. Pat. No. 7,238,785), hMN-3 (U.S. Pat. No. 7,541,440) and hR1 (U.S. patent application Ser. No. 12/722,645, filed Mar. 12, 2010) the Examples section of each cited patent or application incorporated herein by reference.

Other antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645;

6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572;856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. Nos. 4,946,778 and 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabodies) and tetramers (termed tetrabodies) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143 and 7,666,400 and U.S. patent application Ser. Nos. 12/418,877; 12/544, 476; 12/731,781; 12/752,649; and 12/754,740, the Examples section of each of which is incorporated herein by reference).

Dock-and-Lock (DNL)

In preferred embodiments, bispecific or multispecific antibodies or other constructs may be produced using the dock-and-lock technology. The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RH), and each type has a and 13 isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561).

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RH dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RIIα and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2$b. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct or targetable conjugate) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are well known in the art, for example, as disclosed in Goodwin et al., U.S. Pat. No. 4,863, 713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077, 499; 7,011,812; 7,300,644; 7,074,405; 6,962,702; 7,387,772; 7,052,872; 7,138,103; 6,090,381; and 6,472,511.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents. The technique may also be utilized for antibody dependent enzyme prodrug therapy (ADEPT) by administering an enzyme conjugated to a targetable construct, followed by a prodrug that is converted into active form by the enzyme.

Therapeutic and Diagnostic Agents

In certain embodiments, the antibodies, antibody fragments or fusion proteins described herein may be administered alone, as a "naked" antibody, fragment or fusion protein. In alternative embodiments, the antibody, fragment or fusion protein may be administered before, concurrently with, or after at least one other therapeutic agent. In other alternatives, an antibody, fragment or fusion protein may be covalently or non-covalently attached to at least one therapeutic and/or diagnostic agent to form an immunoconjugate.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from barium compounds, gallium compounds and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Therapeutic agents are preferably selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, a photoactive therapeutic agent, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), COX-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epidophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide, transplatinum, thalidomide, thioguanine, thiotepa, teniposide, topotecan, uracil mustard, vinorelbine, vinblastine, vincristine and *vinca* alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin and LT. As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{124}$I, $^{123}$I, $^{131}$I, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Jori et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-Alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Other useful therapeutic agents comprise oligonucleotides, especially antisense oligonucleotides that preferably are directed against oncogenes and oncogene products of B-cell malignancies, such as bcl-2. Preferred antisense oligonucleotides include those known as siRNA or RNAi.

Immunoconjugates

Any of the antibodies, antibody fragments or antibody fusion proteins described herein may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, incorporated herein by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); Hansen et al., U.S. Pat. No. 5,443,953 (1995), Leung et al., U.S. Pat. No. 6,254,868, each incorporated herein by reference. The engineered carbohydrate moiety is used to attach the therapeutic or diagnostic agent.

In some embodiments, a chelating agent may be attached to an antibody, antibody fragment or fusion protein or to a targetable construct and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radio-imaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F—Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

Pharmaceutically Acceptable Vehicles

The compositions comprising murine, humanized, chimeric or human Class I anti-CEA MAbs to be delivered to a subject can comprise one or more pharmaceutically acceptable vehicles, one or more additional ingredients, or some combination of these. The Class I anti-CEA antibodies and fragments thereof can be formulated according to known methods to prepare pharmaceutically useful compositions. Sterile phosphate-buffered saline is one example of a pharmaceutically acceptable vehicle. Other acceptable vehicles are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The Class I anti-CEA antibody or fragment thereof can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

Additional pharmaceutical methods may be employed to control the duration of action of the therapeutic agent and/or antibody or fragment thereof. Control release preparations can be prepared through the use of polymers to complex or adsorb the antibody. For example, biocompatible polymers include matrices of poly (ethylene-co-vinyl acetate) and matrices of a polyanhydride copolymer of a stearic acid dimer and sebacic acid. Sherwood et al., Bio/Technology 10: 1446 (1992). The rate of release of an antibody or fragment thereof from such a matrix depends upon the molecular weight of the immunoconjugate or antibody, the amount of antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The Class I anti-CEA antibody or fragment thereof may also be administered to a mammal subcutaneously or by other parenteral routes. Moreover, the administration may be by continuous infusion or by single or multiple boluses. In general, the dosage of an administered antibody or fragment thereof for humans will vary depending upon such factors as the patient's age, weight, height, sex, general medical condition and previous medical history. Typically, it is desirable to provide the recipient with a dosage of antibody or fragment thereof that is in the range of from about 0.5 mg/kg to 20 mg/kg as a single intravenous infusion, although a lower or higher dosage also may be administered as circumstances dictate. This dosage may be repeated as needed, for example, once per month for 4-10 months, preferably once per every other week for 16 weeks, and more preferably, once per week for 8 weeks. It may also be given less frequently, such as every other week for several months or given more frequently and/or over a longer duration. The dosage may be given through various parenteral routes, with appropriate adjustment of the dose and schedule.

For purposes of therapy, the Class I anti-CEA antibody or fragment thereof is administered to a mammal in a therapeutically effective amount to reduce the size of a tumor as compared to untreated controls. Preferably, the Class I anti CEA antibody or fragment thereof is a humanized antibody or fragment thereof. A suitable subject for the present invention is usually a human, although a non-human mammal or animal subject is also contemplated. An antibody preparation is administered in a "therapeutically effective amount" if the amount administered is physiologically significant. An agent is physiologically significant if its presence results in a detectable change in the physiology of a recipient mammal.

In particular, an antibody preparation is physiologically significant if its presence invokes an antitumor response. A physiologically significant effect could also be the evocation of a humoral and/or cellular immune response in the recipient mammal.

Kits

Various embodiments may concern kits containing components suitable for treating or diagnosing diseased tissue in a patient. Exemplary kits may contain at least one antibody, antibody fragment or fusion protein as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, an Class I anti-CEA antibody or fragment thereof may be provided in the form of a prefilled syringe or autoinjection pen containing a sterile, liquid formulation or lyophilized preparation of antibody (e.g., Kivitz et al., Clin. Ther. 2006, 28:1619-29).

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person for use of the kit.

Expression Vectors

Still other embodiments may concern DNA sequences comprising a nucleic acid encoding an antibody, antibody fragment, fusion protein or bispecific antibody. Exemplary sequences that may be encoded and expressed include a Class I anti-CEA MAb or fragment thereof, a fusion protein comprising at least one Class I anti-CEA antibody or fragments thereof, a fusion protein comprising at least one first antibody or fragment and at least one second antibody or fragment. The first and second antibodies may comprise an Class I anti-CEA antibody and/or an antibody against a tumor or B-cell associated antigen such as B7, CD4, CD5, CD8 CD14, CD15, CD16, CD19, CD20, CD21, CD22, CD23, CD25, CD30, CD32b, CD33, CD37, CD38, CD40, CD40L, CD45, CD46, CD52, CD54, CD55, CD59, CD70, CD74, CD80, CD95, CD126, CD133, CD138, CD154, CEACAM6, ED-B fibronectin, IL-2, IL-6, IL-25, MUC1, MUC2, MUC3, MUC4, MIF, NCA-66, Ia, HM1.24, HLA-DR, tenascin, T101, TAC, TRAIL-R1, TRAIL-R2, VEGFR, EGFR, PlGF, ILGF, Flt-3, tenascin, complement factor C5, an oncogene product, Kras, cMET, bcl-2, and/or a hapten on a targetable construct. In preferred embodiments, the Class I antibody, antibody fragment, fusion protein or bispecific antibody comprises the light chain variable region CDR sequences SASSRVSYIH (SEQ ID NO:1); GTSTLAS (SEQ ID NO:2); and QQWSYNPPT (SEQ ID NO:3); and heavy chain variable region CDR sequences DYYMS (SEQ ID NO:4); FIANKANGHTTDYSPSVKG (SEQ ID NO:5); and DMGIRWNFDV (SEQ ID NO:6).

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express MAbs in a selected host cell, immunoglobulin enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine See Edelman et al., *Proc. Natl. Acad. Sci USA* 63: 78-85 (1969).

Also encompassed is a method of expressing antibodies or fragments thereof or fusion proteins. The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327; 7,537,930 and 7,608,425, the Examples section of each of which is incorporated herein by reference.

General Techniques for Construction of Anti-CEA Antibodies

The Vκ (variable light chain) and $V_H$ (variable heavy chain) sequences for Class I anti-CEA antibodies may be obtained by a variety of molecular cloning procedures, such as RT-PCR, 5'-RACE, and cDNA library screening. Specifically, the V genes of a Class I anti-CEA MAb from a cell that expresses a murine Class I anti-CEA MAb can be identified by PCR amplification and DNA sequencing. To confirm their authenticity, the cloned $V_L$ and $V_H$ genes can be expressed in cell culture as a chimeric Ab as described by Orlandi et al., (*Proc. Natl. Acad. Sci., USA*, 86: 3833 (1989)). Based on the V gene sequences, a humanized Class I anti-CEA MAb can then be designed and constructed as described by Leung et al. (*Mol. Immunol.*, 32: 1413 (1995)).

cDNA can be prepared from any known hybridoma line or transfected cell line producing a murine Class I anti-CEA MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)).

PCR reaction mixtures containing 10 µl of the first strand cDNA product, 10 µl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified Vκ and $V_H$ fragments can be purified on 2% agarose (BioRad, Richmond, Calif.). The humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for $V_H$ can be subcloned into a similar staging vector, such as the pBluescript-based VHpBS. Individual clones containing the respective PCR products may be sequenced by, for example, the method of Sanger et al. (*Proc. Natl. Acad. Sci., USA*, 74: 5463 (1977)).

Expression cassettes containing the Vκ and $V_H$ sequences, together with the promoter and signal peptide sequences, can be excised from VKpBR and VHpBS, respectively, by double restriction digestion as HindIII-BamHI fragments. The Vκ and $V_H$ expression cassettes can be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric, humanized or human Class I anti-CEA MAb by, for example, an ELISA assay. Alternatively, the Vκ and $V_H$ expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. (*J. Immunol. Methods* 125:191 (1989) and also shown in Losman et al., *Cancer*, 80:2660 (1997)). Another vector that is useful is the GS vector, as described in Barnes et al., *Cytotechnology* 32:109-123 (2000). Other appropriate mammalian expression systems are described in Werner et al., Arzneim.-Forsch./Drug Res. 48(11), Nr. 8, 870-880 (1998).

Co-transfection and assay for antibody secreting clones by ELISA can be carried out as follows. About 10 µg of VKpKh (light chain expression vector) and 20 µg of VHpG1g (heavy chain expression vector) can be used for the transfection of $5 \times 10^6$ SP2/0 myeloma cells by electroporation (BioRad, Richmond, Calif.) according to Co et al., *J. Immunol.*, 148: 1149 (1992). Following transfection, cells may be grown in 96-well microtiter plates in complete HSFM medium (Life Technologies, Inc., Grand Island, N.Y.) at 37° C., 5% $CO_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis. Transfectoma clones that are positive for the secretion of chimeric, humanized or human heavy chain can be identified by ELISA assay.

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2µ membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 µl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA and its concentration adjusted to about 1 mg/ml using PBS. Sodium azide, 0.01% (w/v), is conveniently added to the sample as preservative.

EXAMPLES

The invention is further illustrated by, though in no way limited to, the following examples.

Example 1

Production and Characterization of MN-15 and Other Anti-CEA Antibodies

In 1983, Primus et al. described the first panel of MAbs (NP-1, NP-2, NP-3, and NP-4) that defined NCA-cross-reactive, MA-cross-reactive, and CEA-specific epitopes on the CEA molecule (Primus et al., Cancer Res 1983, 43:686-92). NP-1 reacts with NCA (normal cross-reactive antigen), MA (meconium antigen), and CEA (carcinoembryonic antigen) and, in a liquid solution of decreasing ion strength, demonstrates increasing affinity for CEA, a property shared with unadsorbed goat anti-CEA serum and affinity-purified NCA crossreactive antibody purified from goat anti-CEA serum (Primus et al., 1983). The "ion-sensitive" determinant on CEA first was delineated by Hansen et al. (Clin Res 1971, 19:143) using unadsorbed anti-CEA polyclonal serum, and subsequently by Haskell et al. (Cancer Res 1983, 43:3857-64) with MAb. NP-2 and NP-3 react with MA and CEA but not with NCA, whereas NP-4 reacts only with CEA (Primus et al., 1983). NP-2 and NP-3 differ because NP-2 binding to CEA is blocked by NP-1, whereas NP-1 does not block binding of NP-3 to CEA. MAb reactive with NCA, MA, and CEA were designated as Class I MAb; MAb reactive with MA and CEA but unreactive with NCA were designated as Class II MAb; and MAb specific for CEA, being unreactive with NCA and MA, were designated as Class III MAb (see, e.g., U.S. Pat. No. 4,818,709, the Examples section of which is incorporated herein by reference). The present Example describes the production and characterization of a second generation of anti-CEA antibodies, including the MN-15 Class I anti-CEA MAb.

Immunization and Hybridoma Production and Screening

The immunogen used to produce MN-15 and other second generation anti-CEA antibodies was a partially purified CEA preparation derived from the GW-39 human colon adenocarcinoma xenograft (Hansen et al., 1993, Cancer 71:3478-85). Tumor was grown in the hind-leg muscle of the golden hamster, excised, frozen, and stored at −20° C. Homogenization of tumor, extraction with perchloric acid, and concentration of the dialyzed extract by ultrafiltration were performed as described previously (Newman et al., Cancer Res 1974, 34:2125-530). The concentrated extract was equilibrated by dialysis with saline adjusted to 0.05 M $NaH_2PO_4$, and chromatographed on a 5.0×90.0 cm G-200 SEPHADEX® gel column. The void peak was collected, equilibrated with saline by dialysis, and frozen at −20° C. until used. The concentration of CEA in the extract was determined with the IMMUNOMEDICS® NP-1/NP-3 and NP-1/NP-4 enzyme immunoassays (EIA) (Immunomedics, Inc., Morris Plains, N.J.).

The following protocol was used to immunize 20-g BALB/c female mice (Harlan, Madison, Wis.), from which the second-generation MN series of anti-CEA MAb were derived. Mice first were immunized subcutaneously with 7.5 µg of CEA in complete Freund adjuvant and then boosted subcutaneously with 7.5 µg of CEA in incomplete Freund adjuvant on day 3 and boosted intravenously with 7.5 µg of CEA in saline on days 6 and 9. On day 20, the first mouse was given 50 µg of CEA intravenously in saline; on day 23 one animal was killed, the spleen cell suspensions were prepared, and the cells were fused with murine myeloma cells SP2/O—Ag 14 with the use of polyethylene glycol and then cultured in medium containing 8-azaguanine.

Hybridoma supernatants were screened for CEA reactive antibody by the ROCHE® $^{125}$I-CEA radioimmunoassay (RIA) in 0.01 and 0.10 M $NH_4$ acetate buffer. Positive clones were recloned. The granulocyte reactivity of CEA-reactive MAb was determined by whole-blood indirect fluorescent flow cytometric analysis (Sharkey et al. Cancer Res., 1990, 50:2823-31). Two MAb with properties similar to those of NP-2 and NP-3, designated MN-2 and MN-6, were selected for additional development. A third MAb, MN-3, reacted with granulocytes but, unlike NP-1 and NP-2, did not demonstrate ion sensitivity for CEA binding; it also was selected for development.

The mouse used in the second fusion was immunized on days 1, 3, 6, and 9, as described above. It was given 65 µg of CEA in saline intravenously on day 278 and 90 µg of CEA in saline on day 404. It was killed on day 407. The fusion and screening protocols were the same as those used for the first mouse. The second fusion yielded one clone (MN-14) that had properties consistent with those of NP-4 in that it was unreactive with granulocytes, bound only 30-40% of $^{125}$I-CEA in the ROCHE® CEA RIA, and demonstrated no ion sensitivity of CEA binding in the RIA. A second clone producing a granulocyte-reactive antibody with properties identical to those of NP-1, MN-15, also was derived from this fusion.

MAb-IgG Purification/Characterization

The MAb were purified from ascites fluid raised in CD2F1 mice (Charles River Laboratories, Wilmington, Mass.) by protein A and ion-exchange column chromatography at 4° C. All of the MAb were of the IgG1 isotype with kappa light chains, as determined by double gel diffusion.

Enzyme Immunoassay

The reagents, formulation, standards, and assay protocol of the sandwich EIA used in these studies have been described elsewhere (Hansen et al., Clin Chem 1989, 35:146-51). All assays were performed with microwells coated with NP-1, except in one experiment, in which microwells were coated with MN-15. All assays were performed in a sequential mode, with addition of CEA first, incubation, washing of the wells, and addition of the MAb-horseradish peroxidase probe. After the second incubation, the amount of probe bound to CEA was determined by washing out the unbound probe, adding substrate (o-phenylenediamine/hydrogen peroxide), adding acid to stop the reaction, and quantitating the color product by reading the adsorbance at 490 nm. Horseradish peroxidase was conjugated to MAb NP-4, MN-3, MN-6, and MN-14, as described previously for NP-3 (Hansen et al., Clin Chem 1989, 35:146-51). All conjugates were diluted to match the dose-response curve established previously with the NP-3-horseradish peroxidase probe. Probes made with NP-4, MN-3, MN-6, and MN-14 all gave linear dose-response curves with the GW-39 CEA standard.

MA Standard

Meconium was homogenized in 10 volumes of deionized water and the mixture centrifuged at 40,000×g for 30 minutes. The supernatant was decanted from the pellet and stored at −20° C. The amount of MA plus CEA (in ng/ml) in the MA standard was determined by assay with the NP-1/NP-3 EIA. The amount of CEA (in ng/ml) in the MA standard was determined with the NP-1/NP-4 assay and found to be 15% of the total MA/CEA activity determined with the NP-1/NP-3 EIA.

Blocking Studies

Blocking studies were performed with the same conditions described for quantification of CEA. To assess blocking of binding of the enzyme probes, microwells were charged with CEA by use of 25 ng/ml of the CEA standard. Unlabeled MAb were added to MAb-enzyme conjugates, and the EIA assay was completed as described for quantitation of CEA with the NP-3 probe.

Tissue Reactivity

Immunoreactivity with blood lymphocytes was determined by live-cell indirect immunofluorescence, with the use of the whole blood staining method developed for use with the ORTHO SPECTRUM® I11 flow cytometer (Ortho Diagnostic Systems, Inc., Raritan, N.J.). Tissue reactivity of the MAb was determined by immunohistologic examination performed on frozen sections and 5-μm sections cut from tissue embedded in Paraplast-II. Indirect immunofluorescence on frozen sections was performed as previously described, with MAb concentrations of 20 μg/ml (Pawlak-Byczkowska et al., Cancer Res 1989, 49:4568-77). Immunoperoxidase staining of sections was performed with the avidin-biotin horseradish peroxidase complex method (Vector Laboratories, Burlingame, Calif.) according to the protocol suggested by the manufacturer, with MAb concentrations of 10 μg/ml.

Animal Studies

For radiolocalization studies, at 4-5 weeks female athymic mice (nu/nu; Harlan, Indianapolis, Ind.) were given subcutaneous injections of 0.2 ml of a 10% suspension of GW-39, prepared from the tumor serially propagated in athymic mice. After 2 weeks, the mice were given intravenous injections of approximately 1 μg of $^{131}$I-labeled NP-4 or MN-14. The animals were killed 7 and 14 days later; the organs were removed and radioactivity in the organs determined as described previously (Sharkey et al., Cancer Res 1990, 50:828s-34s).

Results

MAb MN-3 and MN-6 reacted with MA, whereas MN-14 did not detect MA. All of the MAb-horseradish peroxidase probes were titrated with NP-1-coated microwells charged with 25 ng/ml of CEA to obtain an absorbance of 0.6-0.8. Microwells coated with MN-15 yielded results identical to those from microwells coated with NP-1. CEA and MA standards were sent as coded specimens to commercial laboratories performing the respective commercial assays. It was expected that the ROCHE® CEA EIA would be specific for CEA because the ROCHE® assay uses MAb T86.44, a MAb that reacts with CEA but not with MA (Neumaier et al., J Immunol 1985, 135:3604-09). Both the HYBRITECH® and ABBOTT® commercial CEA EIA demonstrated cross-reactivity with MA (not shown).

The affinity of radioiodinated MN-14 for CEA was 10 times that of NP-4 as determined by adding increasing amounts of CEA to fixed amounts of MAb and determining free versus bound antibody by high pressure liquid chromatography sizing gel analysis. The 100 ng/ml of radioactive antibody used in this study to determine the affinity of the MAb approximates the serum concentration of antibody present in blood after infusion of 1 μg of antibody. Between 1 and 2 μg/ml of CEA was required to complex 50% of NP-4, with 50% complexation of MN-14 being obtained with approximately 0.2 μg/ml of CEA (results not shown).

The normal tissue reactivity of NP-4 and MN-14 was found to be identical, with both being unreactive with blood granulocytes, spleen, normal liver, and all other normal tissues except the colon (not shown). Staining of normal colon with both MAb was localized to the glycocalyx of the epithelial cells (not shown). Staining of sections of colorectal carcinoma from 10 different patients and of one lung carcinoma demonstrated identical staining patterns with the two MAb, but more intense staining was observed consistently with MN-14 (not shown).

Results of immunoperoxidase staining of spleen sections with MN-2 and MN-3, performed on frozen sections and sections prepared by conventional tissue processing (fixed in formaldehyde solution and embedded in Paraplast) were determined. The granulocyte antigen reactive with MN-3 (spleen sections) was stained in sections fixed in formaldehyde solution and embedded in Paraplast, whereas the antigen reactive with MN-2 was not detected in granulocytes in the section fixed in formaldehyde solution and embedded in Paraplast (not shown). By contrast, MN-2 strongly stained CEA present in the section of colon carcinoma fixed in formaldehyde solution and embedded in Paraplast (not shown). The pattern of MN-2 staining was similar to that observed with MN-3 and MN-14. Although blocking studies cannot prove that two MAb are reactive with the same epitope, failure to bock provides evidence of reactivity with separate epitopes.

To evaluate cross-blocking of NP-4 by MN-14, microwells coated with NP-1 were incubated with 25 μg of CEA, with reagents described above. The microwells then were washed and the NP-4-horseradish peroxidase probe added, with and without 50 μg/ml of MN-14. After incubation, the supernatants in the wells were decanted, the wells were washed, and the assay was completed. Binding of the NP-4 probe was inhibited by greater than 50%. No blocking of binding of the NP-3 probe was demonstrated under similar experimental conditions. Blocking of binding of the NP-3 probe was evaluated with the same protocol used above for NP-4. Both MN-3 and MN-6 blocked binding of the NP-3 probe to CEA.

NP-1 and MN-15 appeared to have similar properties, demonstrating high granulocyte reactivity, binding to epitopes of the ion-sensitive CEA determinant, and rapidly effecting capture of CEA from solution when coated on microwells (not shown). NP-2 and MN-2 bind to the ion-sensitive determinant but differ from NP-1 in having much lower reactivity with blood granulocytes and reacting with a granulocyte antigen that was destroyed by conventional tissue processing used in histologic examination (not shown). MN-3 reacted strongly with granulocytes but did not react with the ion-sensitive determinant (not shown). It also reacted with CEA bound to NP-1, whereas NP-2 demonstrated cross-blocking by NP-1 (not shown). NP-3, MN-6, NP-4, and MN-14 were not reactive with granulocytes or the ion sensitive determinant (not shown). NP-3 and MN-6 reacted with MA, whereas NP-4 and MN-14 were not reactive with MA (not shown).

Several tumor localization studies have been performed to compare the effectiveness of radioiodinated NP-4 with that of MN-14, with superior targeting being demonstrated for MN-14 in two studies and equivalent targeting demonstrated in a third study (not shown). Twenty animals were injected for each time point for each of the antibodies. As was observed, MN-14, as compared with NP-4, provided significantly improved tumor uptake at both 7 and 14 days after injection (P<0.02 and P<0.001, respectively). The uptake of the two antibodies in normal organs or blood was not significantly different (not shown).

Discussion

MN-14 meets all of the criteria of a Class III anti-CEA MAb, being unreactive with MA by EIA and not staining normal tissues, with the exception of normal colon. This study adds support to the suggestion that a lack of reactivity with MA is the single most useful parameter for selecting Class III anti-CEA MAb. Blocking experiments alone can be misleading in the classification of CEA MAb, as is apparent from the extensive data published from the International Workshop on epitope reactivity of MAb reactive with CEA (Hammarstrom et al., Cancer Res 1989, 49:4852-58). Although blocking experiments placed a number of Class III MAb into the Gold Group 1 (T84.66,II-16, 11-7, II-10), CEA 66, which is strongly reactive with MA and reacts weakly with NCA, cross-blocked CEA binding of a Class III MAb, 11-16. MAb B7.8.5, also placed in Gold Group 1, blocked binding of 11-16 yet reacts with NCA. Thus, the Gold Group 1, constructed on the basis of cross-blocking of binding of MAb to CEA, contains Class I, II, and III MAb.

The affinity of MN-14 is approximately 10-fold greater than that of NP-4, when determined with radioiodinated MAb and identical assay conditions to determine free versus antigen-bound antibody. The affinity determined for NP-4 in this study was significantly lower than reported previously with $^{125}$I-CEA in place of radiolabeled NP-4 (Primus et al., 1983). MN-14, like NP-4 and T86.44, binds less than 50% of radioiodinated CEA. In the case of T86.44, the low binding of $^{125}$I has been ascribed to damage of the T86.44-reactive epitope by radioiodination. If radioiodination results in damage to the NP-4-reactive epitope, unlabeled CEA would displace NP-4 more effectively, resulting in a falsely elevated affinity constant. For this reason, we elected to compare the affinity of NP-4 and MN-14 by a direct binding method using radioiodinated antibody, rather than by competitive blocking of binding of $^{125}$I-CEA to antibody.

This study also confirms the findings of Bormer et al. (Clin Chem 1991, 37:1736-39), that the T84.66 MAb, used as a probe in the commercial ROCHE® CEA EIA, is unreactive with MA, whereas commercial ABBOTT® and HYBRITECH® CEA EIA use MAb that react equally with MA and CEA. Experiments in athymic mice bearing human colon cancer xenografts have demonstrated consistently improved targeting with MN-14 compared with NP-4 (not shown). The results of targeting with NP-4 are highly variable between experiments, however; and it has not been possible to conclude whether the superior targeting resulted from increased binding or longer retention of the antibody in the tumor, as suggested by the data presented herein.

Four of the MN MAb have been evaluated by clinical radioscintigraphy studies. MN-3 strongly targets bone marrow granulocytes and is being investigated for radioimmunodetection of occult infection and inflammation. MN-2 and MN-6 demonstrated similar deficiencies in radioimmunodetection of CEA-containing cancers, as observed for NP-2 and NP-3. $^{131}$I-MN-2 targeted bone marrow, and $^{131}$I-MN-6 accreted in the lumen of the normal colon (unpublished results). Excellent specificity and sensitivity were demonstrated with $^{131}$I-MN-14 in a Phase I clinical study to detect CEA containing tumors by radioimmunodetection, and results of this study have been described (Sharkey et al., Cancer 1993, 71:2082-96).

Conclusions

A second-generation panel of anti-carcinoembryonic antigen (anti-CEA) monoclonal antibodies (MAb) has been generated, and the specificity has been compared with that of the first panel of MAb used to differentiate meconium antigen (MA) from CEA.

Four of the MAb had similar specificities to the first-generation panel of NP MAb. MN-15, like its first-generation equivalent, NP-1, reacted with normal cross-reactive antigen (NCA), MA, and CEA. Both MN-15 and NP-1 reacted strongly with granulocytes. MN-2 had properties similar to Class II NP-2, being reactive with MA and CEA, cross-blocking binding to CEA by NP-1, and having low reactivity with granulocytes. Both NP-2 and MN-2 stained granulocytes in frozen tissue sections but showed minimal staining of granulocytes in sections fixed in formaldehyde solution and embedded in Paraplast. MN-14 demonstrated properties similar to the Class III anti-CEA-specific MAb, NP-4, being unreactive with NCA and MA. MN-14, as compared with NP-4, demonstrated significantly superior tumor targeting in a human colon tumor xenograft model and consistently stronger staining of frozen sections of colon cancer. A fifth MAb, MN-3, had properties uniquely different from the NP series of MAb, reacting strongly with granulocytes but not demonstrating the liquid-phase ion-sensitivity binding of CEA exhibited by MN-15 and NP-1.

Example 2

Production of Chimeric and Humanized MN-15 Antibodies

To make a chimeric MN-15 antibody, the murine MN-15 variable region sequences were attached to human IgG1 constant region sequences, as described in Leung et al., Hybridoma 13:469 (1994). The sequences of the murine MN-15 $V_K$ (SEQ ID NO:9) and MN-15 $V_H$ (SEQ ID NO:10) used to construct the chimeric MN-15 (cMN-15) are shown in FIG. 2 and FIG. 3. FIG. 1 shows the results of a competitive binding study of murine vs. chimeric MN-15, competing with horseradish peroxidase (HRP) labeled murine MN-15. FIG. 1 demonstrates that the cMN-15 construct has an affinity for CEA that is virtually identical to the parent murine MN-15 antibody, with a dissociation constant in the nanomolar range. As expected, the MN-3 (amino terminal) and MN-14 (A3-B3) antibodies, which bind to different epitopes of CEA than MN-15 (A1B1) did not compete for binding with HRP-labeled murine MN-15.

To humanize the MN-15 antibody, human variable FRs were selected based on sequence homology with their murine counterparts. The greatest homology was found with the human KOL $V_H$ and REI $V_K$ FRs. Oligonucleotides encoding murine MN-15 CDRs were grafted onto these heavy and light chain variable region domains, respectively. The MN-15 CDR sequences included light chain CDR1 (SASSRVSYIH, SEQ ID NO:1); CDR2 (GTSTLAS, SEQ ID NO:2); and CDR3 (QQWSYNPPT, SEQ ID NO:3); and heavy chain variable CDR1 (DYYMS, SEQ ID NO:4); CDR2 (FIANKANGHTTDYSPSVKG, SEQ ID NO:5); and CDR3 (DMGIRWNFDV, SEQ ID NO:6). The humanized variable region genes were cloned into expression vectors along side human IgG1 constant region genes according to Orlandi et al., Proc. Nat'l Acad. Sci. USA 86: 3833 (1989).

Certain murine FR amino acid residues were substituted into the KOL and REI FR region sequences. Specifically, heavy chain amino acid residues 28, 29, 30, 48 and 49 and light chain amino acid residues 21, 47 and 60 of the murine MN-15 antibody were substituted into the human FR sequences by standard mutagenesis techniques (Sambrook et al., Molecular Cloning, A laboratory manual, $2^{nd}$ Ed (1989)). The resulting hMN-15 $V_K$ (SEQ ID NO:7) and $V_H$ (SEQ ID NO:8) amino acid sequences are shown in FIG. 2 and FIG. 3. The murine MN-15 FR region amino acids that were retained in the hMN-15 sequences are indicated by underlining in the hMN-15 sequences. CDR sequences are bolded and boxed.

Figure 4:
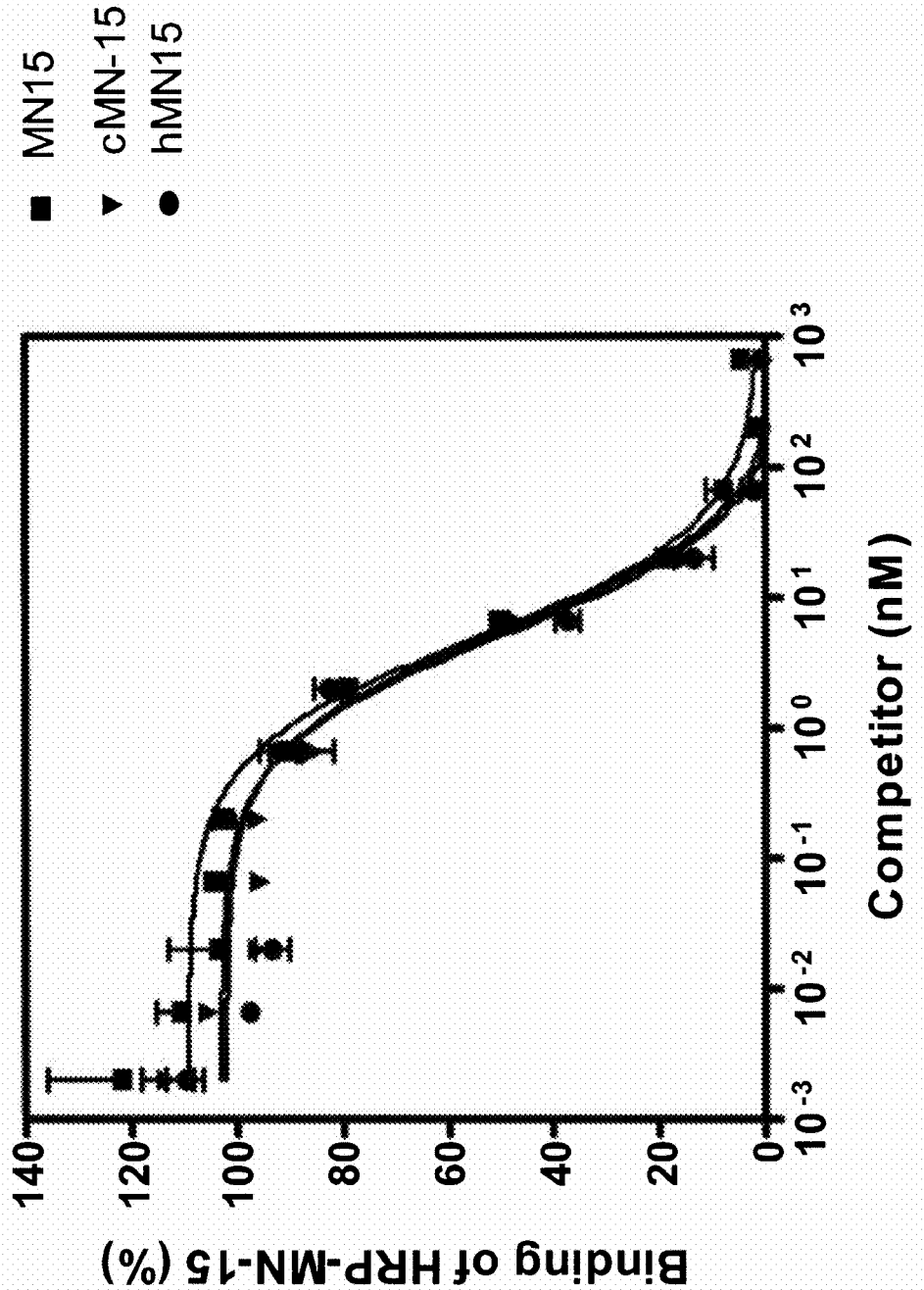
FIG. 4 illustrates an exemplary comparative CEA binding curve for humanized MN-15 (hMN-15) vs. the parental murine MN-15 antibody.

FIG. 4 shows a comparison of the binding affinities of murine, chimeric and humanized MN-15, in competition with HRP-labeled murine MN-15. As shown in FIG. 4, the cMN-15 and hMN-15 constructs have virtually identical binding affinities for CEA with the parental murine MN-15 antibody, with dissociation constants in the nanomolar range.

Expression vector DNAs may be transfected into SP2/0 by electroporation. Transfectomas secreting the various versions of chimeric or humanized MN-15 are selected and analyzed. For large-scale production, the cell line is grown in a 16-liter stirred tank bioreactor system (Sulzer-Chemtech, Woodbury, N.Y.). The culture medium is continuously harvested from the bioreactor through a 0.2 μm tangential flow microfiltration hollow fiber unit. The filtered harvest is collected continuously into a 50-liter reservoir, stored at 4° C., from which the medium stream is pumped to a protein-A column to collect the antibody from the product stream. The harvested antibody is purified by a second pass through a protein-A column and, finally, Q-Sepharose (Pharmacia, Inc., Piscatway, N.J.). The final product purity is assessed by SDS-PAGE, immunoelectrophoresis, HPLC, and immunoreactivity.

Example 3

Inhibition of Adhesion, Invasion and Metastasis by Antibodies Targeting CEACAM6 (NCA-90) and CEACAM5 (CEA)

Summary

CEACAM5 and CEACAM6 are overexpressed in many cancers and are associated with adhesion and invasion. The effects of three monoclonal antibodies targeting different epitopes on these antigens ($NH_2$-terminal [MN-3] and A1B1 domains [MN-15] shared by CEACAM5 and CEACAM6 and the A3B3 domain [MN-14] restricted to CEACAM5) were evaluated in migration, invasion, and adhesion assays in vitro using a panel of human pancreatic, breast, and colonic cancer cell lines, and in the GW-39 human colonic micrometastasis model in vivo. MN-3 Fab' and MN-15 Fab' were both effective at inhibiting cell migration. MN-15 Fab' treatment inhibited invasion, reducing cell penetration through an extracellular matrix (ECM). MN-3 Fab' also decreased invasion but was less effective than MN-15 Fab' in four of five cell lines. All three monoclonal antibody Fabs decreased adhesion of tumor cells to endothelial cells by 49% to 58%. MN-15 Fab' but not MN-3 or MN-14 Fabs induced a decrease in adhesion of three of six cell lines to the ECM protein, fibronectin, but adhesion to vitronectin, laminin, collagen-I, and collagen-IV was not affected. In vivo studies showed that treatment with MN-3 Fab' or MN-15 Fab' of mice implanted with GW-39 human colonic cancer cells increased their survival (P<0.025 and P<0.01, respectively). These studies show that antibody Fabs that target either CEACAM5 or CEACAM6 affect cell migration, cell invasion, and cell adhesion in vitro, and that MN-15 and MN-3 Fabs have antimetastatic effects in vivo, resulting in improved survival of mice with metastases. Thus, blocking the N and A1B1 domains of CEACAM5/CEACAM6 can impede the metastatic process.

Background

The eradication of metastatic disease is crucial for achieving survival in most patients with cancer. The metastatic process consists of a series of sequential steps, including invasion of extracellular matrix (ECM), extravasation into vessels, transport in the circulation, adhesion to endothelial cells in a new tissue, extravasation through the vessel wall, and migration and proliferation in response to organ-specific factors at the new site (Fidler, Cancer Res 1990, 50:6130-8). The present Example deals with the development of an antibody-based therapeutic approach to impede metastasis.

Carcinoembryonic antigen (CEA, CEACAM5, and CD66e) is expressed on many cancers (Goldenberg et al., J Natl Cancer Inst 1976, 57:11-22; Gold & Goldenberg, McGill J Med 1997, 3:46-66; Hammarstrom, Semin Cancer Biol 1999, 9:67-81) and has been implicated with malignancy, particularly enhanced metastasis (Yoshioka et al., Jpn J Cancer Res 1998, 89:177-85; Hashino et al., Clin Exp Metastasis 1994, 12:324-28). CEACAM5 functions as a chemoattractant and as an adhesion molecule (Kim et al., Int J Cancer 1999, 82:880-85), and has been reported to promote the metastatic potential in some experimental tumors (Minami et al., Cancer Res 2001, 61:2732-5). CEACAM5 has been shown to be involved in both homophilic (CEACAM5 to CEACAM5) binding between the N domains of antiparallel CEACAM5 molecules on opposite cell surfaces and heterophilic binding (CEACAM5 binding to non-CEACAM5 molecules). Ribozyme-mediated suppression of CEACAM5 expression reduces metastases in a nude mouse tail vein injection model (Wirth et al., Clin Exp Metastasis 2002, 19:155-60), whereas anti-CEACAM5 intact MAb, MN-14, also delayed death due to metastasis in a human colorectal cancer model (Blumenthal et al., Cancer Immuno Immunother 2005, 54:315-27) and reduced growth of the TT human medullary thyroid cancer xenograft (Stein & Goldenberg, Mol Cancer Ther 2005, 3:1559-64).

Nonspecific cross-reacting antigen (NCA-90, CEACAM6, and CD66c) is a member of the CEA family that is also expressed on many human cancers (Kuroki et al., Anticancer Res 1999, 19:5599-606). CEACAM6 in tumors correlates inversely with cellular differentiation (Ilantzis et al., Neoplasia 2002, 4:151-63) and is an independent prognostic factor associated with a higher risk of colorectal cancer relapse (Jantscheff et al., J Clin Oncol 2003, 21:3638-46). CEACAM6 is also an important protein associated with cell adhesion; its expression on neutrophils is involved in adhesion to cytokine-activated endothelial cells (Kuijpers et al., J Cell Biol 1992, 118:457-66). This molecule exhibits homotypic and heterotypic interactions with other members of the CEA family and with integrin receptors. Antibodies targeting the N domain interfere with cell-cell interactions (Yamanka et al., Biochem Biophys Res Commun 1996, 219:842-7). Normal cells routinely undergo apoptosis in the absence of adhesive interactions with ECM, a phenomenon known as "anoikis" (Frisch et al., J Cell Biol 1994, 124:616-26). Resistance to anoikis, a characteristic of tumor cells, facilitates tumorigenesis and metastasis. CEACAM5 and CEACAM6 both inhibit anoikis and modulation of CEACAM6 expression alters the malignant phenotype of cancer cells (Duxbury et al., Oncogene 2004). Silencing the CEACAM6 gene by small interfering RNA enhances cell anoikis, increases caspase activation in response to anchorage-independent conditions, down-regulates the Akt cell survival pathway, and inhibits metastasis in vivo (Duxbury et al., Cancer Res 2004, 64:3987-93). Expression of this membrane protein is also associated with increased invasiveness through a c-src-dependent mechanism (Duxbury et al., Br J Cancer 2004, 91:1384-90). Thus, CEACAM6 may represent a therapeutic target to control malignancy and/or metastasis.

Antigenic sites on CEACAM5 and CEACAM6 have been characterized, and panels of antibodies recognizing specific epitopes have been generated (Audette et al., Mol Immunol 1987, 24:1177-86; Bjerner et al., Tumour Biol 2002, 23:249-62). Three subdomains in the N region that are required for intercellular homotypic adhesion have been identified by site-directed deletions and point mutations (Taheri et al., J Biol Chem 2000, 275:26935-43). Binding peptides have been developed to these regions in an effort to block adhesion (Taheri et al., J Biol Chem 2003, 278:14632-9). The concentration of peptide required to block cell aggregation was 1 mg/mL or a 25-fold higher molar concentration than the complete antibody, despite the predicted greater penetration of a smaller peptide. This inefficient dose requirement could be due to instability of the small peptide or due to its low affinity. We postulated that using monovalent antibody fragments would be a more effective approach for targeting these domains, because stability of the MAb will likely be greater and the affinity higher than corresponding peptides. Our studies have primarily been done with monovalent fragments of the antibodies of interest, rather than intact IgGs, because the single binding arm of the Fab will prevent complexation of tumor cells, which might occur with a bivalent IgG. In addition, it allowed us to study the efficacy of a CEA/NCA-90-targeted antibody without the potential effector cell-inducing activity of the Fc region. We have assessed the expression of CEACAM5 and CEACAM6 on a panel of tumor cell lines and have determined the effects of several antibodies targeting different epitopes of CEACAM5 and CEACAM6 for their ability to affect tumor cell migration, invasion, and cell adhesion in vitro. We have also evaluated the therapeutic potential of these antibody Fabs in controlling metastasis and survival of mice bearing a CEACAM5/CEACAM6-expressing human colonic carcinoma.

Materials and Methods

Figure 5:
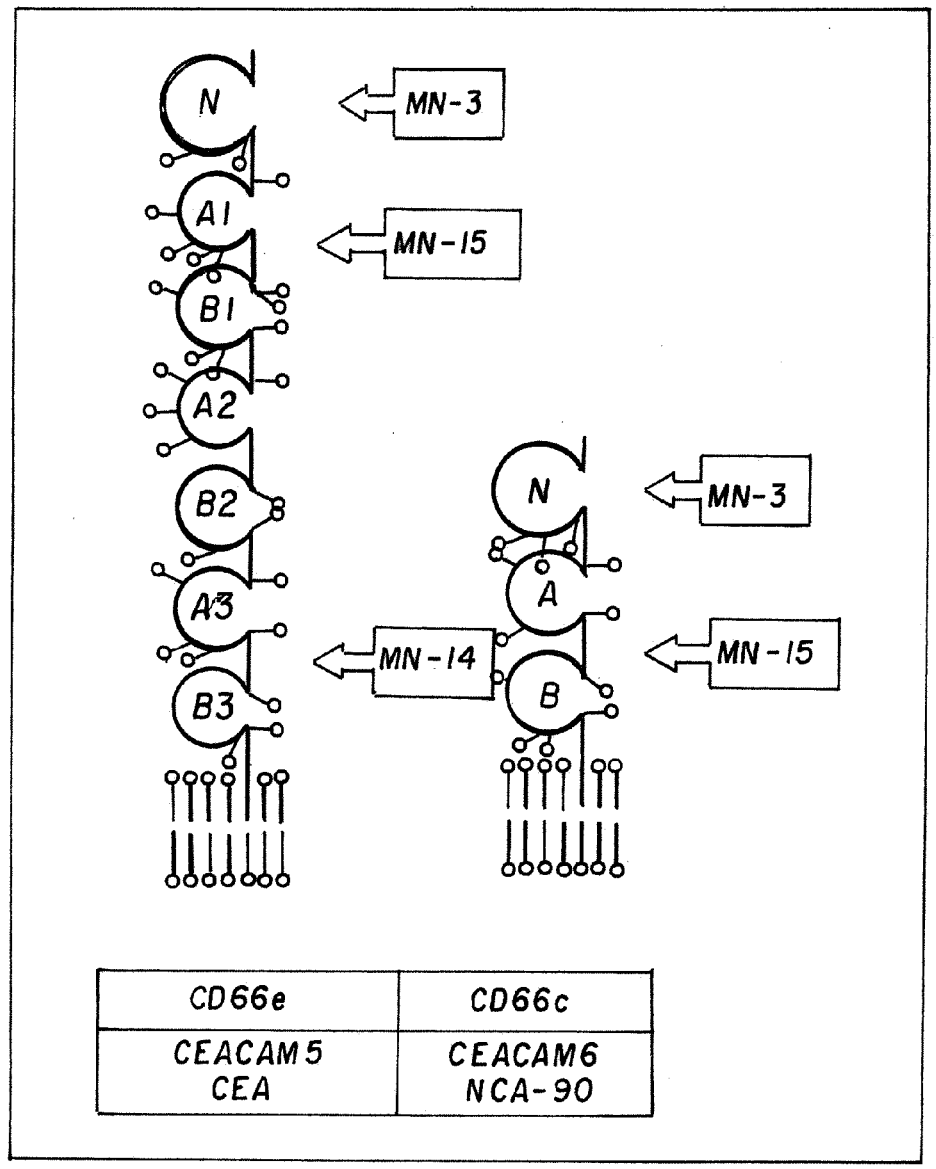
FIG. 5 shows a schematic structural drawing of the domains of CEACAM5 (left) and CEACAM 6 (right). The epitopes recognized by MN-15, MN-3 and MN-14 antibodies on CEACAM5 and CEACAM6 are as noted.

Antibody production—MN-15 binds to the A1B1 domain (Gold group 4) and MN-3 binds to the N domain (Gold group 5) found on both CEACAM5 and CEACAM6, while MN-14 binds to the A3B3 domain (Gold group 3) only found on CEACAM5 (FIG. 5). MN-3 and MN-15 were used as murine MAbs, whereas MN-14 was included in its humanized form, hMN-14 or labetuzumab (Sharkey et al., Cancer Res 1995, 55:5935-44).

Cell culture—All cell lines were maintained in monolayer culture having RPMI 1640 supplemented with 10% fetal bovine serum (FBS) plus 100 units/mL penicillin, 100 units/mL streptomycin, 4 mmol/L glutamine, and 1% nonessential amino acids and grown at 37° C. in 95% air and 5% $CO_2$. Cells were harvested using 1% trypsin and counted by hemocytometer. Viability was determined by trypan blue exclusion.

CEACAM5 and CEACAM6 expression—Cells were harvested from culture and aliquoted into FACSCAN™ tubes containing 2 mL Dulbecco's PBS with 0.2% sodium azide and 1% appropriate blocking serum. Cells were incubated with 10 µg/mL of hMN-14 anti-CEACAM5 in PBS (+$NaN_3$+ 1% blocking serum) for 1 hour on ice, pelleted (1,440 rpm×5 minutes), and supernatant decanted. Some tubes were then incubated with 10 µg/mL murine MN-15 IgG or MN-3 IgG (to determine CEACAM6 expression) for 1 hour on ice and pelleted. Neither MN-15 nor MN-3 bind CEACAM5 once MN-14 is bound so that only CEACAM6 was detected by MN-15 or MN-3 in the presence of MN-14. Second antibody conjugated with FITC (FITC-goat-anti-human for CEACAM5 determination and FITC-goat-anti-mouse for CEACAM6 determination) was added (1:500 secondary antibody in PBS+$NaN_3$+1% blocking serum) for 30 minutes on ice in the dark. Cells were pelleted, washed twice with 2 mL ice-cold PBS+$NaN_3$, and resuspended in 1.5% paraformaldehyde. Fluorescence was read on a flow cytometer. Percentage of cells that were positive and mean channel fluorescence (MCF) were recorded. CEACAM5 and CEACAM6 expression on GW-39 tumor xenografts was determined by immunohistochemistry using a similar approach of hMN-14 followed by biotinylated GAH to detect CEACAM5 and preincubation with hMN-14 followed by mMN-15 or mMN-3 and biotinylated GAM second antibody to detect CEACAM6 on paraffin sections.

Spontaneous migration assay—Glass coverslips were placed in 100×15 mm Petri dishes and UV sterilized overnight. Suspensions of cancer cells (2-4×$10^5$ cells/mL) were prepared from 80% to 90% confluent monolayers. Cells were plated on each coverslip and incubated for 2 to 5 days to reach 70% to 80% confluence. Two diagonal cell-free paths ("wounds") were created by dragging a sterile yellow pipette tip across the surface. Monolayers were rinsed several times to remove floating cells and 4 mL of fresh medium were added back in the absence or presence of antibody IgG or Fab' (10 µg/mL) and incubated at 37° C. After 18 to 24 hours, the medium was removed and coverslips stained with 1 mL Wright-Giemsa for 1 minute. The stain was washed off with distilled water, air-dried, and mounted onto slides with Cytoseal 60. Repopulation of the wound space was evaluated by counting the number of cells that migrated into the wound area in 10 representative fields. Regions of migration were photographed for documentation.

Endothelial cell adhesion assay—Human umbilical vein endothelial cells (HUVEC; Cambrex, San Diego, Calif.) were grown in collagen-coated dishes in EGM Media in a humidified atmosphere with 5% $CO_2$ at 37° C. At passages 2 to 5, cells were plated at a density of 4×$10^4$ cells per well in 96-well plates 24 hours before the assay. Interleukin-1B (IL-1B, 1 ng/mL) was added 4 hours before the assay. At the start of the study, the medium with the IL-1B was removed and fresh DMEM with 1% bovine serum albumin (BSA) added and incubated for 30 minutes. Fresh medium without antibodies or with 10 µg/mL of MN-15 Fab', MN-3 Fab', or Ag8 Fab' was added. Tumor cells (1×$10^6$ cells/mL) prelabeled overnight with $^3$H-thymidine (100 µL per well using 1.0 µCi/mL) were added to HUVEC cultures and incubated for 30 minutes at 37° C. with rotation in medium with 20% FBS. Samples were washed thrice with PBS to remove unattached cells. Attached cells were solubilized with 0.1 N NaOH and radioactivity was measured in a β scintillation counter. The cpm attached/total cpm added (attaching potential) was determined.

Adhesion to extracellular matrix proteins assay—The assay was done using the CYTOMATRIX™ screening kit from CHEMICON® (Kit #ECM205, Temecula, Calif.). The kit contains 96-well plates with strips coated with fibronectin, vitronectin, laminin, collagen-I, or collagen-IV. Subconfluent cell cultures were used for these studies. Cells (1×$10^6$ cells/mL) were seeded onto coated substrate and incubated at 37° C. for 1 hour in a $CO_2$ incubator in PBS containing $Ca^{2+}/Mg^{2+}$ (200 µL per well). Adherent cells were fixed and stained. The plate was washed to remove unadhered cells and stained with 100 µL per well of MTS (Cell Titer Aq 96, PROMEGA®, Madison, Wis.) for 5 minutes at room temperature. Excess stain was removed with three PBS washes. Solubilization buffer [100 µL of a 50:50 mixture of 0.1 mol/L $NaH_2PO_4$ (pH 4.5) and 50% ethanol] was added to each well. Relative attachment was determined using absorbance readings ($A_{540\,nm}$-$A_{570\,nm}$).

Collagen-based invasion assay—The assay was done using CHEMICON® Kit (#ECM551, MILLIPORE®, Billerica, Mass.). Tumor cells at 80% confluence and were serum-starved for 18 to 24 hours before the assay was used. Cells were harvested with 5 mL of 2 mmol/L EDTA/PBS per 100-mm dish and incubated at 37° C. for 5 to 15 minutes. Cells were collected into 10 to 20 mL of quenching medium (serum-free DMEM containing 5% BSA) to inactivate trypsin/EDTA from the harvesting buffer. Cells were pelleted, resuspended in quenching medium ($1\times10^6$ cells/mL), and appropriate antibody Fabs were added to individual cell aliquots. Cell invasion potential was determined as follows. Baseline invasion and invasion in the presence of a chemoattractant (10% FBS) were measured after a 72-hour incubation period at 37° C. in a 5% $CO_2$ incubator. The bottom side of the collagen-coated polycarbonate membrane insert of the invasion chamber was placed in 400 μL of cell stain for 20 minutes at room temperature and washed. The dye was extracted and transferred into a 96-well microtiter plate for colorimetric measurements ($A_{560\ nm}$).

In vivo therapy studies—Female athymic nude mice (6 to 8 weeks old) were purchased from TACONIC® (Germantown, N.Y.). Therapy studies were done using our CEACAM5+/CEACAM6+GW-39 intrapulmonary micrometastasis model, GW-39iv (Sharkey et al., J Natl Cancer Inst 1991, 83:627-32; Blumenthal et al., Cancer Res 1992, 52:6036-44). The GW-39 human colonic carcinoma has been maintained as a serially transplanted signet-ring cell cancer line since 1966 (Goldenberg et al., Transplantation 1966, 4:760-4). Stock s.c. GW-39 tumors grown in nude mice were used to prepare a 10% cell suspension. Cells (30 μL) were injected i.v. into the caudal vein of 5- to 6-week-old female nude mice. This results in ~50 to 100 tumor nodules developing in the lungs and a median survival time of 7 to 9 weeks. Cells were pretreated with antibody in vitro (10 μg/mL) before implantation, and then mice were given one additional dose (100 μg per mouse i.v.) 1 day after implantation. Body weight was monitored weekly and animal survival recorded. Results were analyzed by the Kaplan-Meier estimated survival curves, and significance was determined with the log-rank comparison of survival curves. Median survival time for each treatment group also was determined. All studies used 10 mice per treatment group. Results CEACAM5 and CEACAM6 expression in cell lines—Flow cytometric analysis of CEACAM5 and CEACAM6 expression in a panel of 31 to 33 commonly used solid tumor cell lines revealed that only 6 of 29 (20.7%) expressed significant amounts of CEACAM5, whereas 16 of 30 (53.3%) lines were positive for CEACAM6 (Table 1). Two cancer cell lines were CEACAM5+/CEACAM6− (Moser and LNCAP), four were CEACAM5+/CEACAM6+, and 12 were CEACAM5−/CEANCAM6+. The CEACAM6+ cell lines included 7 of 10 breast cancers, one of four ovarian cancers, three of four colon cancers, three of four pancreatic cancers, one of six prostate cancers, and two of four non-small cell lung cancer lines. Many of these tumor lines had >95% of cells expressing the CEACAM6 antigen and, in some cases, expression was very high (MCF of 641 for ZR75-30, 702 for BXPC3, and 476 for CaPAN-1). In contrast, the most positive CEACAM5-expressing lines had <60% of cells expressing the antigen, with a MCF <120.

TABLE 1

Number of Tissue Cores Analyzed for Each Histotype.

| Tumor | Histotype | N | Tumor | Histotype | N |
|---|---|---|---|---|---|
| Breast | Infiltrating Ductal | 30 | Colon | Adeno carcinoma | 41 |
| | Papillary | 8 | Pancreas | Well Diff | 1 |
| | Lobular | 4 | | Well-Mod Diff | 16 |
| | Phyllodes | 4 | | Mod Diff | 2 |
| Lung | Well Diff Adeno | 5 | | Mod-Poorly Diff | 6 |
| | Mod Diff Adeno | 5 | | Poorly Diff | 1 |
| | Poorly Diff Adeno | 5 | Ovary | Serous Adeno | 5 |
| | Well Diff Squamous | 5 | | Mucinous Adeno | 4 |
| | Mod Diff Squamous | 5 | | Clear Cell | 5 |
| | Poorly Diif Squamous | 5 | | Transitional Cell | 5 |
| | | | | Endometroid | 4 |
| | Bronchioalveolar | 3 | | Brenner | 4 |
| | Large-Cell | 2 | | Yolk Sac | 3 |
| | Neuroendocrine | | | Granulosa | 3 |
| | Large-Cell | 3 | | Dysgerminoma | 3 |
| | Small-Cell | 2 | | | |
| Prostate | Stage II | 21 | | | |
| | Stage III | 15 | | | |
| | Stage IV | 4 | | | |

Effect of anti-CEACAM5 and anti-CEACAM6 antibodies on cell migration—Using the wound-healing assay, we assessed cell migratory activity in vitro in a panel of cell lines. LS174T and HT-29 cells showed the most migratory activity, whereas ZR75-30, MCF-7, and BXPC3 cells showed very little migration (results not shown). Compared with an irrelevant antibody, MN-3 and MN-15 intact IgG and Fab' all reduced migration in both cell lines. In HT-29, the number of migrating cells per field decreased from 14.9±9.1 to 6.1±0.9 and 3.7±1.6 cells with MN-3 IgG and Fab', respectively, and to 5.5±1.8 and 5.4±0.8 with MN-15 IgG and Fab', respectively ($P<0.01$ for all comparisons of MAb treatment with untreated cells; n=10 for each arm). In LS174T studies, untreated cells had 38.8±10.9 migrating cells per field, whereas cells treated with MN-3 IgG or Fab' had 21.4±5.2 and 18.1±1.6 migrating cells, respectively ($P<0.001$ versus untreated), and cells treated with MN-15 IgG or Fab' had 20.3±0.1 and 21.6±1.2 migrating cells, respectively ($P<0.001$ versus untreated). Thus, blocking either the N or A1B1 domain of CEACAM6 with either an intact IgG or a monovalent Fab inhibited migration in vitro.

Figure 6:
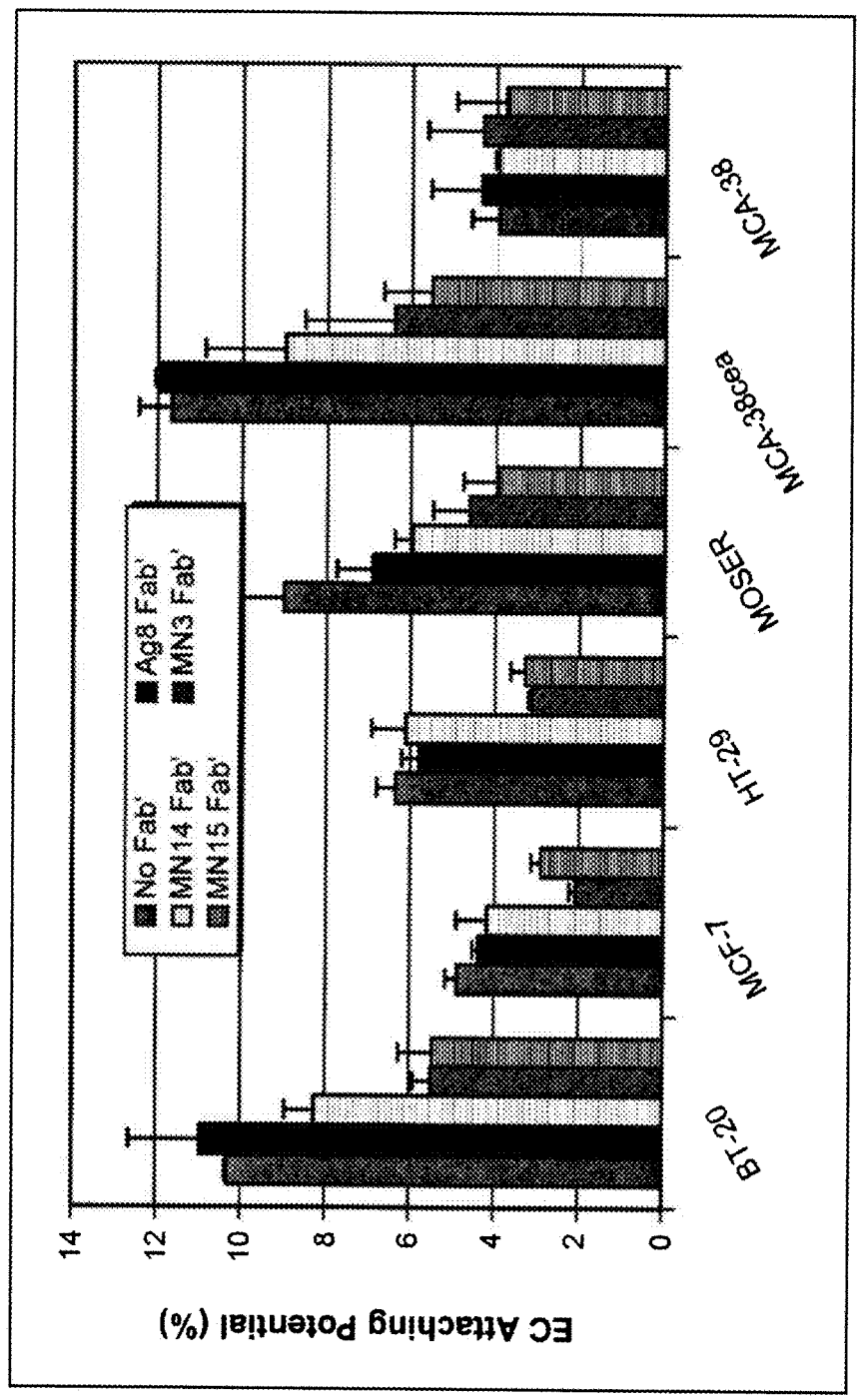
FIG. 6 shows the results of an in vitro endothelial cell adhesion assay. Percentage adhesion of various tumor cells with varying amounts of expressed CEACAM5 and CEACAM6 to HUVEC cells in the absence or presence of MN-15 Fab', MN-3 Fab', or Ag8 Fab' control. Cells were labeled with 1 µCi/mL of $^3$H-thymidine and added to HUVEC cultures and incubated for 30 minutes at 37° C. Samples were washed thrice with PBS to remove unattached cells. Attached tumor cells were solubilized with 0.1 N NaOH and radioactivity was measured in a β-scintillation counter. The cpm attached/total cpm added (attaching potential) was determined. Results of a typical study are presented. Cell lines used include BT-20 (CEACAM5+/CEACAM6+), MCF-7 (CEACAM5−/CEACAM6+), HT-29 (CEACAM5−/CEACAM6+), Moser (CEACAM5+/CEACAM6−), MCA38cea (CEACAM5+/CEACAM6−), and MCA38 (CEACAM5−/CEACAM6−). Both MN-15 and MN-3 induced a 49% to 58% inhibition in adhesion in four cell lines (P<0.01 for MN-3 Fab' on MCF-7, HT-29, and BT-20; P<0.02 for MN-15 on the same three lines; and P<0.05 for both Fabs on Moser adhesion to endothelial cells).

Effect of MN-15 and MN-3 on tumor cell adhesion to endothelial cells—Because both CEACAM5 and CEACAM6 are known to have an adhesion role, we evaluated whether blocking these antigens reduces adhesion to endothelial cells (FIG. 6). In the CEACAM5−/CEACAM6−MCA38 murine colonic cancer line, neither MN-3 Fab' targeting the N domain nor MN-15 Fab' targeting the A1B1 domain of CEACAM6 had an effect on tumor cell-endothelial cell adhesion (not shown). In contrast, both antibodies reduced endothelial cell binding of MCA38cea (a human CEA-transfected line) from 11.68±0.77% to 6.42±2.1% (MN-3) and 5.53±1.15% (MN-15), being significant ($P<0.05$) for both Fabs (FIG. 6). Both antibodies induced a 49% to 58% adhesion-inhibition in four other cell lines ($P<0.01$ for MN-3 Fab' on MCF-7, HT-29, and BT-20; $P<0.02$ for MN-15 on the same three lines; and $P<0.05$ for both Fabs on Moser cell adhesion to endothelial cells, FIG. 6). An isotype-matched irrelevant antibody Fab' (Ag8) did not affect tumor cell-endothelial cell adhesion nor did the MN-14 anti-CEA Fab'. The magnitude of the anti-adhesion effect did not seem strictly correlated with the amount of CEACAM5 or CEACAM6 expressed, because MN-15 Fab' resulted in a greater decrease in adhesion in HT-29 cells (48%) than with MCF-7 cells (41%) that express much more CEACAM6.

Effect of anti-CEACAM5 and anti-CEACAM6 antibodies on tumor cell adhesion to extracellular matrix proteins—In addition to tumor cell binding to endothelial cells, these cells can also bind ECM proteins. The extent of tumor cell binding to ECM proteins varies among different cell lines. MCF-7 bound well to four of five proteins ($A_{560\ nm}$>1.1) except laminin ($A_{560\ nm}$=0.2±0.04), whereas ZR75-30 attached weakly to all five ECM proteins evaluated ($A_{560}$ nm<0.45). MDA-468 bound quite well to collagen-I and collagen-IV ($A_{560\ nm}$=1.25±0.07 and 0.97±0.03, respectively) but not as well to fibronectin, vitronectin, or laminin. The reverse pattern was seen with CaPAN-1 ($A_{560\ nm}$=1.78±0.21 for fibronectin, 0.88±0.11 for vitronectin, 1.14±0.09 for laminin, 0.07±0.00 for collagen-I, and 0.13±0.08 for collagen-IV). None of the antibodies (IgG or Fab') modulated adhesion to vitronectin, laminin, collagen-I, or collagen-IV (results not shown). However, MN-15 IgG decreased adhesion of MCF-7, MDA-468, and CaPAN-1 to fibronectin by 29% (P<0.01), 51% (P<0.001), and 47% (P<0.02), respectively, while not affecting the binding of ZR75-30, BXPC3, or Moser to fibronectin. Two of these three MAb-unresponsive cell lines had the lowest baseline adhesion to fibronectin.

Effect of MN-3, MN-15, and MN-14 Fabs on tumor cell invasion—Specific invasion in response to FBS as a chemoattractant was 1.9-fold (LS174T) to 7.4-fold (BXPC3) higher than in the absence of FBS (not shown). MN-15 Fab' was more effective than MN-3 Fab' at reducing tumor cell invasion in vitro in five cell lines that expressed CEACAM5, CEACAM6, or both antigens. MN-14 anti-CEA (CEACAM5) had no effect on tumor cell invasion in most cell lines. MDA-231 expresses neither antigen, and its invasion was not reduced by either MN-3 or MN-15 IgG or Fab'. For the five antigen-positive lines, both the intact IgG and the monovalent Fab' for a given antibody were equally effective. For example, MN-15 Fab' reduced cell invasion of LS174T, MCF-7, ZR75-30, BXPC3, and CaPAN-1 cells by 30% (P<0.02), 77% (P<0.01), 49% (P<0.01), 44% (P<0.01), and 73% (P<0.002), respectively. The effect of MN-3 Fab' on the same five lines was a reduction in invasion of 3% (P=NS), 47% (P<0.01), 59% (P<0.01), 0% (P=NS), and 55% (P<0.05), respectively. Thus, the A1B1 domain of CEACAM6 seems to be a more important target than the N domain for the process of tumor cell invasion.

Figure 7:
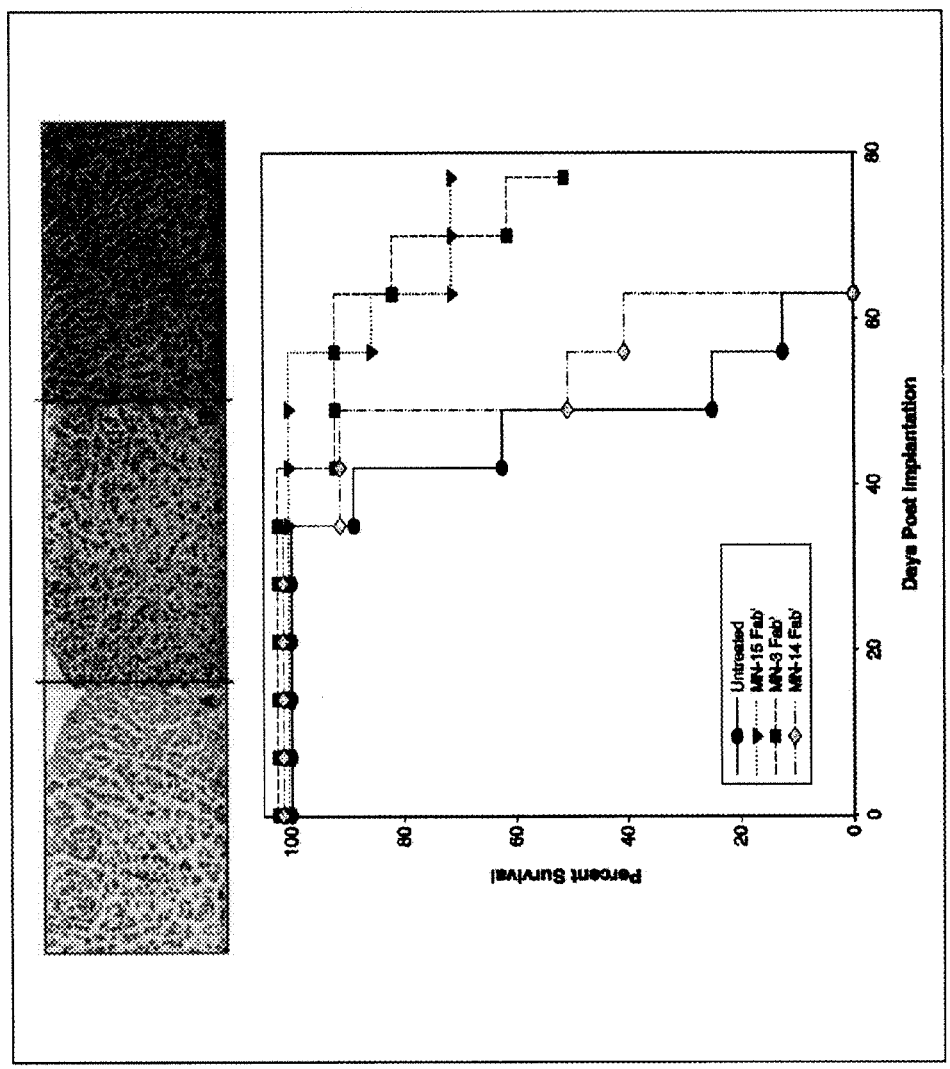
FIG. 7 illustrates an exemplary in vivo micrometastasis study. Top, immunohistochemistry of GW-39 tumor sections stained with a nonspecific antibody (A), MN-14 anti-CEACAM5 (B), and MN-15 anti-CEACAM6 (C) and photographed at 100×. Bottom, survival of nude mice implanted with 30 µL of a 10% suspension of GW-39 human colonic cancer cells. Mice were implanted with cells that were preincubated for 30 minutes with MN-3-, MN-15-, or hMN-14-

Effect of MN-3, MN-15, and MN-14 Fab' on survival of mice bearing GW-39 intrapulmonary colonic micrometastases—GW-39 expresses both CEACAM5 and CEACAM6, as shown by immunohistochemistry (FIG. 7, top). Based on the in vitro results suggesting that anti-CEACAM6 antibodies had limited antiproliferative effects yet showed significant anti-invasive and anti-adhesive properties, we pretreated GW-39 tumor cell suspensions with each of the antibody fragments (10 µg/mL) for 15 minutes before i.v. injection of 30 µL of cells and then dosed with 100 µg of antibody on the day after transplantation. This design simulates the effect of a continuous exposure to antibody that would be available at any time that a cell from a primary tumor might initiate the metastatic cascade. The results presented in FIG. 7 illustrate that both MN-15 and MN-3 Fabs increased median survival time (>77 and 77 days, respectively; P<0.001 versus untreated cells) of these mice, whereas hMN-14 Fab' (49 days) did not affect survival significantly (42 days for untreated mice). Although the study was continued until mice were near death, rather than sacrificing them at a defined time after treatment and counting the number of lung nodules, median survival time should correlate with amount of lung metastatic disease. The results with hMN-14 Fab' in this study are similar to what we reported for hMN-14 F(ab)$_2$ in this metastatic model (Blumenthal et al., Cancer Immuno Immunother 2005, 54:315-27), indicating that targeting the A3B3 domain does not affect median survival in this model, whereas targeting the N and A1B1 domains shared by CEACAM5 and CEACAM6 did affect metastasis and host survival when the respective Fabs are given.

Discussion

A long-term goal of immunotherapy has been to induce antitumor responses against tumor-related antigens. Antibodies that directly perturb signaling mechanisms have shown clinical benefit, such as those directed against the extracellular domains of HER-2/neu, epidermal growth factor receptor, and CD20 (Weiner & Adams, Oncogene 2000, 19:6144-51; Alas et al., Cancer Res 2001, 61:5137-44). The studies presented herein suggest that instead of being directly therapeutic by immune effector or direct cytostatic mechanisms, MAbs against CEACAM6 inhibit migration, invasion, and adhesion, thereby limiting metastasis. The monovalent Fab' form was used for most of our studies to avoid effector cell function from the Fc region of the MAb and focus on mechanisms implicated in the metastatic process.

CEACAM5 is overexpressed in a majority of carcinomas, including those of the gastrointestinal, respiratory and genitourinary systems, and the breast. Our results show that another CEA family member, CEACAM6, may be as good, if not better, as a target for solid tumor antimetastatic therapy. We have shown that CEACAM6 is expressed in a larger percentage of solid tumor cell lines than CEACAM5, and the high MCF on many of these lines suggests that more anti-CEACAM6 MAb can be delivered to these tumor cells. Thus, the MN-15 and MN-3 MAbs are useful for tumors that express CEACAM6 or CEACAM5, because they target epitopes that are shared by both antigens. These MAbs may therefore have advantages over MAbs like MN-14, which only target CEACAM5, or MAbs that are specific for only CEACAM6 and do not cross-react with CEACAM5. Our data are consistent with previous reports that showed a relatively high level of CEACAM6 in the sera of a large number of lung, liver, pancreatic, breast, and colorectal cancer patients (Kuroki et al., Anticancer Res 1999, 19:5599-606). Interestingly, some patients were CEACAM5−/CEACAM6+, further suggesting that CEACAM6 might be a useful independent target.

It is known that CEACAM6 is expressed on the surface of neutrophils, thus modulating adherence to endothelial-leukocyte adhesion molecule-1 on activated endothelial cells (Kuijpers et al., J Cell Biol 1992, 118:457-66). We have shown that MAbs to different epitopes on CEACAM6 (N and A1B1 domains) affect cell adhesion with endothelial cells. There is also evidence that CEACAM5 can affect cell adhesion to endothelial cells (Gangopadhyay et al. Clin Exp Metastasis 1998, 16:703-12) via activation of Kupffer cells and stimulation of IL-1β, tumor necrosis factor-α, and IL-6 production. These cytokines then induce the expression of intercellular adhesion molecules on endothelial cells, thus increasing adhesion of tumor cells to endothelium. Our results have shown that MN-3 and MN-15 Fab's are more active than MN-14 Fab' at reducing adhesion of CEACAM5+/CEACAM6+ tumor cells to endothelial cells. Thus, both the N and the A1B1 domains but not the A3B3 domain are involved in tumor cell to endothelial cell adhesion.

Tumor cells can adhere to other tumor cells, to endothelial cells, as well as to ECM proteins. We have found that the amount of adhesion to a panel of these proteins varied between cell lines and was not related to the type of tumor (e.g., breast and pancreatic) or to the amount of CEACAM5 or CEACAM6 expressed. Tumor cell interactions with ECM proteins are important for migration and invasion and therefore metastasis. For example, tumor cell interactions with fibronectin are involved in the development of secondary tumors inside the bone marrow stroma via the (15131 integrin (Van der Velde-Zimmermann et al., Exp Cell Res 1997, 230: 111-20). Blocking adhesion with polypeptide fragments of heparin-binding domains of fibronectin inhibited metastasis (Matsumoto et al., Jpn J Cancer Res 1991, 82:1130-8). Similar results have been obtained with a peptide blocking tumor cell-laminin adhesion (Islam et al., Surgery 1993, 113:676-82). Surprisingly, only MN-15 (A1B1 domain) was able to reduce adhesion to fibronectin in three of six tumor cell lines tested. The percent inhibition in fibronectin adhesion in this panel of cell lines did not correlate with the amount of adhesion in untreated cell samples. MAbs targeting the N or A3B3 domain did not affect cell adhesion to fibronectin. In one report by Duxbury et al. (J Biol Chem 2004, 279:23176-82), MAb-mediated CEACAM6 cross-linking resulted in increased ECM adhesion. However, the targeted epitope was different from the ones studied here.

Active migration of tumor cells is a prerequisite of tumor cell invasion and metastasis. Adhesion molecules that increase invasion also enhance the migratory process (Hazan et al., J Cell Biol 2000, 148:779-90). Overexpression of CEACAM6 has been reported to promote cellular invasiveness of pancreatic cancer (Duxbury et al., Oncogene 2004, 23:465-73). Agents that inhibit metastases often affect several steps including migration, adhesion, and invasion. Because our data suggest that CEACAM6 has a role in adhesion and invasion, it is important to also assess the ability of these MAbs to impede migration. We have shown that in cell lines with strong migratory tendencies, MAb blocking of CEACAM5 and/or CEACAM6, with MN-3>MN-15, decreases the number of migrating cells. In our in vitro assay, the process of cell invasion, which involves adhesion to ECM and migration steps, was inhibited by MN-15 Fab'>MN-3 Fab', suggesting that the A1B1 domain of CEACAM6 is more important for this step but that the N domain also plays a role.

One of the notable advantages of MN-15 or MN-3 MAb therapy, compared with our previously reported results with MN-14 anti-CEA IgG (Blumenthal et al., Cancer Immunol Immunother 2005, 54:315-27), is the ability to target tumors that express either CEACAM6, CEACAM5, or both, whereas MN-14 can only be used for CEACAM5+ tumors. As shown in Table 1, many solid tumor lines express CEACAM6 but not CEACAM5 or express more CEACAM6 than CEACAM5. These tumor types are candidates for metastasis-directed MAb therapy with CEACAM6 MAbs.

An important consideration based on the in vivo experiments is the availability of MAb when cells first enter the circulation. MN-15 Fab' and MN-3 Fab' showed therapeutic efficacy if cells were exposed to MAb before the initiation of the metastatic process. However, if MAb was delivered after cancer cells had exited the vasculature and had begun to seed in the lung, MAbs alone were not therapeutic (data not shown). Therefore, in certain preferred embodiments, anti-CEACAM5/CEACAM6 MAbs would be available continuously, perhaps using implantable pumps, to maintain a desired level in the circulation.

Overall, the anti-metastasis and MAb inhibition of adhesion, invasion, and migration is a technology that should be relatively nontoxic, not limited by issues of drug resistance, and easy to apply as an adjuvant with other standard and/or experimental therapy approaches. Because CEACAM6 is also expressed in normal lung, spleen, and granulocytes (Grunert et al., Int J Cancer 1995, 63:349-55), the effect of anti-CEACAM6 MAb on normal tissues is one consideration for therapeutic use. In one report, CEACAM6-targeted immunotoxin therapy was effective in a tumor-bearing nude mouse model (Duxbury et al., Biochem Biophys Res Commun 2004, 317:837-43), but this model does not express CEACAM6 on normal tissues.

In summary, we have shown that anti-CEACAM6/CEACAM5 MAb fragments devoid of effector cell functions and targeting the N and A1B1 domains of these antigens block migration, adhesion to endothelial cells and ECM, and invasion, and also increase the median survival of mice with intrapulmonary micrometastases of human colonic cancer. These results indicate that antibodies against CEACAM5 and CEACAM6, such as MN-15, may be efficacious in human cancer therapy.

Example 4

Expression Patterns of CEACAM5 and CEACAM6 in Primary and Metastatic Cancers

Summary

Many breast, pancreatic, colonic and non-small-cell lung carcinoma lines express CEACAM6 (NCA-90) and CEACAM5 (carcinoembryonic antigen, CEA), and antibodies to both can affect tumor cell growth in vitro and in vivo. Here, we compare both antigens as a function of histological phenotype in breast, pancreatic, lung, ovarian, and prostatic cancers, including patient-matched normal, primary tumor, and metastatic breast and colonic cancer specimens.

Antigen expression was determined by immunohistochemistry (IHC) using tissue microarrays with MN-15 and MN-3 antibodies targeting the A1B1- and N-domains of CEACAM6, respectively, and the MN-14 antibody targeting the A3B3 domain of CEACAM5. IHC was performed using avidin-biotin-diaminobenzide staining. The average score ±SD (0=negative/8=highest) for each histotype was recorded.

For all tumors, the amount of CEACAM6 expressed was greater than that of CEACAM5, and reflected tumor histotype. In breast tumors, CEACAM6 was highest in papillary>infiltrating ductal>lobular>phyllodes; in pancreatic tumors, moderately-differentiated>well-differentiated>poorly-differentiated tumors; mucinous ovarian adenocarcinomas had almost 3-fold more CEACAM6 than serous ovarian adenocarcinomas; lung adenocarcinomas>squamous tumors; and liver metastases of colonic carcinoma>primary tumors=lymph nodes metastases>normal intestine. However, CEACAM6 expression was similar in prostate cancer and normal tissues. The amount of CEACAM6 in metastatic colon tumors found in liver was higher than in many primary colon tumors. In contrast, CEACAM6 immunostaining of lymph node metastases from breast, colon, or lung tumors was similar to the primary tumor.

CEACAM6 expression is elevated in many solid tumors, but variable as a function of histotype. Based on previous work demonstrating a role for CEACAM6 in tumor cell migration, invasion and adhesion, and formation of distant metastases (Blumenthal et al., Cancer Res 65: 8809-8817, 2005), it may be an important target for antibody-based therapy.

Background

The human carcinoembryonic antigen (CEA) family has 7 genes belonging to the CEACAM subgroup. These subgroup members are mainly associated with the cell membrane and show a complex expression pattern in normal and cancerous tissues. The CEACAM5 gene, also known as CD66e, codes for the protein, CEA (Beauchemin et al., *Exp Cell Res.* 1999, 252:243-249). CEACAM5 was first described in 1965 as a gastrointestinal oncofetal antigen (Gold & Freedman, *J Exp Med.* 1965,122:467-481), but is now known to be overexpressed in a majority of carcinomas, including those of the gastrointestinal tract, the respiratory and genitourinary systems, and breast cancer (Goldenberg et al., *J Natl Cancer Inst.* 1976, 57:11-22; Shively et al., *Crit Rev Oncol Hematol.* 1985, 2:355-399; Hammarstrom, *Semin Cancer Biol.* 1999, 9:67-81). CEACAM6 (also called CD66c or NCA-90) is a non-specific cross-reacting glycoprotein antigen that shares some antigenic determinants with CEACAM5 (Kuroki et al., *Biochem Biophys Res Comm.* 1992, 182:501-506). CEACAM6 also is expressed on granulocytes and epithelia from various organs, and has a broader expression zone in proliferating cells of hyperplastic colonic polyps and adenomas, compared with normal mucosa (Scholzel et al., *Am J Pathol.* 2000, 157:1051-1052), as well as by many human cancers (Kuroki et al., *Anticancer Res.* 1999, 19:5599-5606; Hinoda et al. *J Gastroenterol.* 1997, 32:200-205). Relatively high serum levels of CEACAM6 are found in patients with lung, pancreatic, breast, colorectal, and hepatocellular carcinomas. The amount of CEACAM6 does not correlate with the amount of CEACAM5 expressed (Kuroki et al., *Anticancer Res.* 1999, 19:5599-5606).

Expression of CEACAM6 in colorectal cancer correlates inversely with cellular differentiation (Ilantzis et al., *Neoplasia.* 2002, 4:151-163) and is an independent prognostic factor associated with a higher risk of relapse (Jantscheff et al., *J Clin Oncol.* 2003, 21:3638-3646). Both CEACAM5 and CEACAM6 have a role in cell adhesion, invasion and metastasis, as discussed in Example 3. The present study used tissue microarray analysis to compare the relative expression of CEACAM5 and CEACAM6 in different histotypes of solid tumors, and compared expression between primary sites and matched metastases in the same patients.

Methods

Antibodies—As discussed above, MN-15 binds to the A1B1-domain and MN-3 binds to the N-domain found on both CEACAM5 and CEACAM6. MN-14 binds to the A3B3 domain only found on CEACAM5. These antibodies have similar affinities for their target antigens (Hansen et al., *Cancer.* 1993, 71:3478-3485). MN-3 and MN-15 were used as murine MAbs, while MN-14 was included in its humanized form, hMN-14 (labetuzumab).

Tissue microarrays—ACCUMAX™ tissue arrays were from ISU ABXIS® (Seoul, Korea). The following arrays were used: Breast A202 (II), colon with matching liver metastases A203 (II), lung A206, pancreatic A207, prostate A208, and ovary A213. Additional breast BR1001, colorectal C0991, and lung LC810 arrays of matching primary tumor and lymph node metastases were purchased from US Biomax, Inc. (Rockville, Md.). All arrays consisted of duplicate cancer tissue cores of varying histotypes and four non-neoplastic corresponding samples on each slide. There were 45 breast, 40 lung, 26 pancreatic, 40 prostate, and 45 ovarian cancer specimens. Some histotypes are well represented (e.g., 30 infiltrating ductal breast tumors), while others had only 3-6 cores per histotype. The metastasis arrays consisted of the following matched cases: 18 normal colon, primary colon cancer and liver metastases, 38 breast and lymph node metastases, 33 colon and lymph node metastases, and 37 lung and lymph node metastases.

Immunohistochemistry—Slides were deparaffinized in xylene, rehydrated, and treated with fresh 0.3% hydrogen peroxide in methanol for 15 min. Following a wash in 1× phosphate-buffered saline (PBS, pH 7.4), slides were blocked with normal serum in a humid chamber for 20 min at room temperature (RT). Excess serum was rinsed off with 1×PBS and slides were incubated in a humid chamber with 25-50 µl of primary antibody (10 µg/ml) for 45 min at RT. For CEACAM5 staining, the primary antibody was murine mMN-14 IgG. For CEACAM6 staining, slides were first blocked with humanized hMN-14 IgG and then incubated with primary antibody, either murine mMN-15 or mMN-3 IgG. Excess primary antibody was washed off and sections were covered with biotinylated goat-anti-mouse for 30 min in a humid chamber at RT. Slides were then flooded with 0.3% $H_2O_2$ in methanol and 25 µl avidin-horseradish peroxidase (HRP) conjugate was added. Slides were incubated for 45 min at RT, washed in 1×PBS, and covered with 100 µl 3,3'-diaminobenzidine tetrahydrochloride solution (100 mg/ml diaminobenzide in 0.1 M sodium acetate buffer, pH 6.0, with 0.01% (v/v) $H_2O_2$) for 15 min. Slides were washed twice by dipping in tap water and counterstained with 4 quick dips in hematoxylin (filtered through WHATMAN® #4 filter paper). Slides were rinsed, air-dried, and mounted with 1-2 drops of cytoseal and a glass coverslip. The method of Kawai was used to calculate a semi-quantitative score from 0 to 8 for staining of each tissue core (Kawai et al., *Clin Cancer Res.* 2005, 11:5084-5089). The number of positive cells/file was estimated and assigned a number: 0=none, 1=1/100 cells, 2=1/100 to 1/10 cells, 3=1/10 to 1/3 cells, 4=1/3 to 2/3 cells, and 5=>2/3 cells. The intensity of staining was then determined where 0=none, 1=weak, 2=intermediate, and 3=strong. The first and second scores were then added together resulting in a maximum staining score of 8 for any tissue core. Two independent blinded investigators performed IHC analysis and results were strongly consistent between the two readings. Results were recorded as the mean±standard deviation for each group. Comparisons between CEACM5 and CEACAM6 scores for a given histotype or between histotypes for each antigen were assessed by a one-factor analysis of variance with the use of a two-tailed F test and a 95% confidence limit. The null hypothesis Ho: $\mu1=\mu2=\frac{1}{4} \mu k$, where k equals the number of experimental groups, was used. A two-tailed test takes into account an extreme value in any one group that deviates from the population mean in either the high or low direction (two-sided). The F value is a measure of the probability that this difference in groups could occur by chance alone.

Results

Expression in solid tumors as a function of histotype—For all tumor cores evaluated, the amount of CEACAM6 was greater than that of CEACAM5. However, the homogeneity of expression and staining intensity varied between tissue histotypes and between samples within the same histological type. We evaluated 45 breast tumor cores: 30 infiltrating ductal carcinoma, 8 papillary, 4 lobular, and 3 phyllodes. CEACAM6 levels were higher than CEACAM5 levels for all histotypes (P<0.001). The highest CEACAM6 expression was found in papillary (6.0±2.1)>infiltrating ductal (5.1± 2.5)>lobular (4.0±0.8)>phyllodes (2.0±1.0). The differences between papillary and lobular breast cancers were significant at the P<0.01 level. The highest CEACAM5 expression was found in papillary samples (1.4±1.4), but was not statistically different from infiltrating ductal or lobular samples. Pyllodes breast cancer is a stromal tumor, usually benign, and should therefore not express CEACAM5 or CEACAM6.

CEACAM5 and CEACAM6 expression was assessed in 6 different lung cancers: 5 each of well, moderately and poorly differentiated adenocarcinoma, 5 each of well, moderately and poorly differentiated squamous carcinoma, 3 each of large cell and bronchioalveolar, and 2 each of large cell neuroendocrine and small cell cancer. Among these, adenocarcinoma expressed more CEACAM6 than squamous cancer (P<0.001). The highest CEACAM6 expression was found in moderately-differentiated adenocarcinoma (7.8±0.4)>well-differentiated adenocarcinoma (7.3±1.1)=bronchioalveolar (7.2±0.8)>poorly-differentiated adenocarcinoma (6.8±1.0)>small-cell (5.5±0.7)>well-differentiated squamous (5.2±1.0)>moderately-differentiated squamous cancer (4.9±1.1). CEACAM6 levels in large-cell (4.5±0.9) and poorly-differentiated squamous carcinomas (3.8±1.3) were similar to non-neoplastic lung tissue (P=NS), suggesting that anti-CEACAM6 antibodies would not be effective with these histotypes of lung cancer. The highest expression of CEACAM5 was in small-cell lung cancer specimens (5.5±0.7), followed by large-cell neuroendocrine tumors (4.75±3.18). Large-cell tumors were CEA-negative and all adenocarcinomas and serous tumors scored<2.60.

Pancreatic cancer has been the most extensively studied neoplasm with respect to CEACAM6 expression. We evaluated CEACAM5 and CEACAM6 in pancreatic cancer as a function of tumor cell differentiation. One well-differentiated, 3 well-moderately differentiated, 13 moderately-differentiated, 2 moderately- to poorly-differentiated, and 7 poorly-differentiated tumor cores were studied. The highest expression of CEACAM6 in pancreatic tumors was found in moderately-(7.5±0.7)>moderately-poor (5.9±1.9)=well-moderately differentiated (5.8±1.8)>poorly-differentiated tumors (5.1±2.5)>well-differentiated (4.0±0.0) adenocarcinomas (P=NS between the subtypes). Non-neoplastic pancreas CEACAM6 expression was 2.25±0.5. The well-moderately, moderately, and moderately-poor adenocarcinomas were significantly higher than non-neoplastic pancreas (P<0.001). CEACAM6 expression did not correlate with disease stage. Samples with high (8) and low (3-4) expression could be found in stages IA-IB, IIA-IIB, and IV. CEACAM5 expression was lower than CEACAM6 for all histotypes; the highest expression being found in moderately differentiated tumors (4.0±1.4) and the least in the moderate-poor (0.92±1.92) and poorly-differentiated (1.4±1.5) tumors. Only the moderately and the well-moderately differentiated tumors expressed significantly more CEACAM5 than non-neoplastic tissues (P<0.002 and P<0.005, respectively).

Eighteen stage-II, 15 stage-III, and 4 stage-IV prostate tumor cores were stained for CEACAM5 and CEACAM6. Gleason scores of 4 to 9 were represented in the stage-II samples, and Gleason scores of 6 to 10 were found in the stage-III specimens. All stage-IV samples were Gleason 9-10. Expression did not correlate with Gleason score of the sample within any stage. Similar expression of CEACAM6 was found in stage-II, -III, and -IV prostate cancer (3.3-3.8), and was not significantly different from non-neoplastic prostate tissue (P=NS). CEACAM5 expression was consistently below 0.9 for all stages of prostate cancer and was not greater than expression levels in non-neoplastic prostate tissue (0.5±1.0; P=NS).

Nine ovarian cancer types were studied: 5 each of serous adenocarcinoma, mucinous adenocarcinoma, clear cell carcinoma, and transitional cell carcinoma; 4 each of endometrioid adenocarcinoma and Brenner tumor; and 3 each of yolk sac tumor, granulosa cell tumor, and dysgerminoma. The amount of CEACAM6 in ovarian cancer was highest in mucinous adenocarcinoma (5.6±1.7)>transitional cell (3.8±1.6)>endometrioid (3.6±2.8)>clear cell (3.4±1.8) >yolk sac tumors (2.5±0.5). Mucinous tumor CEACAM6 expression was significantly higher than transitional and endometroid (P<0.02), clear cell (P<0.01), and yolk sac tumors (P<0.005). Much lower levels were found in serous adenocarcinoma (1.8±1.3)>Brenner tumor (1.3±1.4)=dysgerminoma (1.3±1.5)>granulosa cell (0.7±1.2). Normal ovary samples were negative for CEACAM6. Thus, all tumor histotypes expressed significantly more CEACAM6 than non-neoplastic ovary. The highest CEACAM5 expression also was found in the mucinous adenocarcinoma type (1.6±1.5). Expression of CEACAM5 in all other ovarian samples scored below 0.6, and non-neoplastic ovary scores were 0.5±1.0. Mucinous CEACAM5 levels were significantly higher than all other histotypes (P<0.002 compared with endometroid and Brenner tumors, and P<0.001 compared with serous, clear cell, transitional and yolk sac).

Much larger amounts of CEACAM6 were found in colon adenocarcinoma (6.2±1.4) compared with non-neoplastic colon (3.0±0.0; P<0.002) and CEACAM6 expression exceeded CEACAM5 expression (3.4±0.5; P<0.001).

CEACAM6 expression has been associated with cell adhesion, a key step in the metastatic cascade. We have shown above that antibody to CEACAM6 expression can block adhesion. Therefore, we assessed whether CEACAM6 expression was similar or different between matched primary colon and metastatic liver sites. In half of the matched cases (N=6), CEACAM6 expression was much greater in the liver metastasis than in the primary colon tumors, and in the remaining 6 cases, the amounts were comparable between the primary and the metastatic liver sites.

In contrast to the higher expression of CEACAM6 in many secondary liver sites from colon cancer, there was no pattern for CEACAM6 expression between primary tumor and lymph node metastases. For breast samples, the lymph node sites had higher CEACAM6 expression in 7 pairs, lower CEACAM6 in 6, and no difference in 25 pairs. For lung samples, the lymph node sites had higher CEACAM6 expression in 10 pairs, lower CEACAM6 in 11, and no difference in 16 pairs. For colon samples, the lymph node sites had higher CEACAM6 expression in 7 pairs, lower CEACAM6 in 10, and no difference in 11 pairs.

Discussion

CEACAM5 and CEACAM6 are two tumor-associated antigens that play important regulatory roles in cell adhesion and in tumor cell chemosensitivity (Glinsky, *Cancer Metastasis Rev.* 1998, 17:177-186; Kraus et al., *Oncogene.* 2002, 21:8683-8695; Zhou et al., *Cancer Res.* 1993, 53:3817-3822). CEACAM6 overexpression independently predicts poor overall survival and poor disease-free survival, whereas CEACAM5 has not been related significantly to these outcomes (Jantscheff et al., Vol. 37. Eur J Cancer, 2001, 37:S290).

Studies have shown that CEACAM5 affects expression of various groups of cancer-related genes, especially cell cycle and apoptotic genes, protecting colonic tumor cells from various apoptotic stimuli, such as treatment with 5-fluorouracil (Soeth et al., *Clin Cancer Res.* 2001, 7:2022-2030). Therefore, CEACAM5 expression may be a means for cancer cells to overcome apoptosis-inducing therapies. Ordonez et al. have reported that expression of both CEACAM5 and CEACAM6 plays a role in inhibiting apoptosis of cells when deprived of their anchorage to the extracellular matrix, a process known as anoikis (Ordonez et al., *Cancer Res.* 2000, 60:3419-3424). Increased expression of CEACAM6 correlates with a decrease in sensitivity to drugs, like gemcitabine (Duxbury et al., *Cancer Res.* 2004, 64:3987-3993). Targeting CEACAM5 and/or CEACAM6 may therefore be a novel method of modulating cancer cell chemosensitivity and apoptosis. It has been reported that siRNA to CEACAM6 impairs resistance to anoikis and increases caspase-mediated apoptosis of xenografted tumors (Duxbury et al., *Oncogene.* 2004, 23:465-473). Antibody-directed targeting of CEACAM6 may provide a clinically feasible alternative to RNA interference silencing to enhance responsiveness to chemotherapeutic agents in those tumors that express CEACAM6.

To determine which solid tumors and histological types would be most amenable to antibody blocking of CEACAM5 and CEACAM6, we studied expression of these antigens using tissue microarray analysis. To date, pancreatic and colonic cancer have been the focus of CEACAM6 expression in the literature (Duxbury et al., Ann Surg. 2005, 241:491-496; Kodera et al,. Br J Cancer. 1993, 68:130-136). Here, we have further explored the expression of CEACAM6 in a panel of solid tumors: breast, lung, ovary and prostate cancer, in addition to expanding on pancreatic and colonic tumors, and used tissue microarrays to further define tumors that are CEACAM6+ as a function of histological type in all six solid tumor categories. Our results show that expression is strongly dependent on the histotype of the tumor. Antigen expression in some subtypes is 2-4-fold higher than in normal tissues, while in others, expression is similar to non-neoplastic tissues.

The demonstration of higher CEACAM6 expression compared with CEACAM5 across most solid tumors, and the differential expression as a function of histotype, are important observations for translating anti-CEACAM6 therapy to patients. This analysis is a step towards elucidating the importance of CEACAM6 as a tumor target in a variety of solid tumors that extend the many important studies reported for pancreatic cancer (Duxbury et al., J Biol Chem. 2004, 279: 23176-23182; Duxbury et al., Cancer Res. 2004, 64:3987-3993; Duxbury et al., Biochem Biophys Res Comm. 2004, 317:837-843; Duxbury et al., Ann Surg. 2005, 241:491-496). It also reveals that expression level varies as a function of tumor histotype.

We have also addressed the expression pattern of CEACAM6 in primary tumors and in matched metastases in the same patients. Our results show that in half of the clinical specimens, liver metastases had a much higher expression of CEACAM6 than the primary colorectal tumors, suggesting that in such patients, blocking adhesion and invasion that results from CEACAM6 expression might influence the ability of tumor cells to metastasize, as we have in fact shown experimentally (Goldenberg et al., J Natl Cancer Inst. 1976, 57:11-22). However, CEACAM6 expression in lymph node metastases was similar to the amount of antigen in primary breast, colon or lung tumor samples. The mechanism by which malignant tumors invade lymphatics and metastasize to regional lymph nodes appears to be regulated by VEGF-C and VEGF-D induced lymphogenesis (Detmar & Hirakawa, J Exp Med. 2002, 196:713-718) and a chemokine gradient. Directional movement is related to chemokine receptor expression on tumor cells (Nathanson, Cancer. 2003, 98:413-423), but does not involve members of the CEACAM family. In contrast, CEACAM6 plays an important role in migration, invasion and adhesion (Duxbury et al., Oncogene. 2004, 23:465-473), steps that are important in the metastatic spread to secondary tissue sites other than lymph nodes. Anti-adhesive molecules that disrupt cell-matrix and cell-cell attachments have been proposed as potential cancer therapeutics based on their ability to interfere with motility, adhesion, and metastatic progression (Blumenthal et al., Cancer Res. 2005, 65:8809-8817; Glinsky, Cancer Metastasis Rev. 1998, 17:177-186; Kerbel et al., Bulletin de P institut Pasteur. 1995, 92:248-256).

We have reported that the humanized anti-CEA (CEACAM5) antibody, hMN-14, can enhance the therapeutic effects of two cytotoxic drugs used frequently in colorectal cancer therapy, fluorouracil and CPT-11, in both subcutaneous and metastatic human colonic tumor cells propagated in nude mice (Blumenthal et al., Cancer Immuno Immunother. 2004, 54:315-27). In another high CEA-expressing human medullary thyroid cancer xenograft, we have also shown that MN-14 anti-CEA IgG can inhibit tumor cell growth and also augment the effects of dacarbazine, a drug that is active in this cancer type (Stein et al., Mol Cancer Ther. 2004, 2:1559-1564). One explanation may involve a role in antibody blocking adhesion (Zhou et al., Cancer Res. 1993, 53:3817-3822) and thereby chemosensitizing the tumor cells.

In a series of studies, Duxbury and associates have shown that silencing CEACAM6 by siRNA: (a) enhances cell anoikis, (b) increases caspase activation in response to anchorage independent conditions, (c) downregulates the Akt cell survival pathway, (d) inhibits metastasis in vivo, and (e) enhances gemcitabine induced chemosensitivity (Duxbury et al., Cancer Res. 2004, 64:3987-3993; Duxbury et al., Oncogene. 2004, 23:465-473; Duxbury et al., Biochem Biophys Res Comm. 2004, 317:133-141; Duxbury et al., Ann Surg. 2005, 241:491-496). Thus, in addition to CEACAM5, CEACAM6 may also be a useful therapeutic target. Blocking CEACAM6-mediated homotypic and/or heterotypic adhesion may have anti-metastatic and chemosensitizing effects. In ongoing preclinical therapy studies, we are examining the therapeutic effects of unconjugated anti-CEACAM6 antibody alone or combined with standard chemotherapeutic agents in colon, breast, and lung metastasis models. An alternative approach is to develop an anti-CEACAM6 immunoconjugate as a therapeutic agent for CEACAM6+ tumors (Duxbury et al. Biochem Biophys Res Comm. 2004, 317:837-843). In vitro targeting with an anti-CEACAM6 antibody, followed by secondary saporin-conjugated immunoglobulin (IgG), induced marked cytotoxicity via caspase-mediated apoptosis. In an in vivo nude mouse xenograft model, this indirect immunotoxin approach markedly suppressed pancreatic adenocarcinoma tumor growth and enhanced tumor apoptosis.

Conclusion

Based on expression level, CEACAM6 may be a more promising target for antibody-based anti-metastatic and chemosensitizing therapy than CEACAM5 in the solid tumors studied. Furthermore, CEACAM6 may be a useful antigen to target in select subtypes of solid tumors. In colonic cancer, CEACAM6 may play an important role in the development of distant metastases.

Example 5

In Vivo Effect of Pretreatment with an Immunomodulator Prior to Treatment with hMN-15 and CPT-11 on Tumor Cell Chemosensitivity The effect of combined treatment of hMN-15 with CPT-11 is evaluated, initiated together in mice with GW-39 tumors expressing higher CEA levels, as a result of pretreatment of GW-39 stock tumors (10% GW-39 cell suspension) with interferon-γ (IFNγ). The experiments involving interferon-gamma enhancing the antitumor effects of naked CEA antibody (hMN-15) are conducted as follows.

GW-39 human colon cancer is grown subcutaneously in a mouse that receives 100,000 units of IFN-gamma twice a day for 4 days. A control mouse with GW-39 tumor is not given IFN. Experimental mice are injected i.v. with a 5% suspension of GW-39 (w/v) from either of the two mice (i.e., with or without IFN treatment) into two groups of eight. Four of each receive tumor from the IFN-treated mice and four from the untreated mice. One group of 8 mice then receive hMN-15 (100 µg per day×14 days and then twice weekly thereafter until experiment is ended), another group receive CPT-11 at 160 µg/day×5 days (=20% of maximum tolerated dose), a third group receives the same doses of antibody+drug combined, and a fourth group is not treated at all. Animal weights are measured and survival determined weekly. Also, samples of stock tumor treated with IFN in the mice that are later implanted are also processed for immunohistology to assess increase in CEA expression in the tumors from mice treated with IFN-gamma, and this is controlled by also treating the suspensions by immunohistology with an irrelevant IgG, such as Ag8, which shows no CEA staining It is observed that IFNγ pretreatment increases the expression of CEA in GW-39 tumors. The combination of naked hMN-15 with CPT-11 is more effective at reducing tumor growth and increasing survival than the sum of the effects of either therapeutic agent alone. This effect is more pronounced in the tumors pretreated with IFNγ.

Example 6

Sigmoid Colon Cancer Therapy with Anti-CEA Antibody and GM-CSF

JR is a 62-year-old man who is refractory to chemotherapy with 5-fluorouracil and leucovorin to reduce his metastases to the liver found at the time of removal of his sigmoid colon cancer. His plasma titer of carcinoembryonic antigen (CEA) at presentation is 34 ng/mL, and computed tomography of the liver shows several small lesions measuring between 2 and 4 cm in diameter in the right lobe. Other radiological studies appear to be normal. Immunotherapy with humanized anti-CEA IgG (hMN-15) monoclonal antibody is begun on a weekly basis for 4 weeks, at an intravenous dose of 300 mg/m$^2$ infused over 2 hours. One week prior to hMN-15 therapy, the patient receives 2 subcutaneous injections of 200 µg/m$^2$ GM-CSF, 3 days apart, and continued twice weekly during the 4 weeks of hMN-15 therapy. After these four weeks, both hMN-15 and GM-CSF are given at the same doses every other week for an additional 3 months, but the dose of GM-CSF is increased to 250 µg/m$^2$. Prior to each administration of the humanized anti-CEA antibody, the patient is given diphenhydramine (50 mg orally), and acetaminophen (500 mg orally).

At this time, the patient is restaged, with CT measurements made of the liver metastases and diverse radiological scans of the rest of the body. Blood is also taken for chemistries and for determination of his blood CEA titer. No areas of disease outside of the liver are noted, but the sum of the diameters of the measurable tumors in the liver appear to decrease by 40 percent, and the patient's blood CEA titer decreases to 18 ng/mL, thus indicating a therapeutic response.

Immunotherapy with hMN-15 and GM-CSF, given once every other week at 200 mg/m$^2$ for hMN-15 and 250 µg/m$^2$ for GM-CSF, are administered for another 2 months, and restaging shows additional decrease in the sum of the diameters of the liver tumors and a fall in the CEA titer to 10 ng/mL. Since tumor decrease is measured as being >65% over the pre-therapy baseline, the therapy is considered to have provided a partial response. After this, the doses are made less frequent, once every month for the next six months, and all studies indicate no change in disease. The patient is then followed for another 10 months, and remains in a partial remission, with no adverse reactions to the therapy, and generally without any symptoms of disease.

Example 7

Combined Immunotherapy and Chemotherapy of Metastatic Colon Cancer

ST is a 52-year-old woman presenting with liver and lung metastases of colon cancer following resection of the primary tumor. She is placed on a combined chemotherapy and immunotherapy protocol based on the Gramont schedule (de Gramont et al., J Clin Oncol. 2000, 18:2938-47), but with the addition of humanized anti-CEA monoclonal antibody IgG$_1$ (hMN-15). Prior to infusions of the antibody, she receives 50 mg orally of diphenhydramine and 500 mg orally of acetaminophen. She receives a 2-hr infusion of leucovorin (200 mg/m$^2$/day) followed by a bolus of 5-fluorouracil (400 mg/m$^2$/day) and 22-hour continuous infusion of 5-fluorouracil (600 mg/m$^2$/day) for 2 consecutive days every 2 weeks, together with oxaliplatin at 85 mg/m$^2$ as a 2-hr infusion in 250 mL of dextrose 5%, concurrent with leukovorin on day 1 (FOLFOX4 schedule). The patient also receives anti-emetic prophylaxis with a 5-hydroxyltryptamine-3-receptor antagonist. One week prior to this 2-week chemotherapy cycle, hMN-15 monoclonal anti-CEA antibody is infused over 2 hrs at a dose of 200 mg/m$^2$, and repeated each week of the 2-week chemotherapy cycle, and every week thereafter for the next month with another chemotherapy cycle. Also, a subcutaneous dose of 5 µg/kg/day of G-CSF is administered once weekly beginning with the second chemotherapy cycle, and continued at this dose for the duration of immunotherapy with hMN-15 antibody, over the next 3 months.

A total of 5 cycles of chemotherapy is performed with continued administration of hMN-15 antibody and filgrastim. Thereafter, hMN-15 and filgrastim therapy is given, at the same doses, every other week for the next 3 months, without chemotherapy. The patient is staged 2 months later, and her liver and lung metastases show shrinkage by computed tomography measurements of >80 percent of disease measured in the liver and lungs, as compared to the measurements made prior to therapy. Her blood CEA titer also shows a drop from the pre-therapy level of 63 ng/mL to 9 ng/mL. She is followed over the next 6 months, and her disease appears to be stable, with no new lesions found and no increase in the disease remaining in the liver and lungs. The patient's predominant toxicity is peripheral sensory neuropathy, which consists of laryngeopharyngeal dysesthesia. The patient also experiences diarrhea, mucositis, nausea and vomiting during the chemotherapy cycles, but these are not excessive. She does not experience any adverse events when only immunotherapy is administered, and is able to return to full-time activities without any significant restrictions.

Example 8

Effect of hMN-15 Pretreatment on CPT-11 Efficacy

The effects of pre-treatment with naked hMN-15 CEA Mab given 3 days prior to CPT-11 treatment is examined in a SUM1315 breast cancer model (Kuperwasser et al., Cancer Res. 2005, 65:6130-38). CPT-11 alone, hMN-15 alone, and combination therapy of hMN-15+CPT-11 where the hMN-15 is administered 3 days prior to the CPT-11 are compared. Dosages are as indicated in Example 5. hMN-15 alone increases median survival time by 21% under these conditions. CPT 11 alone increases survival by 76%. By contrast, the combination therapy where hMN-15 is administered 3 days prior to CPT-11 produces a median survival time increase of an additional 58% above CPT-11 alone. Pre-treatment with hMN-15 significantly prolongs survival of animals with low tumor burden in a metastatic model of human breast cancer. The synergistic effect of hMN-15 antibody with CPT-11 therapy is surprising.

Example 9

Effect of Administration Schedule on hMN-15 Synergy with CPT-11

A comparison is made of various administration schedules of naked hMN-15 CEA Mab and CPT-11 in a human colon cancer model. Giving hMN-15 3 days before CPT-11 is the most effective. Dosages are as indicated Example 5. When the order is reversed (CPT-11 is given 3 days before hMN-15) or when both are given together at the same time, median survival time of 70 days is an increase over the untreated control group (35 days) but is still less than the median survival time of 105 days with the hMN-15 pre-treatment 3 days before CPT-11.

Example 10

Class I Anti-CEA Antibodies and Medullary Thyroid Cancer Therapy

TT, a human medullary thyroid cell line, is purchased from the American Type Culture Collection. The cells are grown as monolayers in DMEM (Life Technologies, Gaithersburg, Md.) supplemented with 10% fetal bovine serum, penicillin (100β/ml), streptomycin (100 µg/ml), and L-glutamine (2 mM). The cells are routinely passaged after detachment with trypsin, 0.2% EDTA.

Tumors are propagated in female nu/nu mice (Taconic Farms, Germantown, N.Y.) at 6-8 weeks of age by s.c. injection of $2 \times 10^8$ washed TT cells, which is propagated in tissue culture. Antibodies are injected i.v., via the lateral tail vein, into the tumor-bearing animals. Tumor size is monitored by weekly measurements of the length, width, and depth of the tumor using a caliper. Tumor volume is calculated as the product of the three measurements.

To study whether naked hMN-15 can add to the efficacy of DTIC, TT bearing nude mice are given DTIC (75 µg/dose) in combination with a course of treatment of the unlabeled MAb. DTIC is administered for 3 consecutive days at 75 µg/dose as one course, beginning 2 days after s.c. injection of TT cells. hMN-15 MAb treatment is initiated 3 days prior to the first dose of DTIC, at 100 µg/dose/day for 5 days in the first two weeks, then twice weekly. Significant delays in tumor growth are caused by these schedules of either MAb therapy or chemotherapy alone. Surprisingly, the 75-µg dose of DTIC in combination with this schedule of hMN-15 is more effective than either treatment alone. At 7 weeks, 8/10 mice in the 75 µg DTIC+MAb group have no palpable tumor, compared to 1/10 in the 75 µg DTIC-only group and 0/10 in the untreated and MAb-only groups. Mean tumor volumes at 7 weeks are 0.018+0.039 cm³ (75 µg DTIC+hMN-15), 0.284+0.197 cm³ (75 µg DTIC), 0.899+0.545 cm³ (hMN-15) and 1.578+0.959 cm³ (untreated).

Example 11

Preparation of DNL Constructs for Pretargeting

In various forms, the DNL technique may be used to make dimers, trimers, tetramers, hexamers, etc. comprising virtually any antibodies or fragments thereof or other effector moieties, such as cytokines. For certain preferred embodiments, IgG antibodies or Fab antibody fragments may be produced as fusion proteins containing either a DDD or AD sequence. Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. For purposes of pre-targeting, an antibody or fragment containing a binding site for an antigen associated with a target tissue to be treated, such as a tumor, may be combined with a second antibody or fragment that binds a hapten on a targetable construct. In exemplary embodiments, the tumor targeting antibody or fragment is a chimeric, humanized or human MN-15 antibody comprising the 6 MN-15 CDR sequences, while the hapten binding moiety may be an anti-HSG or anti-DTPA antibody. The bispecific antibody (DNL construct) is administered to a subject, circulating antibody is allowed to clear from the blood and localize to target tissue, and a targetable construct attached to at least one therapeutic and/or diagnostic agent is added and binds to the localized antibody.

Independent transgenic cell lines may be developed for each Fab or IgG fusion protein. Once produced, the modules can be purified if desired or maintained in the cell culture supernatant fluid. Following production, any $DDD_2$-fusion protein module can be combined with any AD-fusion protein module to generate a bispecific DNL construct. For different types of constructs, different AD or DDD sequences may be utilized.

```
DDD1:
                                          (SEQ ID NO: 11)
SHIQIPPGLTELLQGYTVEVLRQQPPDLVEFAVEYFTRLREARA

DDD2:
                                          (SEQ ID NO: 12)
CGHIQIPPGLTELLQGYTVEVLRQQPPDLVEFAVEYFTRLREARA

AD1:
                                          (SEQ ID NO: 13)
QIEYLAKQIVDNAIQQA

AD2:
                                          (SEQ ID NO: 14)
CGQIEYLAKQIVDNAIQQAGC
```

The plasmid vector pdHL2 has been used to produce a number of antibodies and antibody-based constructs. (See, Gillies et al., J Immunol Methods (1989), 125:191-202; Losman et al., Cancer (Phila) (1997), 80:2660-6.) The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human RIIα (referred to as DDD1, SEQ ID NO:11). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1, SEQ ID NO:13), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC) followed by four glycines and a serine, with the final two codons (GS) comprising a Bam HI restriction site. The 410 bp PCR amplimer was cloned into the pGemT PCR cloning vector (Promega, Inc.) and clones were screened for inserts in the T7 (5') orientation.

Construction of $(G_4S)_2DDD1$ ($(G_4S)_2$ disclosed as SEQ ID NO: 15)

A duplex oligonucleotide, designated $(G_4S)_2DDD1$ ($(G_4S)_2$ disclosed as SEQ ID NO: 15), was synthesized by Sigma Genosys (Haverhill, UK) to code for the amino acid sequence of DDD1 preceded by 11 residues of the linker peptide, with the first two codons comprising a BamHI restriction site. A stop codon and an EagI restriction site are appended to the 3'end. The encoded polypeptide sequence is shown below.

```
                                      (SEQ ID NO: 16)
GSGGGGSGGGGSHIQIPPGLTELLQGYTVEVLRQQPPDLVEFAVEY
FTRLREARA
```

Two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into pGemT and screened for inserts in the T7 (5') orientation.

Construction of $(G_4S)_2$-AD1 ($(G_4S)_2$ Disclosed as SEQ ID NO: 15)

A duplex oligonucleotide, designated $(G_4S)_2$-AD1 ($(G_4S)_2$ disclosed as SEQ ID NO: 15), was synthesized (Sigma Genosys) to code for the amino acid sequence of AD1 preceded by 11 residues of the linker peptide with the first two codons comprising a BamHI restriction site. A stop codon and an EagI restriction site are appended to the 3'end. The encoded polypeptide sequence is shown below.

```
                                      (SEQ ID NO: 17)
GSGGGGSGGGGSQIEYLAKQIVDNAIQQA
```

Two complimentary overlapping oligonucleotides encoding the above peptide sequence, designated AKAP-IS Top and AKAP-IS Bottom, were synthesized and annealed. The duplex was amplified by PCR. The amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in CH1-pGemT to generate the shuttle vector CH1-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-15-pdHL2

C-DDD1-Fd-hMN-15-pdHL2 is an expression vector for production of a stable dimer that comprises two copies of a fusion protein C-DDD1-Fab-hMN-15, in which DDD1 is linked to hMN-15 Fab at the carboxyl terminus of CH1 via a flexible peptide spacer. The plasmid vector hMN15-pdHL2, which is used to produce hMN-15 IgG, is converted to C-DDD1-Fd-hMN-15-pdHL2 by digestion with SacII and EagI restriction endonucleases to remove the CH1-CH3 domains and insertion of the CH1-DDD1 fragment, which is excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

C-DDD2-Fd-hMN-15-pdHL2

C-DDD2-Fd-hMN-15-pdHL2 is an expression vector for production of C-DDD2-Fab-hMN-15, which possesses a dimerization and docking domain sequence of DDD2 appended to the carboxyl terminus of the Fd of hMN-15 via a 14 amino acid residue Gly/Ser peptide linker. The fusion protein secreted is composed of two identical copies of hMN-15 Fab held together by non-covalent interaction of the DDD2 domains.

The expression vector is engineered as follows. Two overlapping, complimentary oligonucleotides, which comprise the coding sequence for part of the linker peptide (GGGGSGGGCG, SEQ ID NO:18) and residues 1-13 of DDD2 (SEQ ID NO:12), are made synthetically. The oligonucleotides are annealed and phosphorylated with T4 PNK, resulting in overhangs on the 5' and 3' ends that are compatible for ligation with DNA digested with the restriction endonucleases BamHI and PstI, respectively.

The duplex DNA is ligated with the shuttle vector CH1-DDD1-pGemT, which is prepared by digestion with BamHI and PstI, to generate the shuttle vector CH1-DDD2-pGemT. A 507 bp fragment is excised from CH1-DDD2-pGemT with SacII and EagI and ligated with the IgG expression vector hMN15-pdHL2, which is prepared by digestion with SacII and EagI. The final expression construct is designated C-DDD2-Fd-hMN-15-pdHL2. Similar techniques have been utilized to generated DDD2-fusion proteins of the Fab fragments of a number of different humanized antibodies.

H679-Fd-AD2-pdHL2 h679-Fab-AD2, was designed to pair as B to C-DDD2-Fab-hMN-15 as A. h679-Fd-AD2-pdHL2 is an expression vector for the production of h679-Fab-AD2, which possesses an anchor domain sequence of AD2 (SEQ ID NO:14) appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of Trimeric MN-15-679 Construct

A trimeric DNL construct is obtained by reacting C-DDD2-Fab-hMN-15 with h679-Fab-AD2. A pilot batch of DNL trimer is generated with >90% yield as follows. Protein L-purified C-DDD2-Fab-hMN-15 (200 mg) is mixed with h679-Fab-AD2 (60 mg) at a 1.4:1 molar ratio. The total protein concentration is 1.5 mg/ml in PBS containing 1 mM EDTA. Subsequent steps involved TCEP reduction, HIC chromatography, DMSO oxidation, and IMP 291 affinity chromatography. Addition of 5 mM TCEP rapidly results in the formation of $a_2b$ complex consistent with a 157 kDa protein expected for the binary structure. The trimeric DNL construct is purified to near homogeneity by IMP 291 affinity chromatography. IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrates the removal of $a_4$, $a_2$ and free kappa chains from the product. Binding studies indicate that the trimeric DNL construct incorporating the hMN-15 antibody binds to CEA and HSG, with affinities similar to the parent MN-15 and 679 antibodies.

Production of TF10 Bispecific Antibody

A similar protocol was used to generate a trimeric TF10 DNL construct, comprising two copies of a C-DDD2-Fab-hPAM4 and one copy of C-AD2-Fab-679. The cancer-targeting antibody component in TF10 is derived from hPAM4, a humanized anti-pancreatic cancer mucin MAb that has been studied in detail as a radiolabeled MAb (e.g., Gold et al., *Clin. Cancer Res.* 13: 7380-7387, 2007). The hapten-binding component is derived from h679, a humanized anti-histaminyl-succinyl-glycine (HSG) MAb discussed above. The TF10 bispecific ([hPAM4]$_2$×h679) antibody was produced using the method disclosed for production of the (anti CEA)$_2$×anti HSG bsAb, as described above. The TF10 construct bears two humanized PAM4 Fabs and one humanized 679 Fab.

The two fusion proteins (hPAM4-DDD and h679-AD2) were expressed independently in stably transfected myeloma cells. The tissue culture supernatant fluids were combined, resulting in a two-fold molar excess of hPAM4-DDD. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

hMN-15-Fd-AD2-pdHL2

For certain DNL constructs, it is preferred to use an hMN-15-Fab-AD2 fusion protein, which possesses an anchor domain sequence of AD2 (SEQ ID NO:14) appended to the carboxyl terminal end of the CH1 domain via a 14 amino acid residue Gly/Ser peptide linker An hMN-15-Fab-AD2 construct may be utilized, for example, to prepare a DNL construct comprising a lower number of hMN-15 subunits and a greater number of other effector moiety subunits, such as a toxin, cytokine, drug or another antibody or antibody fragment.

The expression vector is engineered as described above for the h679-Fab-AD2 fusion protein. Two overlapping, complimentary oligonucleotides (AD2 Top and AD2 Bottom), which comprise the coding sequence for AD2 and part of the linker sequence, are made synthetically. The oligonucleotides are annealed and phosphorylated with T4 PNK, resulting in overhangs on the 5' and 3' ends that are compatible for ligation with DNA digested with the restriction endonucleases BamHI and SpeI, respectively.

The duplex DNA is ligated into the shuttle vector CH1-AD1-pGemT, which is prepared by digestion with BamHI and SpeI, to generate the shuttle vector CH1-AD2-pGemT. A 429 base pair fragment containing CH1 and AD2 coding sequences is excised from the shuttle vector with SacII and EagI restriction enzymes and ligated into hMN-15-pdHL2 vector prepared by digestion with those same enzymes. The final expression vector is hMN-15-Fd-AD2-pdHL2.

Example 12

Imaging Using Pretargeting with hMN-15-679 DNL Construct and $^{111}$In-Labeled Peptides The following study demonstrates the feasibility of in vivo imaging using the pretargeting technique with labeled targeting peptides and bispecific antibodies incorporating hMN-15. The hMN-15-679 DNL construct, comprising two copies of a C-DDD2-Fab-hMN-15 and one copy of C-AD2-Fab-679, is prepared as described in the preceding Example. Nude mice bearing 0.2 to 0.3 g human colon cancer xenografts are imaged, using pretargeting with the hMN-15-679 DNL construct and an $^{111}$In-IMP-288 peptide. The results show clearly delineated tumors in animal models using a bsMAb pretargeting method. Experimental animals receive different doses of hMN-15-679 DNL construct at 10:1 or 20:1 mole ratio to the moles of peptide given, and the next day they are given an $^{111}$In-labeled diHSG peptide (IMP 288). The control animals receive only the $^{111}$In-IMP-288 (no pretargeting). The images are taken 3 h after the injection of the labeled peptide and show clear localization of 0.2-0.3 g tumors in the pretargeted animals with both doses of DNL construct, with no localization in the animals given the $^{111}$In-peptide alone.

Example 13

PEGylated DNL Constructs

In certain embodiments, it may be preferred to prepare constructs comprising PEGylated forms of antibody or immunoconjugate, for example to increase the serum half-life of the antibody or immunoconjugate moiety. Such PEGylated constructs may be prepared by the DNL technique.

In a preferred method, the effector moiety to be PEGylated, such as hMN-15 Fab, is linked to a DDD sequence to generate the DDD module. A PEG reagent of a selected molecular size is derivatized with a complementary AD sequence and the resulting PEG-AD module is combined with the DDD module to produce a PEGylated conjugate that consists of a single PEG tethered site-specifically to two copies of the hMN-15 Fab or other effector moiety via the disulfide bonds formed between DDD and AD. The PEG reagents may be capped at one end with a methoxy group (m-PEG), can be linear or branched, and may contain one of the following functional groups: propionic aldehyde, butyric aldehyde, ortho-pyridylthioester (OPTE), N-hydroxysuccinimide (NHS), thiazolidine-2-thione, succinimidyl carbonate (SC), maleimide, or ortho-pyridyldisulfide (OPPS). Among the effector moieties that may be of interest for PEGylation are enzymes, cytokines, chemokines, growth factors, peptides, aptamers, hemoglobins, antibodies and antibody fragments. The method is not limiting and a wide variety of agents may be PEGylated using the disclosed methods and compositions. PEG of various sizes and derivatized with a variety of reactive moieties may be obtained from commercial sources, such as NEKTAR® Therapeutics (Huntsville, Ala.).

Generation of PEG-AD2 Modules

```
IMP350:
                                    (SEQ ID NO: 19)
CGQIEYLAKQIVDNAIQQAGC(SS-tbu)-NH2
```

IMP350, incorporating the sequence of AD2, was made on a 0.1 mmol scale with Sieber Amide resin using Fmoc methodology on a peptide synthesizer. Starting from the C-terminus the protected amino acids used were Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH and Fmoc-Cys(Trt)-OH. The peptide was cleaved from the resin and purified by reverse phase (RP)-HPLC.

Synthesis of PEG$_{20}$-IMP350

IMP350 (0.0104 g) was mixed with 0.1022 g of mPEG-OPTE (20 kDa, NEKTAR® Therapeutics) in 7 mL of 1 M Tris buffer at pH 7.81. Acetonitrile, 1 mL, was then added to dissolve some suspended material. The reaction was stirred at room temperature for 3 h and then 0.0527 g of TCEP was added along with 0.0549 g of cysteine. The reaction mixture was stirred for 1.5 h and then purified on a PD-10 desalting column, which was equilibrated with 20% methanol in water. The sample was eluted, frozen and lyophilized to obtain 0.0924 g of crude PEG$_{20}$-IMP350 (MH+23508 by MALDI).

Synthesis of IMP362 (PEG$_{20}$-IMP360)

```
IMP360:
                                    (SEQ ID NO: 20)
CGQIEYLAKQIVDNAIQQAGC(SS-tbu)G-EDANS MH+ 2660
```

IMP 360, incorporating the AD2 sequence, was synthesized on a 0.1 mmol scale with Fmoc-Gly-EDANS resin using Fmoc methodology on a peptide synthesizer. The Fmoc-Gly-OH was added to the resin manually using 0.23 g of Fmoc-Gly-OH, 0.29 g of HATU, 26 µL, of DIEA, 7.5 mL of DMF and 0.57 g of EDANS resin (NOVABIOCHEM®). The reagents were mixed and added to the resin. The reaction was mixed at room temperature for 2.5 hr and the resin was washed with DMF and IPA to remove the excess reagents. Starting from the C-terminus the protected amino acids used were Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH and Fmoc-Cys(Trt)-OH. The peptide was cleaved from the resin and purified by RP-HPLC.

For synthesis of IMP362, IMP360 (0.0115 g) was mixed with 0.1272 g of mPEG-OPTE (20 kDa, NEKTAR® Therapeutics) in 7 mL of 1 M tris buffer, pH 7.81. Acetonitrile (1 mL) was then added to dissolve some suspended material. The reaction was stirred at room temperature for 4 h and then 0.0410 g of TCEP was added along with 0.0431 g of cysteine. The reaction mixture was stirred for 1 h and purified on a PD-10 desalting column, which was equilibrated with 20% methanol in water. The sample was eluted, frozen and lyophilized to obtain 0.1471 g of crude IMP362 (MH+ 23713).

Synthesis of IMP413 (PEG$_{30}$-IMP360)

For synthesis of IMP 413, IMP 360 (0.0103 g) was mixed with 0.1601 g of mPEG-OPTE (30 kDa, NEKTAR® Therapeutics) in 7 mL of 1 M tris buffer at pH 7.81. Acetonitrile (1 mL) was then added to dissolve some suspended material. The reaction was stirred at room temperature for 4.5 h and then 0.0423 g of TCEP was added along with 0.0473 g of cysteine. The reaction mixture was stirred for 2 h followed by dialysis for two days. The dialyzed material was frozen and lyophilized to obtain 0.1552 g of crude IMP413 (MH+ 34499).

Synthesis of IMP421

```
IMP 421
                                    (SEQ ID NO: 21)
Ac-C-PEG3-C(S-tBu)GQIEYLAKQIVDNAIQQAGC
    (S-tBu)G-NH2
```

The peptide IMP421, MH+ 2891 was made on NOVASYN® TGR resin (487.6 mg, 0.112 mmol) by adding the following amino acids to the resin in the order shown: Fmoc-Gly-OH, Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH, Fmoc-Cys(t-Buthio)-OH, Fmoc-NH-PEG$_3$-COOH, Fmoc-Cys(Trt)-OH. The N-terminal amino acid was protected as an acetyl derivative. The peptide was then cleaved from the resin and purified by RP-HPLC to yield 32.7 mg of a white solid.

Synthesis of IMP457

IMP 421 (SEQ ID NO:21), incorporating the sequence of AD2, was synthesized by standard chemical means. To a solution of 15.2 mg (5.26 μmol) IMP 421 (F.W. 2890.50) and 274.5 mg (6.86 μmol) mPEG2-MAL-40K in 1 mL of acetonitrile was added 7 mL 1 M Tris pH 7.8 and allowed to react at room temperature for 3 h. The excess mPEG2-MAL-40K was quenched with 49.4 mg L-cysteine, followed by S—S-tBu deprotection over one hour with 59.1 mg TCEP. The reaction mixture was dialyzed overnight at 2-8° C. using two 3-12 mL capacity 10K SLIDE-A-LYZER® dialysis cassettes (4 ml into each cassette) into 5 L of 5 mM ammonium acetate, pH 5.0. Three more 5 L buffer changes of 5 mM ammonium acetate, pH 5.0 were made the next day with each dialysis lasting at least 21/2 h. The purified product (19.4 mL) was transferred into two 20 mL scintillation vials, frozen and lyophilized to yield 246.7 mg of a white solid. MALDI-TOF gave results of mPEG2-MAL-40K 42,982 and IMP-457 45,500.

Example 14

Generation of PEGylated hMN-15 by DNL

A DNL structure is prepared having two copies of hMN-15 Fab coupled to a 20 kDa PEG. A DNL reaction is performed by the addition of reduced and lyophilized IMP362 in 10-fold molar excess to hMN-15 Fab-DDD2 in 250 mM imidazole, 0.02% Tween 20, 150 mM NaCl, 1 mM EDTA, 50 mM NaH$_2$PO$_4$, pH 7.5. After 6 h at room temperature in the dark, the reaction mixture is dialyzed against CM Loading Buffer (150 mM NaCl, 20 mM NaAc, pH 4.5) at 4° C. in the dark. The solution is loaded onto a 1-mL Hi-Trap CM-FF column (AMERSHAM®), which is pre-equilibrated with CM Loading buffer. After sample loading, the column is washed with CM loading buffer to baseline, followed by washing with 15 mL of 0.25 M NaCl, 20 mM NaAc, pH 4.5. The PEGylated hMN-15 is eluted with 12.5 mL of 0.5 M NaCl, 20 mM NaAc, pH 4.5.

The conjugation process is analyzed by SDS-PAGE with Coomassie blue staining Under non-reducing conditions, the Coomassie blue-stained gel reveals the presence of a major band in the reaction mixture, which is absent in the unbound or 0.25 M NaCl wash fraction, but evident in the 0.5 M NaCl fraction. Fluorescence imaging, which is used to detect the EDANS tag on IMP362, demonstrates that the band contains IMP362 and the presence of excess IMP362 in the reaction mixture and the unbound fraction. The DNL reaction results in the site-specific and covalent conjugation of IMP362 with a dimer of hMN-15 Fab. Under reducing conditions, which breaks the disulfide linkage, the components of the DNL structures are resolved. The calculated MW of the (hMN-15 Fab)$_2$-PEG construct matches that determined by MALDI TOF. Overall, the DNL reaction results in a near quantitative yield of a homogeneous product that is >90% pure after purification by cation-exchange chromatography.

Another DNL reaction is performed by the addition of reduced and lyophilized IMP457 in 10-fold molar excess to hMN-15 Fab-DDD2 in 250 mM imidazole, 0.02% Tween 20, 150 mM NaCl, 1 mM EDTA, 50 mM NaH$_2$PO$_4$, pH 7.5. After 60 h at room temperature, 1 mM oxidized glutathione is added to the reaction mixture, which is then held for an additional 2 h. The mixture is diluted 1:20 with CM Loading Buffer (150 mM NaCl, 20 mM NaAc, pH 4.5) and titrated to pH 4.5 with acetic acid. The solution is loaded onto a 1-mL Hi-Trap CM-FF column (AMERSHAM®), which is pre-equilibrated with CM Loading Buffer. After sample loading, the column is washed with CM Loading Buffer to baseline, followed by washing with 15 mL of 0.25 M NaCl, 20 mM NaAc, pH 4.5. The PEGylated product is eluted with 20 mL of 0.5 M NaCl, 20 mM NaAc, pH 4.5. The DNL construct is concentrated to 2 mL and diafiltered into 0.4 M PBS, pH 7.4. The final PEGylated hMN-15 Fab$_2$ construct is approximately 90% purity as determined by SDS-PAGE.

A DNL construct having two copies of hMN-15 Fab coupled to a 30 kDa PEG is prepared as described immediately above using IMP413 instead of IMP362. The PEGylated hMN-15 Fab$_2$ DNL construct is purified as described above and obtained in approximately 90% purity. The PEGylated DNL constructs may be used for therapeutic methods as described above for non-PEGylated forms of hMN-15. It is observed that PEGylation of hMN-15 Fab$_2$ increases the serum half-life of the hMN-15 moiety, as expected.

Example 15

Generation of DDD Module Based on Interferon (IFN)-α2b

The cDNA sequence for IFN-α2b was amplified by PCR, resulting in a sequence comprising the following features, in which XbaI and BamHI are restriction sites, the signal peptide is native to IFN-α2b, and 6 His is a hexahistidine tag (SEQ ID NO:37): XbaI - - - Signal peptide - - - IFNα2b - - - 6 His - - - BamHI ("6 His" disclosed as SEQ ID NO:37). The resulting secreted protein consists of IFN-α2b fused at its C-terminus to a polypeptide consisting of SEQ ID NO:22.

```
                                           (SEQ ID NO: 22)
KSHHHHHHGSGGGGSGGGCGHIQIPPGLTELLQGYTVEVLRQQPPDLV
EFAVEYFTRLREARA
```

PCR amplification was accomplished using a full length human IFNα2b cDNA clone (INVITROGEN® Ultimate ORF human clone cat# HORF01Clone ID IOH35221) as a template and the following oligonucleotides as primers:

```
IFNA2 Xba I Left
                                           (SEQ ID NO: 23)
5'-TCTAGACACAGGACCTCATCATGGCCTTGACCTTTGCTTTAC
TGG-3'

IFNA2 BamHI right
                                           (SEQ ID NO: 24)
5'GGATCCATGATGGTGATGATGGTGTGACTTTTCCTTACTTCTT
AAACTTTCTTGC-3'
```

The PCR amplimer was cloned into the PGEMT® vector (PROMEGA®). A DDD2-pdHL2 mammalian expression vector was prepared for ligation with IFN-α2b by digestion with XbaI and Bam HI restriction endonucleases. The IFN-α2b amplimer was excised from PGEMT® with XbaI and Bam HI and ligated into the DDD2-pdHL2 vector to generate the expression vector IFN-α2b-DDD2-pdHL2.

IFN-α2b-DDD2-pdHL2 was linearized by digestion with SalI enzyme and stably transfected into Sp/EEE myeloma cells by electroporation (see, e.g., U.S. Pat. No. 7,537,930, the Examples section of which is incorporated herein by reference). Two clones were found to have detectable levels of IFN-α2b by ELISA. One of the two clones, designated 95, was adapted to growth in serum-free media without substantial decrease in productivity. The clone was subsequently amplified with increasing methotrexate (MTX) concentrations from 0.1 to 0.8 μM over five weeks. At this stage, it was sub-cloned by limiting dilution and the highest producing sub-clone (95-5) was expanded. The productivity of 95-5 grown in shake-flasks was estimated to be 2.5 mg/L using commercial rIFN-α2b (CHEMICON® IF007, Lot 06008039084) as a standard.

Clone 95-5 was expanded to 34 roller bottles containing a total of 20 L of serum-free Hybridoma SFM with 0.8 μM MTX and allowed to reach terminal culture. The supernatant fluid was clarified by centrifugation and filtered (0.2 μM). The filtrate was diafiltered into 1× Binding buffer (10 mM imidazole, 0.5 M NaCl, 50 mM NaH$_2$PO$_4$, pH 7.5) and concentrated to 310 mL in preparation for purification by immobilized metal affinity chromatography (IMAC). The concentrate was loaded onto a 30-mL Ni-NTA column, which was washed with 500 mL of 0.02% Tween 20 in 1× binding buffer and then 290 mL of 30 mM imidazole, 0.02% Tween 20, 0.5 M NaCl, 50 mM NaH$_2$PO$_4$, pH 7.5. The product was eluted with 110 mL of 250 mM imidazole, 0.02% Tween 20, 150 mM NaCl, 50 mM NaH$_2$PO$_4$, pH 7.5. Approximately 6 mg of IFNα2b-DDD2 was purified.

The purity of IFN-α2b-DDD2 was assessed by SDS-PAGE under reducing conditions (not shown). IFN-α2b-DDD2 was the most heavily stained band and accounted for approximately 50% of the total protein (not shown). The product resolved as a doublet with an M$_r$ of ~26 kDa, which is consistent with the calculated MW of IFN-α2b-DDD2-SP (26 kDa). There was one major contaminant with a M$_r$ of 34 kDa and many faint contaminating bands (not shown).

Example 16

Generation of hMN-15 Fab-(IFN-α2b)$_2$ by DNL

Creation of C—H-AD2-IgG-pdHL2 Expression Vectors.

The pdHL2 mammalian expression vector has been used to mediate the expression of many recombinant IgGs. A plasmid shuttle vector was produced to facilitate the conversion of any IgG-pdHL2 vector into a C—H-AD2-IgG-pdHL2 vector. The gene for the Fc (CH2 and CH3 domains) was amplified using the pdHL2 vector as a template and the oligonucleotides Fc BglII Left and Fc Bam-EcoRI Right as primers.

```
Fc BglII Left
                                          (SEQ ID NO: 25)
5'-AGATCTGGCGCACCTGAACTCCTG-3'

Fc Bam-EcoRI Right
                                          (SEQ ID NO: 26)
5'-GAATTCGGATCCTTTACCCGGAGACAGGGAGAG-3'
```

The amplimer was cloned in the PGEMT® PCR cloning vector. The Fc insert fragment was excised from PGEMT® and ligated with AD2-pdHL2 vector to generate the shuttle vector Fc-AD2-pdHL2.

Generation of hMN-15 IgG-AD2

To convert any IgG-pdHL2 expression vector to a C—H-AD2-IgG-pdHL2 expression vector, an 861 bp BsrGI/NdeI restriction fragment is excised from the former and replaced with a 952 bp BsrGI/NdeI restriction fragment excised from the Fc-AD2-pdHL2 vector. BsrGI cuts in the CH3 domain and NdeI cuts downstream (3') of the expression cassette. This method is used to generate an hMN-15 IgG-AD2 protein.

Generation of hMN-15 IgG-(IFN-α2b)$_2$ Construct

A DNL reaction is performed by the addition of reduced and lyophilized hMN-15 IgG-AD2 to IFN-α2b-DDD2 in 250 mM imidazole, 0.02% Tween 20, 150 mM NaCl, 1 mM EDTA, 50 mM NaH$_2$PO$_4$, pH 7.5. After 6 h at room temperature in the dark, the reaction mixture is dialyzed against CM Loading Buffer (150 mM NaCl, 20 mM NaAc, pH 4.5) at 4° C. in the dark. The solution is loaded onto a 1-mL Hi-Trap CM-FF column (AMERSHAM®), which is pre-equilibrated with CM Loading buffer. After sample loading, the column is washed with CM loading buffer to baseline, followed by washing with 15 mL of 0.25 M NaCl, 20 mM NaAc, pH 4.5. The product is eluted with 12.5 mL of 0.5 M NaCl, 20 mM NaAc, pH 4.5. The DNL reaction results in the site-specific and covalent conjugation of hMN-15 IgG with a dimer of IFN-α2b. Both the IgG and IFN-α2b moieties retain their respective physiological activities in the DNL construct. This technique may be used to attach any cytokine or other physiologically active protein or peptide to hMN-15 for targeted delivery to colon cancer or other cancers that express the CEA antigen.

Example 17

Preparation of DNL Bispecific Antibody Constructs

Methods of preparing bispecific DNL antibody constructs are described, for example, in U.S. Pat. No. 7,521,056, the methods section of which is incorporated herein by reference.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

Production of C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd via a 14 amino acid residue Gly/Ser peptide linker. The fusion protein secreted is composed of two identical copies of hMN-14 Fab held together by non-covalent interaction of the DDD2 domains.

The C-DDD2-Fd-hMN-14-pdHL2 vector was transfected into Sp/EEE myeloma cells by electroporation. The di-cistronic expression vector directs the synthesis and secretion of both hMN-14 kappa light chain and C-DDD2-Fd-hMN-14, which combine to form C-DDD2-Fab-hMN14. Dimerization occurs via the DDD2 moiety, resulting in two reactive sulfhydryl groups provided by the cysteine residue in each DDD2. Following electroporation, the cells were plated in 96-well tissue culture plates and transfectant clones were selected with 0.05 .mu.M methotrexate (MTX).

Clones were screened for protein expression by ELISA using microtitre plates coated with WI2 (hMN-14 anti-Id) and detection with goat anti-human Fab-HRP. The highest producing clones had an initial productivity of approximately 100 mg/L. A total of 200 mg of C-DDD2-hMN-14 was purified by protein L affinity chromatography from 1.8 liters of roller bottle culture.

Generation of Trimeric hMN-14-hMN-15 Bispecific DNL Construct hMN-15-Fab-AD2 is prepared as described in Example 12. hMN-14-Fab-DDD2 is prepared as described above. The two fusion proteins (hMN-14-Fab-DDD2 and hMN-15-Fab- AD2) are expressed independently in stably transfected myeloma cells. The tissue culture supernatant fluids are combined, resulting in a two-fold molar excess of hMN-14-Fab-DDD2. The reaction mixture is incubated at room temperature for 24 hours under mild reducing conditions using 1 mM reduced glutathione. Following reduction, the DNL reaction is completed by mild oxidation using 2 mM oxidized glutathione. The trimeric bispecific DNL construct is isolated by affinity chromatography using an anti-idiotypic antibody against hMN-14. The complex retains the binding affinities of both the hMN-14 and hMN-15 antibodies.

Generation of Trimeric hPAM4-hMN-15 Bispecific DNL Construct hMN-15-Fab-AD2 and hPAM4-Fab-DDD2 are prepared as described in Example 11. The two fusion proteins (hPAM4-Fab-DDD2 and hMN-15-Fab-AD2) are expressed independently in stably transfected myeloma cells. The tissue culture supernatant fluids are combined, resulting in a two-fold molar excess of hPAM4-Fab-DDD2. The reaction mixture is incubated at room temperature for 24 hours under mild reducing conditions using 1 mM reduced glutathione. Following reduction, the DNL reaction is completed by mild oxidation using 2 mM oxidized glutathione. The trimeric bispecific DNL construct is isolated by affinity chromatography using an anti-idiotypic antibody against hMN-15. The complex retains the binding affinities of both the hPAM4 and hMN-15 antibodies.

The skilled artisan will realize that a trimeric Fab construct can be prepared using virtually any antibodies that have been cloned in an expression vector, using appropriate restriction endonucleases and standard molecular cloning techniques. Thus, combinations of hMN-15 with any other antibody or antibody fragment may be prepared by DNL.

Example 18

Production of Targeting Peptides for Use in Pretargeting and $^{18}$F Labeling

In certain embodiments, $^{18}$F-labeled proteins or peptides are prepared by a novel technique and used for diagnostic and/or imaging studies, such as PET imaging. The novel technique for $^{18}$F labeling involves preparation of an $^{18}$F-metal complex, preferably an $^{18}$F-aluminum complex, which is chelated to a chelating moiety, such as DOTA, NOTA or NETA or derivatives thereof. Chelating moieties may be attached to proteins, peptides or any other molecule using conjugation techniques well known in the art. In certain preferred embodiments, the $^{18}$F—Al complex is formed in solution first and then attached to a chelating moiety that is already conjugated to a protein or peptide. However, in alternative embodiments the aluminum may be first attached to the chelating moiety and the $^{18}$F added later.

Peptide Synthesis

Peptides were synthesized by solid phase peptide synthesis using the Fmoc strategy. Groups were added to the side chains of diamino amino acids by using Fmoc/Aloc protecting groups to allow differential deprotection. The Aloc groups were removed by the method of Dangles et. al. (*J. Org. Chem.* 1987, 52:4984-4993) except that piperidine was added in a 1:1 ratio to the acetic acid used. The unsymmetrical tetra-t-butyl DTPA was made as described in McBride et al. (U.S. Pat. No. 7,405,320, the Examples section of which is incorporated herein by reference).

The tri-t-butyl DOTA, symmetrical tetra-t-butyl DTPA, ITC-benzyl DTPA, p-SCN-Bn-NOTA and TACN were obtained from MACROCYCLICS® (Dallas, Tex.). The DiB-ocTACN, NODA-GA(tBu)$_3$ and the NO2AtBu were purchased from CheMatech (Dijon, France). The Aloc/Fmoc Lysine and Dap (diaminopropionic acid derivatives (also Dpr)) were obtained from CREOSALUS® (Louisville, Ky.) or BACHEM® (Torrance, Calif.). The Sieber Amide resin was obtained from NOVABIOCHEM® (San Diego, Calif.). The remaining Fmoc amino acids were obtained from CREOSALUS®, BACHEM®, PEPTECH® (Burlington, Mass.), EMD BIOSCIENCES® (San Diego, Calif.), CHEM IMPEX® (Wood Dale, Ill.) or NOVABIOCHEM®. The aluminum chloride hexahydrate was purchased from SIGMA-ALDRICH® (Milwaukee, Wis.). The remaining solvents and reagents were purchased from FISHER SCIENTIFIC® (Pittsburgh, Pa.) or SIGMA-ALDRICH® (Milwaukee, Wis.). $^{18}$F was supplied by IBA MOLECULAR® (Somerset, N.J.)

$^{18}$F-Labeling of IMP 272

The first peptide that was prepared and $^{18}$F-labeled was IMP 272:

DTPA-Gln-Ala-Lys(HSG)-D-Tyr-Lys(HSG)-NH$_2$ MH$^+$ 1512

IMP 272 was synthesized as described (McBride et al., U.S. Pat. No. 7,534,431, the Examples section of which is incorporated herein by reference).

Acetate buffer solution- Acetic acid, 1.509 g was diluted in ~160 mL water and the pH was adjusted by the addition of 1 M NaOH then diluted to 250 mL to make a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28× $10^{-7}$ mol IMP 272 was dissolved in 364 µL of the 0.1 M pH 4 acetate buffer solution to obtain a 2 mM stock solution of the peptide.

F-18 Labeling of IMP 272—A 3 µL aliquot of the aluminum stock solution was placed in a REACTI-VIAL™ and mixed with 50 µL $^{18}$F (as received) and 3 µL of the IMP 272 solution. The solution was heated in a heating block at 110° C. for 15 min and analyzed by reverse phase HPLC. HPLC analysis (not shown) showed 93% free $^{18}$F and 7% bound to the peptide. An additional 10 µL of the IMP 272 solution was added to the reaction and it was heated again and analyzed by reverse phase HPLC (not shown). The HPLC trace showed 8% $^{18}$F at the void volume and 92% of the activity attached to the peptide. The remainder of the peptide solution was incubated at room temperature with 150 µL PBS for ~1 hr and then examined by reverse phase HPLC. The HPLC (not shown) showed 58% $^{18}$F unbound and 42% still attached to the peptide. The data indicate that $^{18}$F—Al-DTPA complex may be unstable when mixed with phosphate.

The labeled peptide was purified by applying the labeled peptide solution onto a 1 cc (30 mg) WATERS® HLB column (Part #186001879) and washing with 300 µL water to remove unbound F-18. The peptide was eluted by washing the column with 2×100 µL 1:1 EtOH/H$_2$O. The purified peptide was incubated in water at 25° C. and analyzed by reverse phase HPLC (not shown). The HPLC analysis showed that the $^{18}$F-labeled IMP 272 was not stable in water. After 40 min incubation in water about 17% of the $^{18}$F was released from the peptide, while 83% was retained (not shown).

The peptide (16 µL 2 mM IMP 272, 48 µg) was labeled with $^{18}$F and analyzed for antibody binding by size exclusion HPLC. The size exclusion HPLC showed that the peptide bound hMN-14×679 but did not bind to the irrelevant bispecific antibody hMN-14×734 (not shown).

IMP 272 $^{18}$F Labeling with Other Metals

A ~3 μL aliquot of the metal stock solution (6×10$^{-9}$ mol) was placed in a polypropylene cone vial and mixed with 75 μL $^{18}$F (as received), incubated at room temperature for ~2 min and then mixed with 20 μL of a 2 mM (4×10$^{-8}$ mol) IMP 272 solution in 0.1 M NaOAc pH 4 buffer. The solution was heated in a heating block at 100° C. for 15 min and analyzed by reverse phase HPLC. IMP 272 was labeled with indium (24%), gallium (36%), zirconium (15%), lutetium (37%) and yttrium (2%) (not shown). These results demonstrate that the $^{18}$F metal labeling technique is not limited to an aluminum ligand, but can also utilize other metals as well. With different metal ligands, different chelating moieties may be utilized to optimize binding of an F-18-metal conjugate.

Production and Use of a Serum-Stable $^{18}$F-Labeled Peptide IMP 449

The peptide, IMP 448 D-Ala-D-Lys(HSG)-D-Tyr-D-Lys (HSG)-NH$_2$ MH$^+$ 1009 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA. The peptide, IMP 448, 0.0757g (7.5×10$^{-5}$ mol) was mixed with 0.0509 g (9.09×10$^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449.

$^{18}$F Labeling of IMP 449

The peptide IMP 449 (0.002 g, 1.37×10$^{-6}$ mol) was dissolved in 686 μL (2 mM peptide solution) 0.1 M NaOAc pH 4.02. Three microliters of a 2 mM solution of Al in a pH 4 acetate buffer was mixed with 15 μL, 1.3 mCi of $^{18}$F. The solution was then mixed with 20 μL of the 2 mM IMP 449 solution and heated at 105° C. for 15 min. Reverse phase HPLC analysis showed 35% ($t_R$~10 min) of the activity was attached to the peptide and 65% of the activity was eluted at the void volume of the column (3.1 min, not shown) indicating that the majority of activity was not associated with the peptide. The crude labeled mixture (5 μL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose $^{18}$F Labeling

Further studies with purified IMP 449 demonstrated that the $^{18}$F-labeled peptide was highly stable (91%, not shown) in human serum at 37° C. for at least one hour and was partially stable (76%, not shown) in human serum at 37° C. for at least four hours. Additional studies were performed in which the IMP 449 was prepared in the presence of ascorbic acid as a stabilizing agent. In those studies (not shown), the metal-$^{18}$F-peptide complex showed no detectable decomposition in serum after 4 hr at 37° C. The mouse urine 30 min after injection of $^{18}$F-labeled peptide was found to contain $^{18}$F bound to the peptide (not shown). These results demonstrate that the $^{18}$F-labeled peptides disclosed herein exhibit sufficient stability under approximated in vivo conditions to be used for $^{18}$F imaging studies.

For studies in the absence of ascorbic acid, $^{18}$F ~21 mCi in ~400 μL, of water was mixed with 9 μL, of 2 mM AlCl$_3$ in 0.1 M pH 4 NaOAc. The peptide, IMP 449, 60 μL, (0.01 M, 6×10$^{-7}$ mol in 0.5 NaOH pH 4.13) was added and the solution was heated to 110° C. for 15 min. The crude labeled peptide was then purified by placing the reaction solution in the barrel of a 1 cc WATERS® HLB column and eluting with water to remove unbound $^{18}$F followed by 1:1 EtOH/H$_2$O to elute the $^{18}$F-labeled peptide. The crude reaction solution was pulled through the column into a waste vial and the column was washed with 3×1 mL fractions of water (18.97 mCi). The HLB column was then placed on a new vial and eluted with 2×200 μL, 1:1 EtOH/H$_2$O to collect the labeled peptide (1.83 mCi). The column retained 0.1 mCi of activity after all of the elutions were complete. An aliquot of the purified $^{18}$F-labeled peptide (20 μL) was mixed with 200 μL, of pooled human serum and heated at 37° C. Aliquots were analyzed by reverse phase HPLC. The results showed the relative stability of $^{18}$F-labeled purified IMP 449 at 37° C. at time zero, one hour (91% labeled peptide), two hours (77% labeled peptide) and four hours (76% labeled peptide) of incubation in human serum (not shown). It was also observed that $^{18}$F-labeled IMP 449 was stable in TFA solution, which is occasionally used during reverse phase HPLC chromatography. There appears to be a general correlation between stability in TFA and stability in human serum observed for the exemplary $^{18}$F-labeled molecules described herein. These results demonstrate that $^{18}$F-labeled peptide, produced according to the methods disclosed herein, shows sufficient stability in human serum to be successfully used for in vivo labeling and imaging studies, for example using PET scanning to detect labeled cells or tissues. Finally, since IMP 449 peptide contains a thiourea linkage, which is sensitive to radiolysis, several products are observed by RP-HPLC. However, when ascorbic acid is added to the reaction mixture, the side products generated were markedly reduced.

Example 19

In Vivo Studies with Pretargeting Using MN-15-679 DNL Construct and $^{18}$F-Labeled Peptide $^{18}$F-labeled IMP 449 is prepared as follows. The $^{18}$F, 54.7 mCi in ~0.5 mL is mixed with 3 μL, 2 mM Al in 0.1 M NaOAc pH 4 buffer. After 3 min 10 μL, of 0.05 M IMP 449 in 0.5 M pH 4 NaOAc buffer is added and the reaction is heated in a 96° C. heating block for 15 min. The contents of the reaction are removed with a syringe. The crude labeled peptide is then purified by HPLC on a C$_{18}$ column. The flow rate is 3 mL/min. Buffer A is 0.1% TFA in water and Buffer B is 90% acetonitrile in water with 0.1% TFA. The gradient goes from 100% A to 75/25 A:B over 15 min. There is about 1 min difference in retention time ($t_R$) between the labeled peptide, which eluted first and the unlabeled peptide. The HPLC eluent is collected in 0.5 min (mL) fractions. The labeled peptide has a $t_R$ between 6 to 9 min depending on the column used. The HPLC purified peptide sample is further processed by diluting the fractions of interest two fold in water and placing the solution in the barrel of a 1 cc WATERS® HLB column. The cartridge is eluted with 3×1 mL water to remove acetonitrile and TFA followed by 400 μL, 1:1 EtOH/H$_2$O to elute the $^{18}$F-labeled peptide. The purified [Al$^{18}$F] IMP 449 elutes as a single peak on an analytical HPLC C$_{18}$ column (not shown).

Female athymic mice (nu/nu) bearing GW-39 xenografts are used for in vivo studies. Three of the mice are injected with hMN-15-679 DNL construct (162 µg) followed with [Al$^{18}$F] IMP 449 18 h later. The hMN-15-679 DNL construct is a humanized bispecific antibody of use for tumor imaging studies, with divalent binding to the CEA tumor antigen and monovalent binding to HSG. One mouse is injected with peptide alone. All of the mice are necropsied at 1 h post peptide injection. Tissues are counted immediately. Comparison of mean distributions shows substantially higher levels of $^{18}$F-labeled peptide localized in the tumor than in any normal tissues in the presence of tumor-targeting bispecific antibody. The results demonstrate that $^{18}$F labeled peptide used in conjunction with an hMN-15 containing antibody construct, such the the hMN-15-679 DNL construct, provide suitable targeting of the $^{18}$F label to perform in vivo imaging, such as PET imaging analysis.

Example 20

AD and DDD Sequence Variants

In certain preferred embodiments, the AD and DDD sequences incorporated into the DNL complexes comprise the amino acid sequences of AD2 (SEQ ID NO:14) and DDD2 (SEQ ID NO:12), as described above. However, in alternative embodiments sequence variants of the AD and/or DDD moieties may be utilized in construction of the cytokine-MAb DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:11 below. (See FIG. 1 of Kinderman et al., 2006.) The skilled artisan will realize that in designing sequence variants of the DDD sequence, one would desirably avoid changing any of the underlined residues, while conservative amino acid substitutions might be made for residues that are less critical for dimerization and AKAP binding.

```
Human DDD sequence from protein kinase A
                                       (SEQ ID NO: 11)
SHIQIPPGLTELLQGYTVEVLRQQPPDLVEFAVEYFTRLREARA
```

Alto et al. (2003) performed a bioinformatic analysis of the AD sequence of various AKAP proteins to design an RII selective AD sequence called AKAP-IS (NO:13), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:13 below.

```
            AKAP-IS sequence
                                       (SEQ ID NO: 13)
QIEYLAKQIVDNAIQQA
```

Similarly, Gold (2006) utilized crystallography and peptide screening to develop a SuperAKAP-IS sequence (SEQ ID NO:27), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare cytokine-MAb DNL constructs. Other alternative sequences that might be substituted for the AKAP-IS AD sequence are shown in SEQ ID NO:28-30. Substitutions relative to the AKAP-IS sequence are underlined. It is anticipated that, as with the AKAP-IS sequence shown in SEQ ID NO:14, the AD moiety may also include the additional N-terminal residues cysteine and glycine and C-terminal residues glycine and cysteine.

```
SuperAKAP-IS
                                       (SEQ ID NO: 27)
QIEYVAKQIVDYAIHQA Alternative AKAP sequences
                                       (SEQ ID NO: 28)
QIEYKAKQIVDHAIHQA (SEQ ID NO: 29)
QIEYHAKQIVDHAIHQA (SEQ ID NO: 30)
QIEYVAKQIVDHAIHQA
```

Stokka et al. (2006) also developed peptide competitors of AKAP binding to PKA, shown in SEQ ID NO:31-33. The peptide antagonists were designated as Ht31 (SEQ ID NO:31), RIAD (SEQ ID NO:32) and PV-38 (SEQ ID NO:33). The Ht-31 peptide exhibited a greater affinity for the RII isoform of PKA, while the RIAD and PV-38 showed higher affinity for RI.

```
Ht31
                                       (SEQ ID NO: 31)
DLIEEAASRIVDAVIEQVKAAGAY

RIAD
                                       (SEQ ID NO: 32)
LEQYANQLADQIIKEATE

PV-38
                                       (SEQ ID NO: 33)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:13). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:34-36.

AKAP-IS
(SEQ ID NO: 13)
QIEYL<u>A</u>KQ<u>I</u>VDN<u>A</u>IQQ<u>A</u>

AKAP7δ-wt-pep
(SEQ ID NO: 34)
PEDAELVRLSKRLVENAVLKAVQQY

AKAP7δ-L304T-pep
(SEQ ID NO: 35)
PEDAELVRTSKRLVENAVLKAVQQY

AKAP7δ-L308D-pep

PEDAELVRLSKRDVENAVLKAVQQY (SEQ ID NO:36)

Can et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:11. Residues that were particularly conserved are further indicated by italics. The residues overlap with, but are not identical to those suggested by Kinderman et al. (2006) to be important for binding to AKAP proteins.

(SEQ ID NO: 11)
SH<u>I</u>Q<u>I</u>PP<u>GL</u>T<u>ELLQGY</u>T<u>V</u>E<u>VLRQQ</u>PP<u>DLVEFA</u>VE<u>YF</u>TR<u>LREA</u>R<u>A</u>

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

The skilled artisan will realize that these and other amino acid substitutions in the antibody moiety or linker portions of the DNL constructs may be utilized to enhance the therapeutic and/or pharmacokinetic properties of the resulting DNL constructs.

Example 21

Reactivity of MN-3 and MN-15 with CEA, NCA-90 and NCA-95 by Indirect Flow Cytometry The reacitivty of antibodies was tested by flow cytometry with a Becton-Dickinson FACSCAN®. The biotinylated second antibody was directed against mouse IgG and was detected by a streptavidin/phycoerythrin conjugate. Tests were carried out with antibodies at 1/50 dilution of 1 mg/ml stocks.

The antibodies MN-3 and MN-15 were teseted for recognition of HeLa cells transfected with cDNA coding for CEA (HeLa-CEA2), NCA-90 (HeLa-KNC6/S44) and NCA-95 (HeLa-CGM6/1). As a negative control, HeLa cells transfected with the plasmid pSV2-Neo (control HeLa cells, HeLa-NeoA) were used. In addition to the antibodies MN-3 and MN-15, three control antibodies were included:

MAb 47 which cross reacts with CEA and NCA-95, but not NCA-90

MAb A which reacts with CEA

MAb NA which reacts with NCA-90

The results of the analysis by indirect fluorescence flow cytometry showed that MN-3 binds NCA-90 and also CEA, but not NCA-95 (not shown). In contrast, MN-15 binds to all three antigens—CEA, NCA-90 and NCA-95 (not shown). Control antibodies included in the panel tested showed the expected cross-reactivities, as predicted from the literature (Berling et al., Cancer Res 1990, 50:6534-39).

What is claimed is:

1. A chimeric, humanized or human Class I anti-CEA antibody or fragment thereof, wherein the Class I anti-CEA antibody or fragment thereof comprises the light chain variable region CDR sequences SASSRVSYIH (SEQ ID NO:1); GTSTLAS (SEQ ID NO:2); and QQWSYNPPT (SEQ ID NO:3); and the heavy chain variable region CDR sequences DYYMS (SEQ ID NO:4); FIANKANGHTTDYSPSVKG (SEQ ID NO:5); and DMGIRWNFDV (SEQ ID NO:6), wherein the antibody or fragment thereof comprises human antibody IgG4 constant region sequences.

2. The antibody or fragment thereof of claim 1, wherein the antibody or fragment binds to CEACAM5, CEACAM6 and granulocytes.

3. The antibody or fragment thereof of claim 1, wherein the antibody or fragment thereof is a chimeric antibody or fragment thereof.

4. The antibody or fragment thereof of claim 3, wherein the chimeric antibody or fragment thereof comprises the variable region amino acid sequences of SEQ ID NO:9 and SEQ ID NO:10.

5. The antibody or fragment thereof of claim 1, wherein antibody or fragment thereof is a humanized antibody or fragment thereof.

6. The antibody or fragment thereof of claim 5, wherein the humanized antibody or fragment thereof comprises the amino acid sequences of SEQ ID NO:7 and SEQ ID NO:8.

7. The antibody or fragment thereof of claim 1, wherein the antibody or fragment is a naked antibody or fragment.

8. The antibody or fragment thereof of claim 1, wherein the antibody or fragment is conjugated to at least one diagnostic or therapeutic agent.

9. The antibody or fragment thereof of claim 8, wherein the therapeutic agent is selected from the group consisting of an antibody, an antibody fragment, a cytotoxic agent, a drug, a radionuclide, boron atoms, an immunomodulator, a photoactive therapeutic agent, an immunoconjugate, an oligonucleotide and a hormone.

10. The antibody or fragment thereof of claim 9, wherein the cytotoxic agent is a drug or toxin.

11. The antibody or fragment thereof of claim 10, wherein the drug has a pharmaceutical property selected from the group consisting of antimitotic, alkylating, antimetabolite, antiangiogenic, apoptotic, alkaloid, COX-2, and antibiotic agents.

12. The antibody or fragment thereof of claim 10, wherein the drug is selected from the group consisting of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin and doxorubicins.

13. The antibody or fragment thereof of claim 10, wherein the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicin (2P-DOX), pro-2P-DOX, cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, temazolomide, transplatinum, thalidomide, thioguanine, thiotepa, teniposide, topotecan, uracil mustard, vinorelbine, vinblastine, vincristine and vinca alkaloids.

14. The antibody or fragment thereof of claim 10, wherein the toxin is selected from the group consisting of ricin, abrin, alpha toxin, saporin, ribonuclease (RNase), onconase, DNase I, Staphylococcal enterotoxin-A, pokeweed antiviral protein, gelonin, diphtheria toxin, *Pseudomonas* exotoxin and *Pseudomonas* endotoxin.

15. The antibody or fragment thereof of claim 9, wherein the oligonucleotide is selected from the group consisting of an RNAi and a siRNA.

16. The antibody or fragment thereof of claim 9, wherein the radionuclide is selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Rh, $^{149}$Pm, $^{169}$Er, $^{194}$Ir, $^{58}$Co, $^{80m}$Br, $^{99m}$Tc, $^{103m}$Rh, $^{109}$Pt, $^{119}$Sb, $^{125}$I, $^{189m}$Os, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br, $^{169}$Yb, and an alpha-particle emitting radionuclide.

17. The antibody or fragment thereof of claim 9, wherein the immunomodulator is selected from the group consisting of a cytokine, a chemokine, a stem cell growth factor, a lymphotoxin, an hematopoietic factor, a colony stimulating factor (CSF), an interferon, erythropoietin, thrombopoietin, a tumor necrosis factor (TNF), an interleukin (IL), granulocyte-colony stimulating factor (G-CSF), granulocyte macrophage-colony stimulating factor (GM-CSF) and a stem cell growth factor designated "S1 factor".

18. The antibody or fragment thereof of claim 17, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factors, interferon-α, interferon-Iβ, interferon-γ, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

19. The antibody or fragment thereof of claim 17, wherein the chemokine is selected from the group consisting of RANTES, MCAF, MIP1-alpha, MIP1-beta and IP-10.

20. The antibody or fragment thereof of claim 1, wherein the antibody fragment is selected from the group consisting of F(ab')$_2$, Fab', Fab, Fv, single domain antibody (VHH) and scFv.

21. The antibody or fragment thereof of claim 5, wherein the framework regions of the light and heavy chain variable regions of the humanized antibody or fragment thereof comprise at least one amino acid substitution selected from the heavy chain amino acid residues 28, 29, 30, 48 and 49 of SEQ ID NO:10 and the light chain amino acid residues 21, 47 and 60 of SEQ ID NO:9.

22. The antibody or fragment thereof of claim 8, wherein the diagnostic agent is selected from the group consisting of a radionuclide, a radiological contrast agent, a paramagnetic ion, a metal, a fluorescent label, a chemiluminescent label, an ultrasound contrast agent and a photoactive agent.

23. The antibody or fragment thereof of claim 22, wherein the radionuclide is selected from the group consisting of $^{110}$In, $^{111}$In, $^{177}$Lu, $^{18}$Fe, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb and $^{83}$Sr.

24. The antibody or fragment thereof of claim 22, wherein the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

25. The antibody or fragment thereof of claim 22, wherein the fluorescent label is selected from the group consisting of Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl rhodamine, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red.

26. The antibody or fragment thereof of claim 1, wherein the antibody comprises a Ser241Pro point mutation in the hinge region of the antibody or fragment.

27. The antibody or fragment thereof of claim 1, wherein the antibody or fragment thereof is a bispecific antibody.

28. The bispecific antibody of claim 27, wherein the bispecific antibody comprises a first chimeric, humanized or human Class I anti-CEA antibody or fragment thereof and a second antibody or fragment thereof.

29. The bispecific antibody of claim 27, wherein the bispecific antibody is a fusion protein.

30. The bispecific antibody of claim 28, wherein the second antibody or fragment thereof binds to a tumor-associated antigen (TAA) or a hapten on a targetable construct.

31. The bispecific antibody of claim 30, wherein the TAA is selected from the group consisting of carbonic anhydrase IX, CCL19, CCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-13, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-.alpha., TRAIL receptor (R1 and R2), VEGFR, EGFR, P1GF, complement factors C3, C3a, C3b, C5a, C5 and an oncogene product.

32. The bispecific antibody of claim 30, wherein the second antibody is selected from the group consisting of hPAM4, hA20, hA19, hIMMU31, hLL1, hLL2, hMu-9, hL243, hMN-14, hMN-3, hR1, h679 and 734.

33. A fusion protein comprising comprising a chimeric, humanized or human Class I anti-CEA antibody or fragment thereof according to claim 1.

34. The fusion protein of claim 33, further comprising a DDD (dimerization and docking domain) moiety or an AD (anchor domain) moiety, wherein said DDD moiety has a peptide sequence from a dimerization and docking domain of protein kinase A and said AD moiety has a peptide sequence from an anchoring domain of an AKAP (A-kinase anchoring protein).

35. The fusion protein of claim 34, wherein the DDD moiety as an amino acid sequence selected from the group consisting of DDD1 (SEQ ID NO:11) and DDD2 (SEQ ID NO:12).

36. The fusion protein of claim 34, wherein the AD moiety as an amino acid sequence selected from the group consisting of AD1 (SEQ ID NO:13) and AD2 (SEQ ID NO:14).

* * * * *

SEQUENCE LISTING

```
<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ala Ser Ser Arg Val Ser Tyr Ile His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Thr Ser Thr Leu Ala Ser
1               5

<210> SEQ ID NO 3
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Gln Gln Trp Ser Tyr Asn Pro Pro Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Tyr Met Ser
1               5

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Ile Ala Asn Lys Ala Asn Gly His Thr Thr Asp Tyr Ser Pro Ser
1               5                   10                  15

Val Lys Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Met Gly Ile Arg Trp Asn Phe Asp Val
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Leu Thr Gln Ser Pro Ser Ser Leu Ser Ala Ser Val Gly
1               5                   10                  15

Asp Arg Val Thr Met Thr Cys Ser Ala Ser Ser Arg Val Ser Tyr Ile
            20                  25                  30

His Trp Tyr Gln Gln Lys Pro Gly Lys Ala Pro Lys Arg Trp Ile Tyr
        35                  40                  45

Gly Thr Ser Thr Leu Ala Ser Gly Val Pro Ala Arg Phe Ser Gly Ser
    50                  55                  60

Gly Ser Gly Thr Asp Phe Thr Phe Thr Ile Ser Ser Leu Gln Pro Glu
65                  70                  75                  80
```

Asp Ile Ala Thr Tyr Tyr Cys Gln Gln Trp Ser Tyr Asn Pro Pro Thr
                85                  90                  95

Phe Gly Gln Gly Thr Lys Val Glu Ile Lys Arg
            100                 105

<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Glu Ser Gly Gly Val Val Gln Pro Gly Arg
1               5                   10                  15

Ser Leu Arg Leu Ser Cys Ser Ser Gly Phe Ala Leu Thr Asp Tyr
                20                  25                  30

Tyr Met Ser Trp Val Arg Gln Ala Pro Gly Lys Gly Leu Glu Trp Leu
            35                  40                  45

Gly Phe Ile Ala Asn Lys Ala Asn Gly His Thr Thr Asp Tyr Ser Pro
50                  55                  60

Ser Val Lys Gly Arg Phe Thr Ile Ser Arg Asp Asn Ser Lys Asn Thr
65                  70                  75                  80

Leu Phe Leu Gln Met Asp Ser Leu Arg Pro Glu Asp Thr Gly Val Tyr
                85                  90                  95

Phe Cys Ala Arg Asp Met Gly Ile Arg Trp Asn Phe Asp Val Trp Gly
            100                 105                 110

Gln Gly Thr Pro Val Thr Val Ser Ser
        115                 120

<210> SEQ ID NO 9
<211> LENGTH: 107
<212> TYPE: PRT
<213> ORGANISM: Mus sp.

<400> SEQUENCE: 9

Asp Ile Gln Leu Thr Gln Ser Pro Ala Ile Met Ser Ala Ser Pro Gly
1               5                   10                  15

Glu Lys Val Thr Met Thr Cys Ser Ala Ser Ser Arg Val Ser Tyr Ile
                20                  25                  30

His Trp Tyr Gln Gln Lys Ser Gly Thr Ser Pro Lys Arg Trp Ile Tyr
            35                  40                  45

Gly Thr Ser Thr Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Tyr Asn Pro Pro Thr
                85                  90                  95

Phe Gly Ala Gly Thr Lys Leu Glu Leu Lys Arg
            100                 105

<210> SEQ ID NO 10
<211> LENGTH: 121
<212> TYPE: PRT
<213> ORGANISM: Mus sp.

<400> SEQUENCE: 10

```
Glu Val Arg Leu Val Glu Ser Gly Gly Gly Leu Val Gln Gly Pro Gly
1               5                   10                  15

Ser Leu Arg Leu Ser Cys Ala Ala Ser Gly Phe Ala Leu Thr Asp Tyr
            20                  25                  30

Tyr Met Ser Trp Val Arg Gln Ser Pro Gly Lys Thr Leu Glu Trp Leu
        35                  40                  45

Gly Phe Ile Ala Asn Lys Ala Asn Gly His Thr Thr Asp Tyr Ser Pro
    50                  55                  60

Ser Val Lys Gly Arg Phe Thr Ile Ser Arg Asp Asn Ser Gln Thr Ile
65                  70                  75                  80

Leu Tyr Leu Gln Met Asn Thr Leu Arg Thr Glu Asp Ser Ala Thr Tyr
                85                  90                  95

Tyr Cys Ala Arg Asp Met Gly Ile Arg Trp Asn Phe Asp Val Trp Gly
                100                 105                 110

Gln Gly Thr Thr Val Thr Val Ser Ser
            115                 120
```

<210> SEQ ID NO 11
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40
```

<210> SEQ ID NO 12
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
            35                  40                  45
```

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Gln Ile Glu Tyr Leu Ala Lys Gln Ile Val Asp Asn Ala Ile Gln Gln
1               5                   10                  15

Ala
```

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Gly Ser Gly Gly Gly Gly Ser
1               5                   10

<210> SEQ ID NO 16
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 18

Gly Gly Gly Gly Ser Gly Gly Gly Cys Gly
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys(SS-tbu)

<400> SEQUENCE: 19

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys(SS-tbu)

<400> SEQUENCE: 20

Cys Gly Gln Ile Glu Tyr Leu Ala Lys Gln Ile Val Asp Asn Ala Ile
1               5                   10                  15

Gln Gln Ala Gly Cys Gly
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(S-tbu)
<220> FEATURE:
<221> NAME/KEY: MOD_RES
<222> LOCATION: (21)..(21)
<223> OTHER INFORMATION: Cys(S-tbu)

<400> SEQUENCE: 21

Cys Gly Gln Ile Glu Tyr Leu Ala Lys Gln Ile Val Asp Asn Ala Ile
1               5                   10                  15

Gln Gln Ala Gly Cys Gly
            20

<210> SEQ ID NO 22
<211> LENGTH: 63
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 22

Lys Ser His His His His His His Gly Ser Gly Gly Gly Ser Gly
1               5                   10                  15

Gly Gly Cys Gly His Ile Gln Ile Pro Pro Gly Leu Thr Glu Leu Leu
            20                  25                  30

Gln Gly Tyr Thr Val Glu Val Leu Arg Gln Gln Pro Asp Leu Val
        35                  40                  45

Glu Phe Ala Val Glu Tyr Phe Thr Arg Leu Arg Glu Ala Arg Ala
    50                  55                  60

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tctagacaca ggacctcatc atggccttga cctttgcttt actgg              45

<210> SEQ ID NO 24
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggatccatga tggtgatgat ggtgtgactt ttccttactt cttaaacttt cttgc    55

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agatctggcg cacctgaact cctg                                     24

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaattcggat cctttacccg gagacaggga gag                           33

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 27

Gln Ile Glu Tyr Val Ala Lys Gln Ile Val Asp Tyr Ala Ile His Gln
1               5                   10                  15

Ala

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ile Glu Tyr Lys Ala Lys Gln Ile Val Asp His Ala Ile His Gln
1               5                   10                  15

Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ile Glu Tyr His Ala Lys Gln Ile Val Asp His Ala Ile His Gln
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Ile Glu Tyr Val Ala Lys Gln Ile Val Asp His Ala Ile His Gln
1               5                   10                  15

Ala

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
      peptide

<400> SEQUENCE: 32

Leu Glu Gln Tyr Ala Asn Gln Leu Ala Asp Gln Ile Ile Lys Glu Ala
1               5                   10                  15

Thr Glu

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Glu Glu Leu Ala Trp Lys Ile Ala Lys Met Ile Trp Ser Asp Val
1               5                   10                  15

Phe Gln Gln Cys
            20

<210> SEQ ID NO 34
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 37
```

<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 37

His His His His His His
1               5

<210> SEQ ID NO 38
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Glu Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Ser Tyr
            20                  25                  30

Ala Met Tyr Trp Val Arg Gln Ala Pro Gly Lys Gly Leu Glu Trp Val
        35                  40                  45

Ala Ile Ile Trp Asp Asp Gly Ser Asp Gln His Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
        115                 120                 125

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Val Glu Ile Lys
            100                 105